United States Patent
Stewart et al.

(10) Patent No.: US 7,754,684 B2
(45) Date of Patent: *Jul. 13, 2010

(54) MACROMOLECULAR PLATINUM CHELATES

(75) Inventors: Donald R. Stewart, Fort Worth, TX (US); Paul Sood, Dallas, TX (US); K. Bruce Thurmond, Plano, TX (US); David P. Nowotnik, Colleyville, TX (US); Sergiy V. Shevchuk, Carrollton, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 90 days.

This patent is subject to a terminal disclaimer.

(21) Appl. No.: 10/865,450

(22) Filed: Jun. 10, 2004

(65) Prior Publication Data
US 2005/0038109 A1 Feb. 17, 2005

Related U.S. Application Data

(60) Provisional application No. 60/478,019, filed on Jun. 11, 2003.

(51) Int. Cl.
*A61K 38/00* (2006.01)
(52) U.S. Cl. .................................................. 514/6
(58) Field of Classification Search ........................ None
See application file for complete search history.

(56) References Cited

U.S. PATENT DOCUMENTS

| | | | |
|---|---|---|---|
| 4,225,529 A * | 9/1980 | Hydes et al. ................. | 556/137 |
| 4,614,811 A * | 9/1986 | Gandolfi ..................... | 556/137 |
| 5,108,921 A | 4/1992 | Low et al. | |
| 5,416,016 A | 5/1995 | Low et al. | |
| 5,595,756 A * | 1/1997 | Bally et al. ................. | 424/450 |
| 5,635,382 A | 6/1997 | Low et al. | |
| 5,688,488 A | 11/1997 | Low et al. | |
| 5,820,847 A | 10/1998 | Low et al. | |
| 5,965,118 A | 10/1999 | Duncan et al. | |
| 6,521,431 B1 | 2/2003 | Kiser et al. | |
| 6,692,734 B2 | 2/2004 | Stewart et al. | |
| 7,166,733 B2 | 1/2007 | Nowotnik et al. | |
| 2003/0078339 A1 | 4/2003 | Kiser et al. | |
| 2004/0175387 A1* | 9/2004 | Sood et al. ............... | 424/178.1 |

OTHER PUBLICATIONS

Sporn et at, "Chemoprevention of Cancer," Carcinogenesis, vol. 21 (2000), 525-530.*

Gibson Dan, et al, "Multinuclear (platinum-195, nitrogen-15, carbon-13) NMR studies of the reactions between cis-diaminediaquaplatinum(II) complexes and aminomalonate," Inorganic chemistry (1990), pp. 5125-5129.*
Antony, A.S. et al. "Stuies of the Role of a Particulate Folate-binding Protein in the Uptake of 5-Methyltetrahydrofolate by Cultured Human KB Cells" *J. Biol. Chem.* (Dec. 5, 1985) 260(28):14911-14917.
Behr, T.M. et al. "Imaging Tumors withPeptide-based Radioligands" *Q.J. Nucl. Med.* (2001) 45(2):189-200.
Leamon, C.P. and P.S. Low "Folate-mediated targeting: from diagnostics to drug and gene delivery" *Drug Discov. Today* (Jan. 2001) 6(1):44-51.
Leu, Y.L. et al. Design and Synthesis of Water-Soluble Glucuronide Derivatives of Camptothecin for Cancer Prodrug Monotherapy and Antibody-Directed Enzyme Prodrug Thereapy (ADEPT) *J. Med. Chem.* (1999) 42:3623-3628.
Rao, P.S. et al. "$^{99m}$Tc labeled VIP analog: evaluation for imaging colorectal cancer" *Nucl. Med. Biol.* (2001) 28:445-450.
Schally, A.V. and A. Nagy "Cancer chemotherapy based on targeting of cytotoxic peptide conjugates to their receptors on tumors" *Eur. J. Endocrinol.* (1999) 141(1):1-14.
Suzawa, T. et al. "Synthesis and HPLC analysis of enzymatically cleavable linker consisting of poly(ethylene glycol) and dipeptide for the development of immunoconjugate" *J. Control Release* (2000) 69(1):27-41.
Wang, S. and P.S. Low "Folate-mediated targeting of antineoplastic drugs, imaging agents, and nucleic acids to cancer cells" *J. Control Release* (1998) 53(1-3):39-48.
Wardman, P. "The Mechanism of Radiosensitizaton by Electron-Affinic Compounds" *Radiat. Phys. Chem.* (1987) 30(5/6):423-432.
International Search Report and Written Opinion for PCT/US2004/018509 dated Apr. 23, 2005.

* cited by examiner

*Primary Examiner*—Cecilia Tsang
*Assistant Examiner*—Thomas S Heard
(74) *Attorney, Agent, or Firm*—Antoinette F. Konski; Foley & Lardner LLP

(57) ABSTRACT

The present invention relates to platinum complex chemotherapeutic compounds having the generic structure:

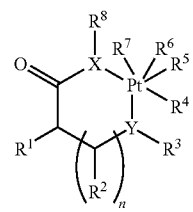

wherein n is 0 or 1 and, preferably, one of $R^1$, $R^2$, $R^3$ or $R^8$ is a -(linker)-polymer group that may contain up to four additional platinum chelates.

15 Claims, 15 Drawing Sheets

Table 2. Comparison of representative compounds C1-C13 of this invention versus carboplatin.

| Compound No. | Structure | Pt release (% at 24 h) | TGI Dose (mg Pt/kg) | Mean max BWL (%) | Toxic deaths | Relative TGI* |
|---|---|---|---|---|---|---|
| C1 | p(HPMA)-Ama=Pt=DACH | 23.8 | 20 | -21.6 | 6/10 | + |
| C2 | p(HPMA)-GFLG-Ama-Pt=DACH | 2.6 | 25 | -6.5 | 0/10 | + |
| C3 | p(HPMA)-GG-Ama-Pt=DACH (High MW) | 6.2 | 5 | -22.1 | 8/8 | ++ |
| C4 | p(HPMA)-GFLG-Asp=Pt=DACH | 5.4 | 20 | -12.0 | 1/10 | +++ |
| C5 | p(HPMA)-GG-Ama-Pt=DACH (Low MW) | 5.5 | 9 | -6.3 | 3/10 | + |
| C6 | p(HPMA)-GG-Asp=Pt=DACH | 10.6 | 5.5 | -9.4 | 1/10 | ++ |
| C7 | p(HPMA)-GG-C3-Sulf-Ama=Pt=DACH | 1.9 | 75 | -30.2 | 10/10 | ++ |
| C8 | p(HPMA)-GG-C3-Sulf-Asp=Pt=DACH | 4.3 | 50 | -26.7 | 8/10 | ++ |
| C9 | p(HPMA)-GFLG-C3-Sulf-Ama=Pt=DACH | 4.5 | 25 | -4.3 | 1/10 | + |
| C10 | p(HPMA)-GFLG-C3-Sulf-Asp=Pt=DACH | 4.6 | 50 | -30.2 | 7/9 | ++ † |
| C11 | p(HPMA)-GGGG-Ama=Pt=DACH | 3.2 | 50 | -27.3 | 7/9 | ++ † |
| C12 | p(HPMA)-GGGG-Asp=Pt=DACH | 6.3 | 20 | -28.1 | 3/9 | +++ |
| C13 | p(HPMA)-GGG-Ama=Pt=DACH | 3.6 | 20 | -8.0 | 0/9 | +++ |

* Key to relative TGI:
+ = Activity equivalent to carboplatin
++ = Activity superior to carboplatin
+++ = Activity greatly superior to carboplatin
† Mice that did not die had very good individual TGI results

FIGURE 15

```
SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Part of larger non-protein polymeric molecule

<400> SEQUENCE: 1

Gly Gly Gly Gly
1

<210> SEQ ID NO 2
<211> LENGTH: 4
<212> TYPE: PRT
<213> ORGANISM: Artificial
<220> FEATURE:
<223> OTHER INFORMATION: Part of larger non-protein polymeric compound.

<400> SEQUENCE: 2

Gly Phe Leu Gly
1
```

MACROMOLECULAR PLATINUM CHELATES

RELATED APPLICATIONS

This application is related to and claims the benefit of Provisional Patent Application Ser. No. 60/478,019, filed 11 Jun. 2003, which is incorporated by reference, including all drawings, as if fully set forth herein.

FIELD OF THE INVENTION

The present invention relates to platinum complexes, in particular platinum complex/polymer conjugates, useful for the treatment of cancer.

BACKGROUND OF THE INVENTION

Since the advent of cisplatin (I) in the late 1960s, platinum complexes have become a mainstay in the practitioner's arsenal of anti-tumor chemotherapeutics. They find use, either alone or in combination with other chemotherapeutic agents, against virtually all solid tumor cancers. All current clinical platinum complex chemotherapeutics share the generic structure of cisplatin; i.e., $Pt(L_1)(L_2)(L_3)(L_4)$, in which $L_1$ and $L_2$ represent two stable cis-monodentate am(m)ine ligands or, as $L_1$-$L_2$, a stable bidentate amine ligand and $L_3$ and $L_4$ represent two monodentate anionic leaving-ligands or, as $L_3$-$L_4$, a bidentate anionic leaving-ligand. Despite their ability to react with many different biomolecules, the mode of action of the Pt complex drugs is presently accepted as involving hydrolytic loss of the anionic leaving-ligands with concomitant formation of the much more reactive aqua (water) ligand complex, which is capable of reacting with DNA to form intra- and inter-strand cross-links, leading to cell death. The usefulness of cisplatin is limited by its therapeutic index (the ratio of the maximum tolerable dose to minimum effective dose), which tends to be relatively low due to the toxicity of the active aqua species and the rapidity with which it forms in vivo. Among the approaches that have been employed to improve the therapeutic index of cisplatin, two have predominated. The first had been to use anionic leaving-ligands that are more stable to hydrolytic cleavage so that the aqua species does not form until the compound has infiltrated a target tumor. To date, this approach has resulted in four clinical platinum complex compounds that exhibit improved pharmaceutical characteristics compared to cisplatin: carboplatin (II), oxaliplatin (III), nedaplatin (IV) and lobaplatin (V).

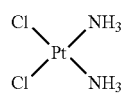

(I)

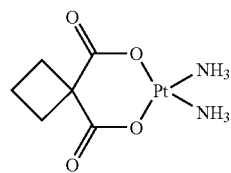

(II)

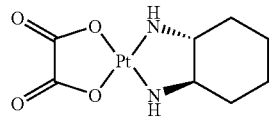

(III)

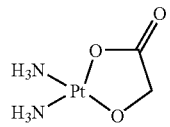

(IV)

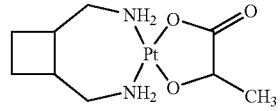

(V)

The second approach, often used in conjunction with the first, is targeting; i.e., combining the platinum complex with a compound that preferentially accumulates in tumors so that, once it passively encounters a tumor or a compound that has a specific affinity for a molecule or receptor expressed on the surface of a neoplastic cell but not a healthy cell. Preferential accumulation in tumors can be achieved by using compounds that take advantage of the "enhanced permeability and retention" (EPR) effect operative in tumors.

Briefly, the EPR effect, which was first described with regard to the preferential permeation into, and retention by, tumor tissues of serum proteins, is the result of defective tissue architecture, changes in permeation mediators and impaired lymphatic drainage in tumors. That is, the vascular endothelium of tumors tends to have relatively large gaps in the endothelial cell-cell junctions compared to normal tissue. This permits larger molecular species to permeate the tissue than is the case for healthy tissue. The altered permeation mediators and impaired lymphatic drainage mechanism then assure that the molecules that have penetrated the tumor stay there. The EPR effect has been used in practice to selectively introduce and retain chemotherapeutics in tumors by tethering small molecule drugs to polymers or nanoparticles that are too large to permeate normal tissue but that readily infiltrate tumor tissue.

For example, U.S. Pat. No. 5,965,118, assigned to Access Pharmaceuticals, Inc., claims an polyacrylamide or polymethacrylamide backbone polymer wherein a portion of the pendant amide groups are linked by a peptide chain to a terminal platinum complex. The remainder of the pendant amide groups are substituted with a water-solubilizing hydroxyalkyl group. The size of the polymer is optimized to be large enough to take advantage of the EPR effect, yet small enough so that any drug remaining in the circulatory system is susceptible to renal elimination. The anionic leaving ligands through which the Pt species are bound to the polymer are bidentate carboxyl or aminoethylamido groups in the '118 patent. The polymer-bound platinum complex is passively transported to the target tumor through the vascular system until it preferentially enters into and is retained in tumors due to the EPR effect where hydrolytic cleavage to an active small molecule aqua species occurs.

U.S. Pat. No. 6,692,734, also assigned to Access Pharmaceuticals, Inc., likewise claims polymer-bound platinum complexes, the difference being that the Pt is bound to the polymer by bidentate N,O-amidomalonate ligands rather than bidentate aminoethylamide or bidentate carboxyl ligands.

What is needed is new, more potent and efficacious Pt complex chemotherapeutics having superior therapeutic indices. The present invention provides such compounds.

SUMMARY OF THE INVENTION

Thus, in one aspect, the present invention relates to a compound having the chemical structure:

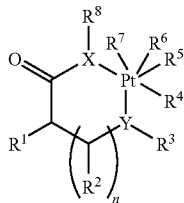

wherein:

n is 0 or 1;

Pt is in a +2 or a +4 oxidation state;

X and Y are independently selected from the group consisting of oxygen, nitrogen and sulfur, provided that, if X or Y is sulfur, the other is nitrogen or oxygen, wherein;

$R^1$ and $R^2$ are independently selected from the group consisting of:
—O;
—$R^9$;
-(1C-6C)alkyl-$R^9$;
-(1C-6C)alkyl-Z$R^9$;
—C(O)Z$R^9$; and,
—C(O)O—R+
-(1C-6C)alkyl-C(O)Z$R^9$, wherein:
Z is selected from the group consisting of oxygen and —NH—;
R+ is selected from the group consisting of Na+ and K+;
$R^9$ is selected from the group consisting of:
hydrogen,
-(1C-6C)alkyl optionally substituted with one or more —OH groups; and,
-(linker)-$R^{10}$, wherein:
-(linker) is one of more entities selected from the group consisting of:
—(OCH$_2$CH$_2$)$_a$O(C=O)$_b$—;
—(CH(OH))$_a$CH$_2$O(C=O)$_b$—;
—NH-(1C-20C)alkyl-C(=O)—;
—NH-poly(ethylene glycol)-NH—; and,

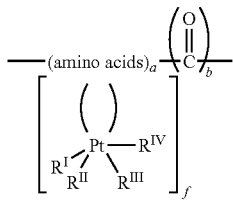

wherein:
a is 0-50;
b is 0 or 1;
f is 0, 1, 2, 3 or 4, provided that for each individual amino acid of the 0 to 50 "a" amino acids, f is 0 or 1;

$R^I$ is the same as $R^4$;
$R^{II}$ is the same as $R^5$;
$R^{III}$ is the same as $R^6$; and,
$R^{IV}$ is the same as $R^7$;
$R^{10}$ is selected from the group consisting of:
hydrogen: and,
a natural, semi-synthetic or synthetic backbone polymer;
provided that:
when Y is nitrogen and the ring is a 5-member ring, $R^1$ is =O;
when Y is nitrogen and the ring is a 6-member ring, $R^2$ is =O;
when $R^2$ is =O, $R^1$ is not =O;
$R^3$ and $R^8$ are independently selected from the group consisting of:
—$R^9$;
-(1C-6C)alkyl-$R^9$;
—C(O)Z$R^9$;
—C(O)$R^9$;
—S(O)$_2$$R^{11}$;
—P(O)(O$R^9$)$_2$(O$R^1$2);
—P(O)(O$R^9$)(O$R^{12}$)$_2$; and,
aryl optionally substituted with one or more entities independently selected from the group consisting of:
—$R^9$
—O$R^9$;
—N$R^9$$R^{12}$;
—NO$_2$;
-halo;
—C≡N; and,
—C(O)Z$R^9$;
$R^{11}$ is selected from the group consisting of:
—$R^9$;
-(1C-6C)alkyl-$R^9$;
—N$R^9$$R^{12}$; and,
aryl optionally substituted with one or more entities selected from the group consisting of:
—$R^9$;
—O$R^9$;
—N$R^9$$R^{12}$;
—NO$_2$;
-halo;
—C≡N;
—C(O)O$R^9$; and,
—C(O)NH$R^9$;
$R^{12}$ is selected from the group consisting of hydrogen and -(1C-6C)alkyl and, when bonded to a phosporus through an oxygen atom, i.e., P—(O$R^{12}$), Na+ and K+;
provided that:
when X and/or Y is oxygen, $R^3$ and/or $R^8$ does not exist;
when X or Y is sulfur, $R^3$ or $R^8$ is -(1C-6C)alkyl;
$R^4$ and $R^5$ are independently selected from the group consisting of:
ammonia;
a primary, secondary or tertiary (1C-6C)alkyl amine;
a (3C-8C)cycloalkyl amine;
an aryl amine;
a nitrogen heteroaryl;
a nitrogen heteroalicyclic;
an aminomethyl nitrogen heteroalicyclic; or,
together, as $R^4$—$R^5$:
a 1,2-, 1,3-, 1,4- or 1,5-diamino (2C-8C)alkane;
a 1,2- or 1,4-diamino (3C-8C)cycloalkane;
a 1,1- or 1,2-di(aminomethyl) (3C-8C)cycloalkane;
a 1,1- or 1,2-di(aminomethyl) heteroalicyclic;

a di(nitrogen heteroaryl); and, a methylene di(nitrogen heteroaryl);

if Pt is in the +2 oxidation state (Pt(II)), $R^6$ and $R^7$ do not exist; and, if Pt is in the +4 oxidation state (Pt(IV)), $R^6$ and $R^7$ are independently selected from the group consisting of —OH, $H_2O$, Cl and (1C-6C)alkyl C(O)—.

In an aspect of this invention:

n is 0;

Y is oxygen; and, all Pt atoms are in the +2 oxidation state.

In an aspect of this invention:

X is oxygen; and, $R^1$ is as described above, except that it cannot be =O and $R^9$ cannot be hydrogen.

In an aspect of this invention:

X is nitrogen or NH;

$R^1$ is as described above; and, $R^8$ is as described above except that $R^9$ cannot be -(linker)-$R^{10}$.

In an aspect of this invention:

X is nitrogen or NH;

$R^1$ is as described above, except that $R^9$ cannot be -(linker)-$R^{10}$; and, $R^8$ is as described above.

In an aspect of this invention:

X is sulfur;

$R^1$ is as described above; and, $R^8$ is (1C-6C)alkyl.

In an aspect of this invention:

n is 0;

Y is nitrogen or NH;

$R^1$ is =O; and, all Pt atoms are in the +2 oxidation state.

In an aspect of this invention:

X is oxygen; and, $R^3$ is as described above.

In an aspect of this invention:

X is nitrogen or NH:

$R^3$ is as described above; and $R^8$ is as described, except that $R^9$ cannot be -(linker)-$R^{10}$.

In an aspect of this invention:

X is nitrogen;

$R^3$ is as described above, except that $R^9$ cannot be -(linker)-$R^{10}$; and, $R^8$ is as described above.

In an aspect of this invention:

X is sulfur; and, $R^3$ is as described above.

In an aspect of this invention:

n is 0;

Y is sulfur;

$R^3$ is -(1C-6C)alkyl; and, all Pt atoms are in the +2 oxidation state.

In an aspect of this invention:

X is oxygen; and, $R^1$ is as described above.

In an aspect of this invention:

X is nitrogen or NH;

$R^1$ is as described above; and, $R^8$ is as described above except that $R^9$ cannot be -(linker)-$R^{10}$.

In an aspect of this invention:

X is nitrogen or NH;

$R^1$ is as described above, except that $R^9$ cannot be -(linker)-$R^{10}$; and, $R^8$ is as described above.

In an aspect of this invention:

n is 1;

Y is oxygen; and, all Pt atoms are in the +2 oxidation state.

In an aspect of this invention:

X is oxygen;

$R^1$ is as described above; and, $R^2$ is as described above, except that $R^9$ cannot be -(linker)-$R^{10}$.

In an aspect of this invention:

X is oxygen;

$R^1$ is as described above, except that $R^9$ cannot be -(linker)-$R^{10}$; and, $R^2$ is as described above.

In an aspect of this invention:

X is nitrogen or NH;

$R^1$ is as described above;

$R^2$ is as described above, except that $R^9$ cannot be -(linker)-$R^{10}$; and, $R^8$ is as described above, except that $R^9$ likewise cannot be -(linker)-$R^{10}$.

In an aspect of this invention:

X is nitrogen or NH;

$R^1$ is as described above, except that $R^9$ cannot be -(linker)-$R^{10}$;

$R^2$ is as described above; and, $R^8$ is as described above, except that R cannot be -(linker)-$R^{10}$.

In an aspect of this invention:

X is nitrogen or NH;

$R^1$ is as described above, except that $R^9$ cannot be -(linker)-$R^{10}$;

$R^2$ is as described above, except that $R^9$ cannot be -(linker)-$R^{10}$; and, $R^8$ is as described above.

In an aspect of this invention:

X is sulfur;

$R^1$ is as described above;

$R^2$ is as described above, except that $R^9$ cannot be -(linker)-$R^{10}$; and, $R^8$ is -(1C-6C)alkyl.

In an aspect of this invention:

X is sulfur;

$R^1$ is as described above, except that $R^9$ cannot be -(linker)-$R^{10}$;

$R^2$ is as described above; and, $R^8$ is -(1C-6C)alkyl.

In an aspect of this invention:

n is 1;

Y is nitrogen or NH;

$R^2$ is =O; and, all Pt atoms are in the +2 oxidation state.

In an aspect of this invention:

X is oxygen;

$R^1$ is as described above, except that it cannot be =O; and, $R^3$ is as described above, except that $R^9$ cannot be -(linker)-$R^{10}$.

In an aspect of this invention:

X is oxygen;

$R^1$ is as described above, except that it cannot be =O and $R^9$ cannot be -(linker)-$R^{10}$; and, $R^3$ is as described above.

In an aspect of this invention:

X is nitrogen or NH;

$R^1$ is as described above, except that it cannot be =O;

$R^3$ is as described above, except that $R^9$ cannot be -(linker)-$R^{10}$; and, $R^8$ is as described above, except that $R^9$ likewise cannot be -(linker)-$R^{10}$.

In an aspect of this invention:

X is nitrogen or NH;

$R^1$ is as described above, except that it cannot be =O and $R^9$ cannot be -(linker)-$R^{10}$;

$R^3$ is as described above; and, $R^8$ is as described above, except that $R^9$ likewise cannot be -(linker)-$R^{10}$.

In an aspect of this invention:

X is nitrogen or NH;

$R^1$ is as described above, except that it cannot be =O and $R^9$ cannot be -(linker)-$R^{10}$;

$R^3$ is as described above, except that $R^9$ cannot be -(linker)-$R^{10}$; and, $R^8$ is as described above.

In an aspect of this invention:

X is sulfur;

$R^1$ is as described above, except that it cannot be =O;

$R^3$ is as described above, except that $R^9$ cannot be -(linker)-$R^{10}$; and, $R^8$ is -(1C-6C)alkyl.

In an aspect of this invention:

X is sulfur;

$R^1$ is as described above, except that it cannot be =O and $R^9$ cannot be -(linker)-$R^{10}$;

$R^3$ is as described above; and, $R^8$ is -(1C-6C)alkyl.

In an aspect of this invention:

n is 1;

Y is sulfur;

$R^3$ is -(1C-6C)alkyl; and, all Pt atoms are in the +2 oxidation state.

In an aspect of this invention:

X is oxygen;

$R^1$ is as described above; and, $R^2$ is as described above, except that $R^9$ cannot be -(linker)-$R^{10}$.

In an aspect of this invention:

X is oxygen;

$R^1$ is as described above, except that $R^9$ cannot be -(linker)-$R^{10}$; and, $R^2$ is as described above.

In an aspect of this invention:

X is nitrogen or NH;

$R^1$ is as described above;

$R^2$ is as described above, except that $R^9$ cannot be -(linker)-$R^{10}$; and, $R^8$ is as described above except that $R^9$ likewise cannot be -(linker)-$R^{10}$.

In an aspect of this invention:

X is nitrogen or NH;

$R^1$ is as described above, except that $R^9$ cannot be -(linker)-$R^{10}$;

$R^2$ is as described above; and, $R^8$ is as described above, except that $R^9$ likewise cannot be -(linker)-$R^{10}$.

In an aspect of this invention:

X is nitrogen or NH;

$R^1$ is as described above, except that $R^9$ cannot be -(linker)-$R^{10}$;

$R^2$ is as described above, except that $R^9$ likewise cannot be -(linker)-$R^{10}$; and, $R^8$ is as described above.

An aspect of this invention is a polymer having the chemical structure:

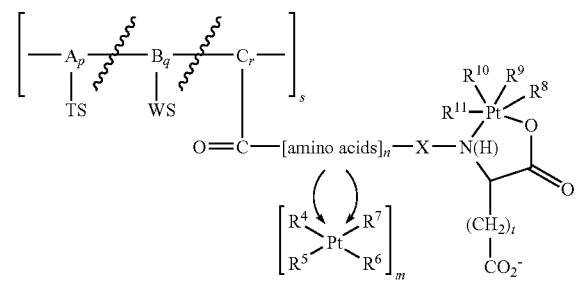

wherein:

A, B and C are polymeric subunits derived from corresponding monomers, each monomer being independently the same as, or different than, each other monomer, wherein:

the hydrogen in brackets, i.e. (H), indicates that the hydrogen atom may or may not be present;

the squiggly lines indicate that the polymer comprises either a random or block copolymer of the monomers;

X is selected from the group consisting of a covalent bond and —NH(CH$_2$)$_v$SO$_2$—, wherein:

v is 0 to 6;

TS is a tumor-seeking group;

WS is a water-solubilizing group;

p is from 0 to 25%, q is from 25 to 99%;

r is from 1 to 50%, wherein:

p+q+r=100%;

s is from about 1 to about 5,000 kDaltons;

t is 0, 1 or 2;

n is 0 to 50;

m is from 0 to 400% of r;

wherein n and m may be the same or different for each Cr group in the compound and with the proviso that each individual amino acid of the 0-50 "n" amino acids can be chelated to only one Pt complex;

$R^4$ and $R^5$ are independently selected from the group consisting of:

ammonia;

a primary, secondary or tertiary (1C-6C)alkyl amine;

a (3C-8C)cycloalkyl amine;

a nitrogen heteroaryl;

a nitrogen heteroalicyclic;

an aminomethyl nitrogen heteroalicyclic; or, together, as $R^4$—$R^5$:

a 1,2-, 1,3-, 1,4 or 1,5-diamino (2C-8C)alkane;

a diamino (3C-8C)cycloalkane;

a di(aminomethyl) (3C-8C)cycloalkane;

a di(aminomethyl)heteroalicyclic;

a di(nitrogen heteroaromatic); and, a methylene [di(nitrogen heteroaromatic)].

In an aspect of this invention the above polymer has the chemical structure:

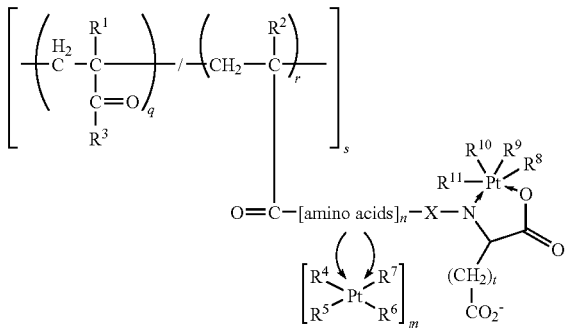

wherein:
X is selected from the group consisting of a covalent bond and —NH—(CH$_2$)$_v$SO$_2$—, wherein:
  v is 0-6;
R$^1$ and R$^2$ are independently selected from the group consisting of hydrogen and —CH$_3$;
R$^3$ is a water-solubilizing group;
q is 25-95%;
r is 1-25%;
q+r=100%;
s is from 1 to 5,000 kD;
t is 0, 1 or 2;
R$^4$ and R$^5$ are independently selected from the group consisting of:
  ammonia;
  a primary, secondary or tertiary (1C-6C)alkyl amine;
  a (3C-8C)cycloalkyl amine;
  a nitrogen heteroaryl;
  a nitrogen heteroalicyclic;
  an aminomethyl nitrogen heteroalicyclic; or,
  together, as R$^4$—R$^5$:
    a 1,2-, 1,3-, 1,4 or 1,5-diamino (2C-8C)alkane;
    a diamino (3C-8C)cycloalkane;
    a di(aminomethyl) (3C-8C)cycloalkane;
    a di(aminomethyl)heteroalicyclic;
    a di(nitrogen heteroaromatic); and,
    a methylene [di(nitrogen heteroaromatic)]
R$^8$ is the same as R$^4$;
R$^9$ is the same as R$^5$;
R$^{10}$ is the same as R$^6$;
R$^{10}$ is the same as R$^7$;
each Pt is independently in a +2 or a +4 oxidation state:
  wherein:
    when any Pt is in the +2 oxidation state (Pt(II)), R$^6$, R$^7$, R$^{10}$ and R$^{11}$ do not exist with regard to that Pt;
    when any Pt is in the +4 oxidation state (Pt(IV)), R$^6$, R$^7$, R$^{10}$ and R$^{11}$ are independently selected from the group consisting of NH$_3$, H$_2$O, Cl and -(1C-6C)C(O)— with regard to that Pt;
n is 0-50; and,
m is 0 to 400% of r,
  provided that each of the "n" amino acids in [amino acids]$_n$, can be chleated to only one Pt complex.

In an aspect of this invention, in the above polymer: all Pt atoms are in the +2 oxidation state; and, together, R$^4$—R$^5$ and R$^8$—R$^9$ are:

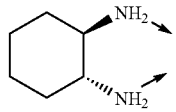

In an aspect of this invention, in the above polymer s is 5-250 kDa.
In an aspect of this invention, in the above polymer s is 5-60 kDA.
In an aspect of this invention, in the above polymer R$^1$ and R$^2$ are —CH$_3$; and R$^3$ is —NHCH$_2$CH(OH)CH$_3$.
In an aspect of this invention, in the above polymer:
q is approximately 90%;
r is 100-q;
m is 0%;
n is 1;
[amino acids] is G;
X is a covalent bond; and,
t is 0 or 1.

In an aspect of this invention, in the above polymer:
q is approximately 90%;
r is 100-q;
m is 0%;
n is 2;
(amino acids) is GG;
X is a covalent bond; and,
t is 0 or 1.

In an aspect of this invention, in the above polymer:
q is approximately 90%;
r is 100-q;
m is 0%;
n is 3;
(amino acids) is GGG;
X is a covalent bond; and,
t is 0 or 1.

In an aspect of this invention, in the above polymer:
q is approximately 90%;
r is 100-q;
m is 0%;
n is 4;
(amino acids) is GGGG (Seq. ID No. 1);
X is a covalent bond; and,
t is 0 or 1.

In an aspect of this invention, in the above polymer:
q is approximately 90%;
r is 100-q;
m is 0%;
n is 4;
(amino acids) is GFLG (Seq. ID No. 2);
X is a covalent bond; and,
t is 0 or 1.

In an aspect of this invention, in the above polymer:
q is approximately 90%;
r is 100-q;
m is 0%;
n is 4;
(amino acids) is GFLG;
X is —NH(CH$_2$)$_v$SO$_2$—;
v is 3; and,
t is 0 or 1.

In an aspect of this invention, in the above polymer:
q is approximately 90%;

r is 100-q;
m is 0%;
n is 2;
(amino acids) is GG;
X is —NH(CH$_2$)$_v$SO$_2$—;
v is 3; and,
t is 0 or 1.

In an aspect of this invention, in the above polymer:
q is approximately 90%;
r is 100-q;
m is 0%
n is 3;
X is a covalent bond;
(amino acids) is GGG; and,
t is 0 or 1.

In an aspect of this invention, in the above polymer:
q is approximately 90%;
r is 100-q;
m is 1 to 100%;
n is 3;
X is a covalent bond;
(amino acids) is GGG; and,
t is 0 or 1.

In an aspect of this invention, in the above polymer:
q is approximately 90%;
r is 100-q;
m is 1 to 100%;
n is 4;
X is a covalent bond;
(amino acids) is GGGG; and,
T is 0 or 1.

In an aspect of this invention, in the above polymer:
q is approximately 90%;
r is 100-q;
m is 1 to 100%;
n is 4;
X is a covalent bond;
(amino acids) is GFLG; and,
t is 0 or 1.

In an aspect of this invention, in the above polymer m is from 1-100%.

An aspect of this invention is a method for the treatment of a solid tumor cancer comprising administering to a patient in need thereof a therapeutically effective amount of a compound of this invention.

An aspect of this invention is a pharmaceutical composition comprising:
a compound of this invention; and,
one or more pharmaceutically acceptable excipients.

An aspect of this invention is a compound having the chemical formula:

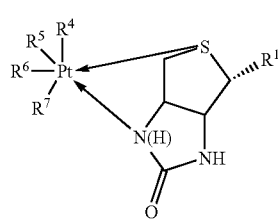

wherein R$^1$, R$^4$, R$^5$, R$^6$ and R$^7$ are as described above.

An aspect of this invention is a compound having the chemical structure:

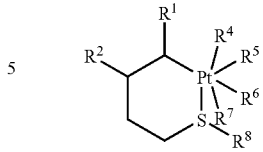

wherein R$^3$, R$^4$, R$^5$, R$^6$ and R$^7$ are as described above;
R$^8$ is (1C-6C)alkyl;
R$^2$ is as described above, except that R$^2$ cannot be =O; and,
R$^9$ is as described above except that R$^9$ cannot be -(linker)-R$^{10}$.

DETAILED DESCRIPTION OF THE INVENTION

Brief Description of the Tables
Table 1 shows the amount of small Pt molecule released as a function of linker length and stable chelate structure.
Table 2 is a comparison of the efficacy of representative compounds of this invention versus carboplatin. In the table, TGI stands for tumor growth inhibition and BWL stands for body weight loss.
Table 3 is a compilation of data demonstrating that representative compounds of this invention contain additional Pt complexes on the linker intermediate between the terminal Pt complex and the point of attachment of the linker to the polymeric backbone.

BRIEF DESCRIPTION OF THE FIGURES

FIG. 15 is Table 2.

DEFINITIONS

Figure 1:
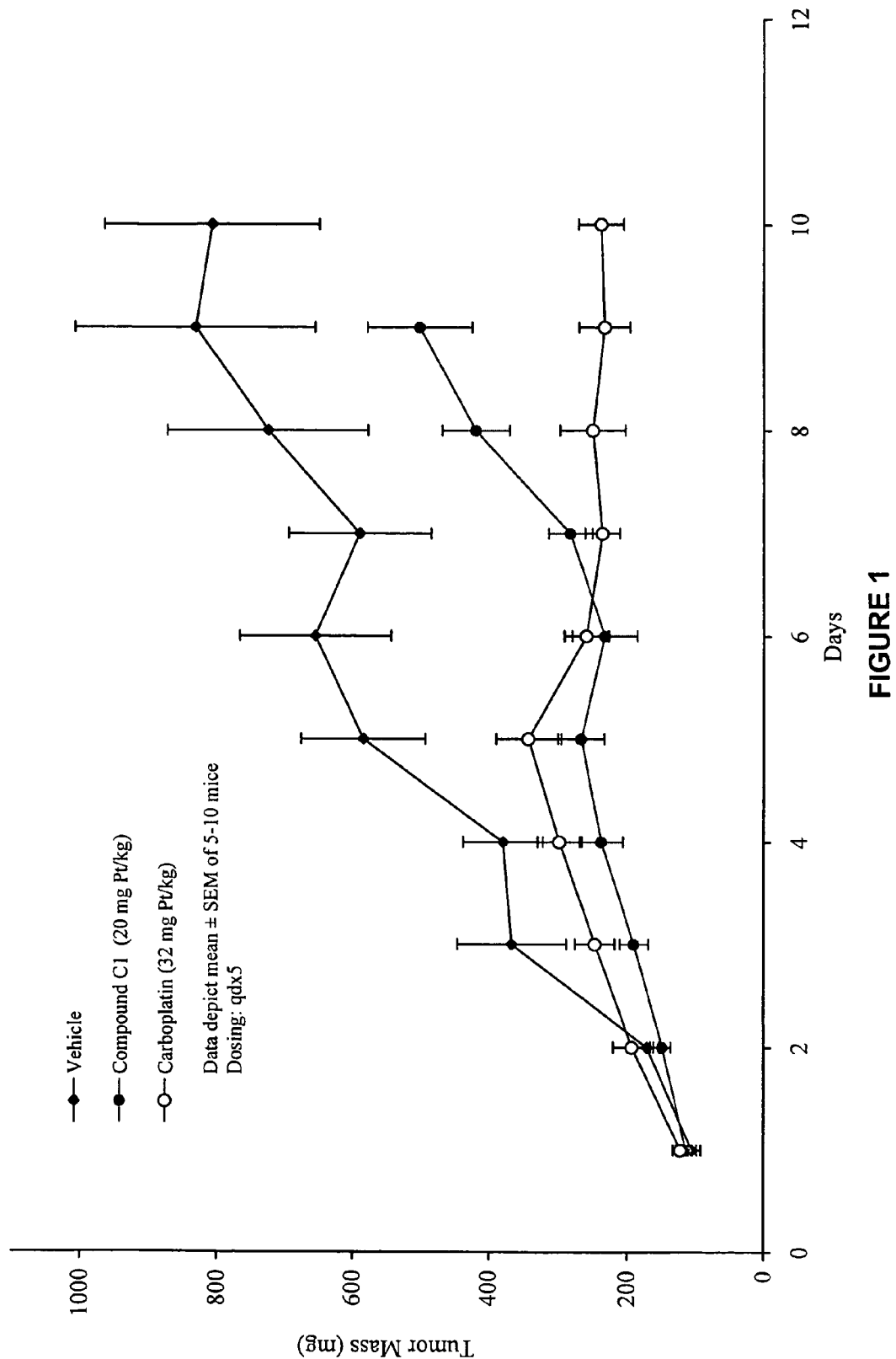
FIG. 1 is a graphical comparison of tumor growth inhibition of compound C1 versus a control and carboplatin.
Figure 2:
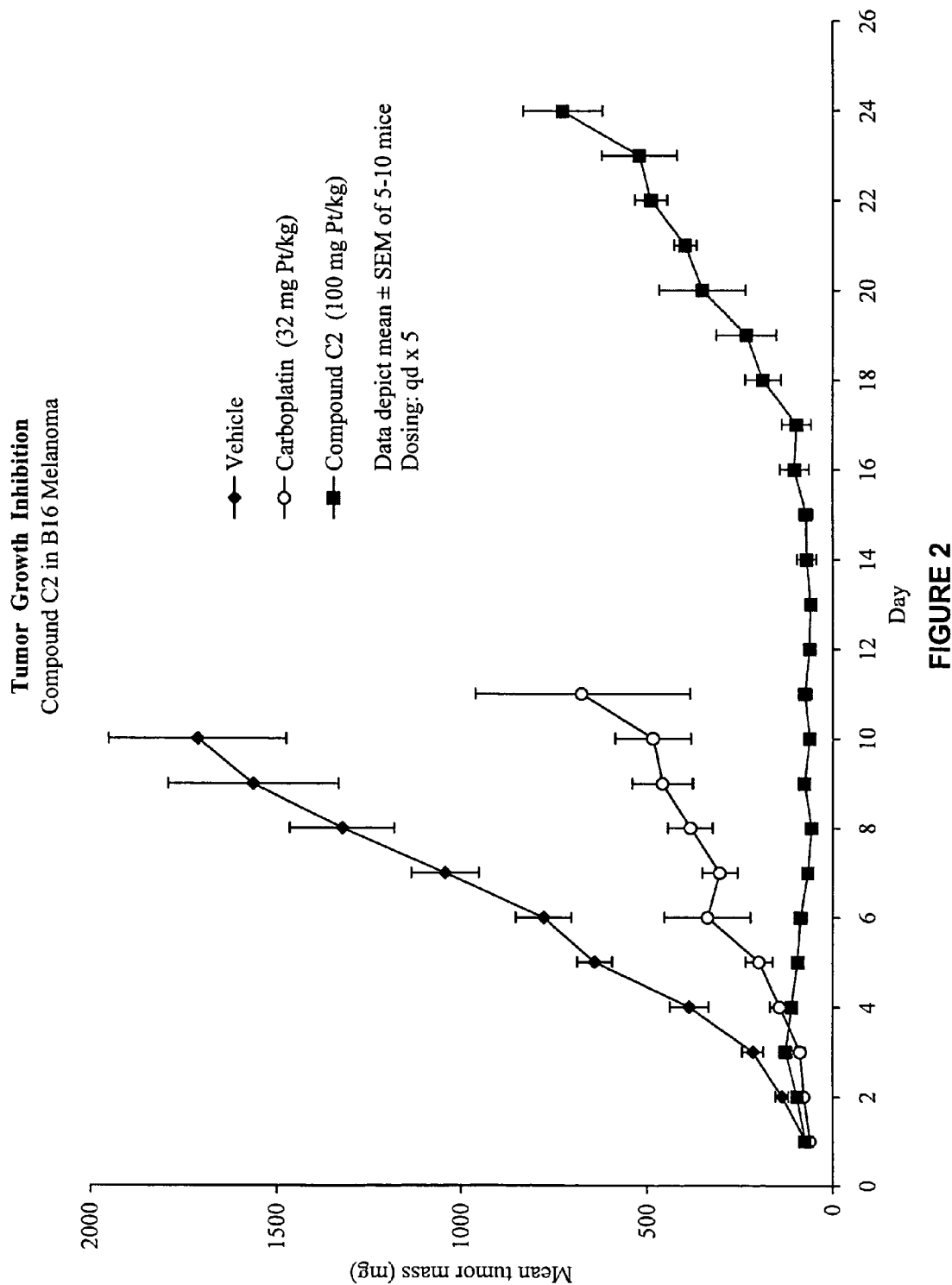
FIG. 2 is a graphical comparison of tumor growth inhibition of compound C2 of this invention versus a control and carboplatin.
Figure 3:
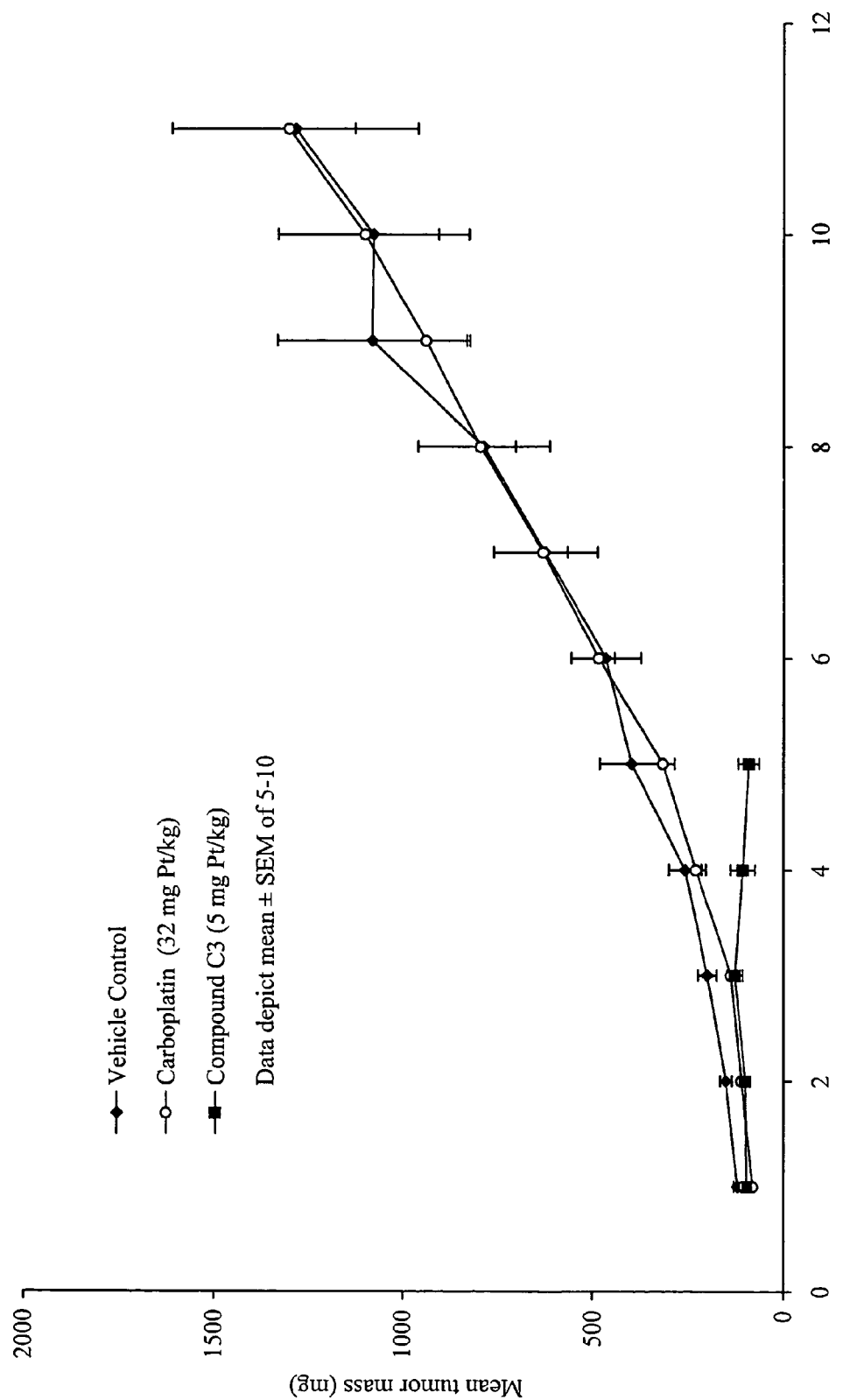
FIG. 3 is a graphical comparison of tumor growth inhibition of compound C3 of this invention versus a control and carboplatin.
Figure 4:
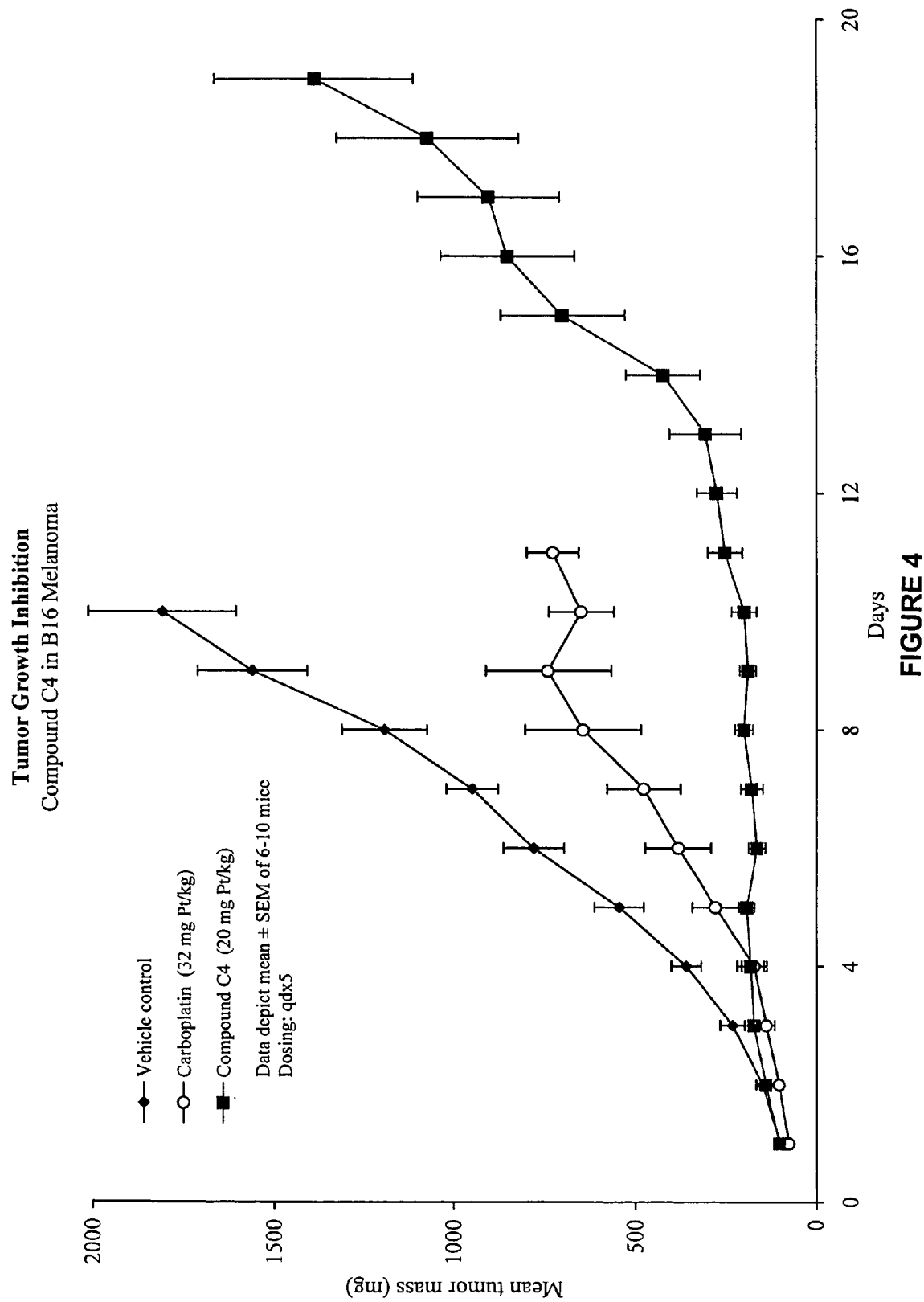
FIG. 4 is a graphical comparison of tumor growth inhibition of compound C4 of this invention versus a control and carboplatin.
Figure 5:
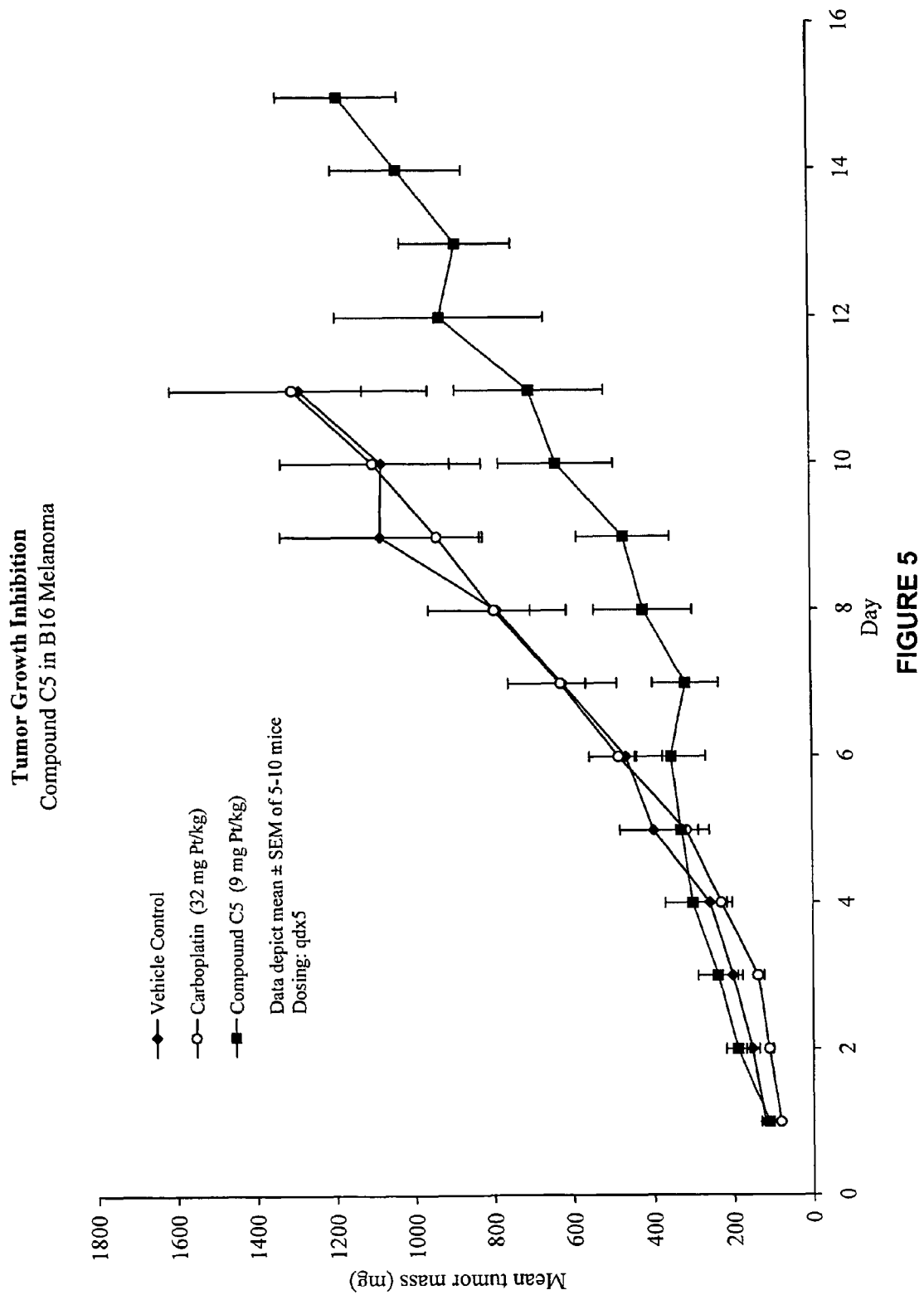
FIG. 5 is a graphical comparison of tumor growth inhibition of compound C5 of this invention versus a control and carboplatin.
Figure 6:
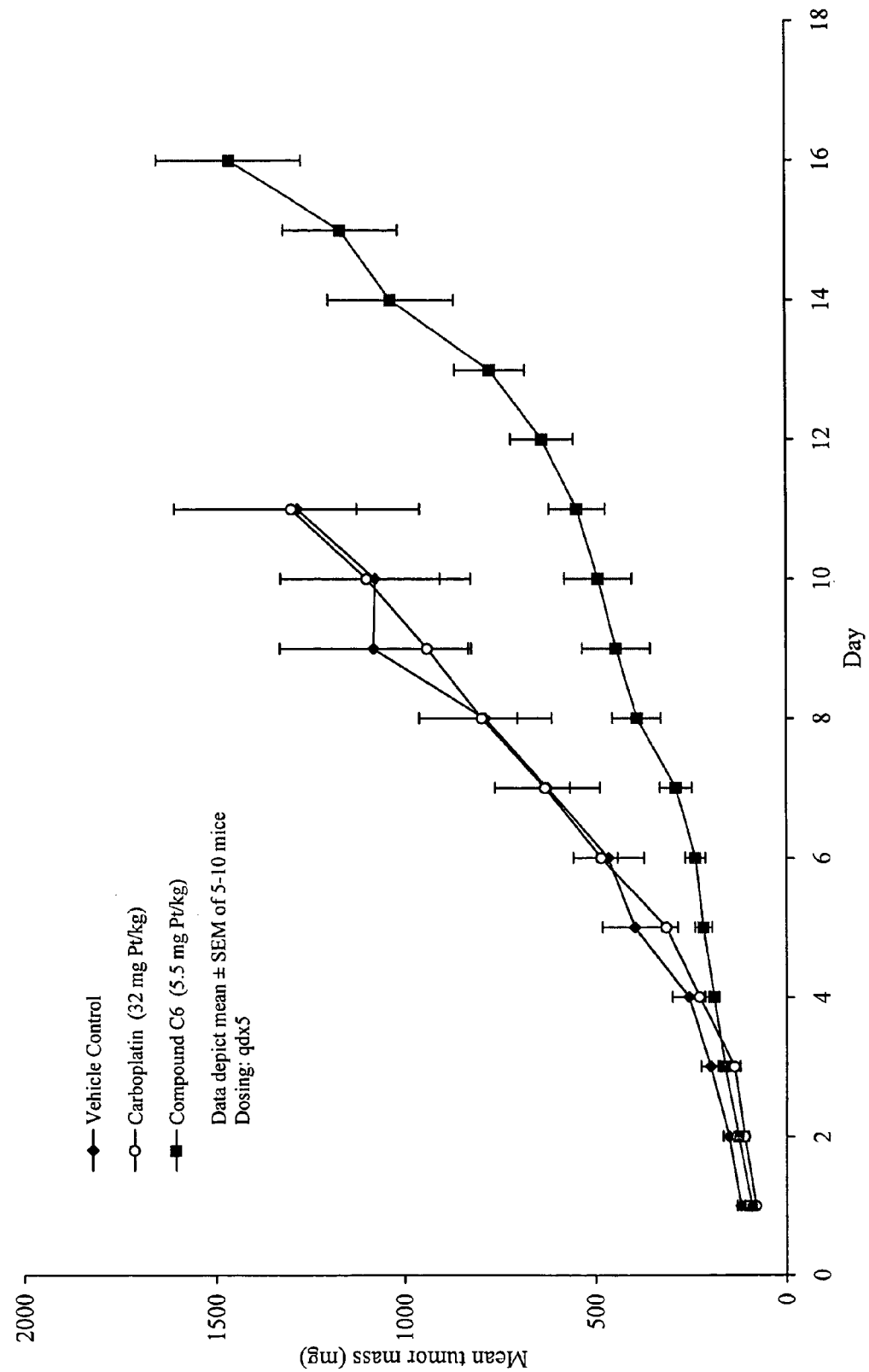
FIG. 6 is a graphical comparison of tumor growth inhibition of compound C6 this invention versus a control and carboplatin.
Figure 7:
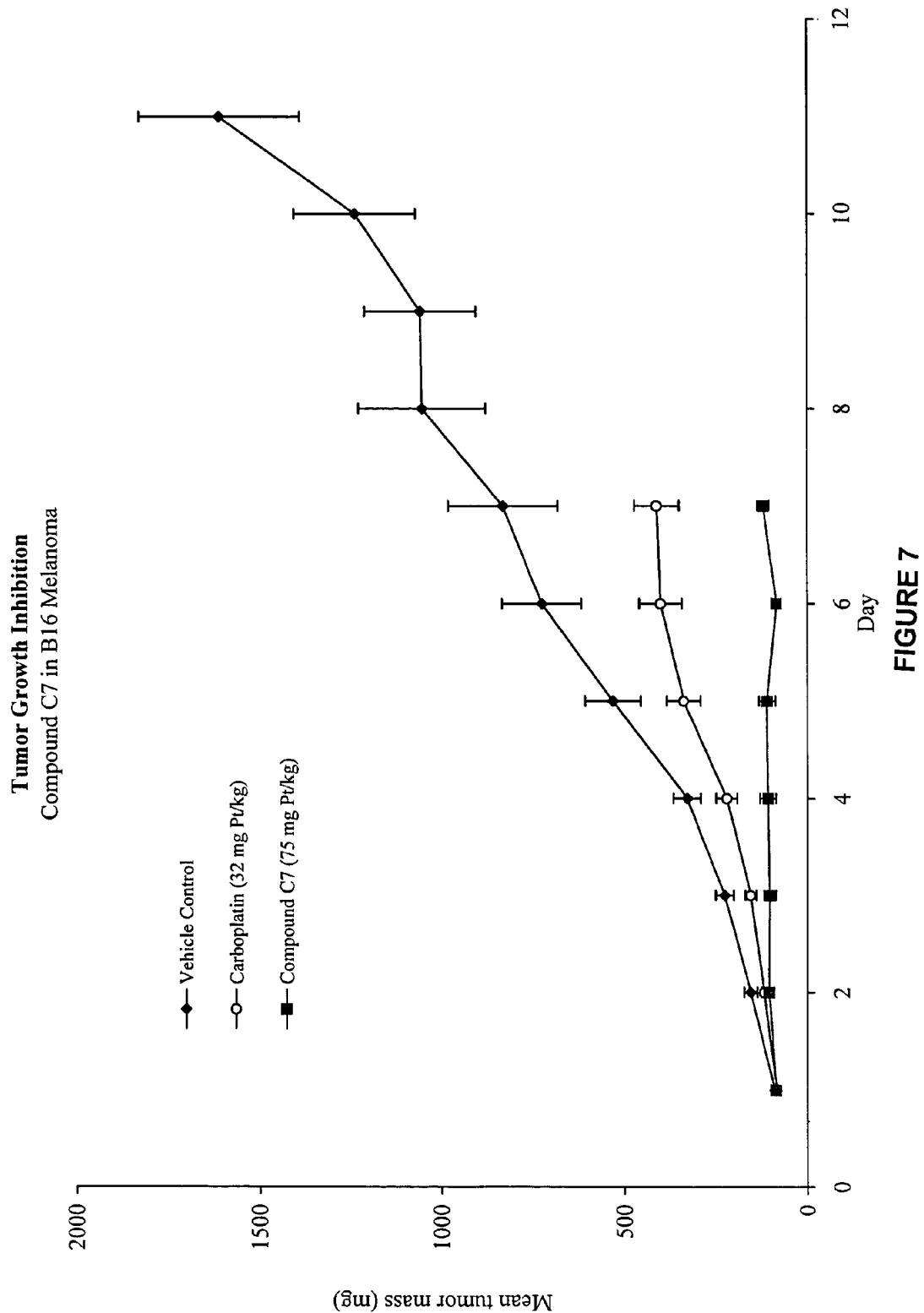
FIG. 7 is a graphical comparison of tumor growth inhibition of compound C7 of this invention versus a control and carboplatin.
Figure 8:
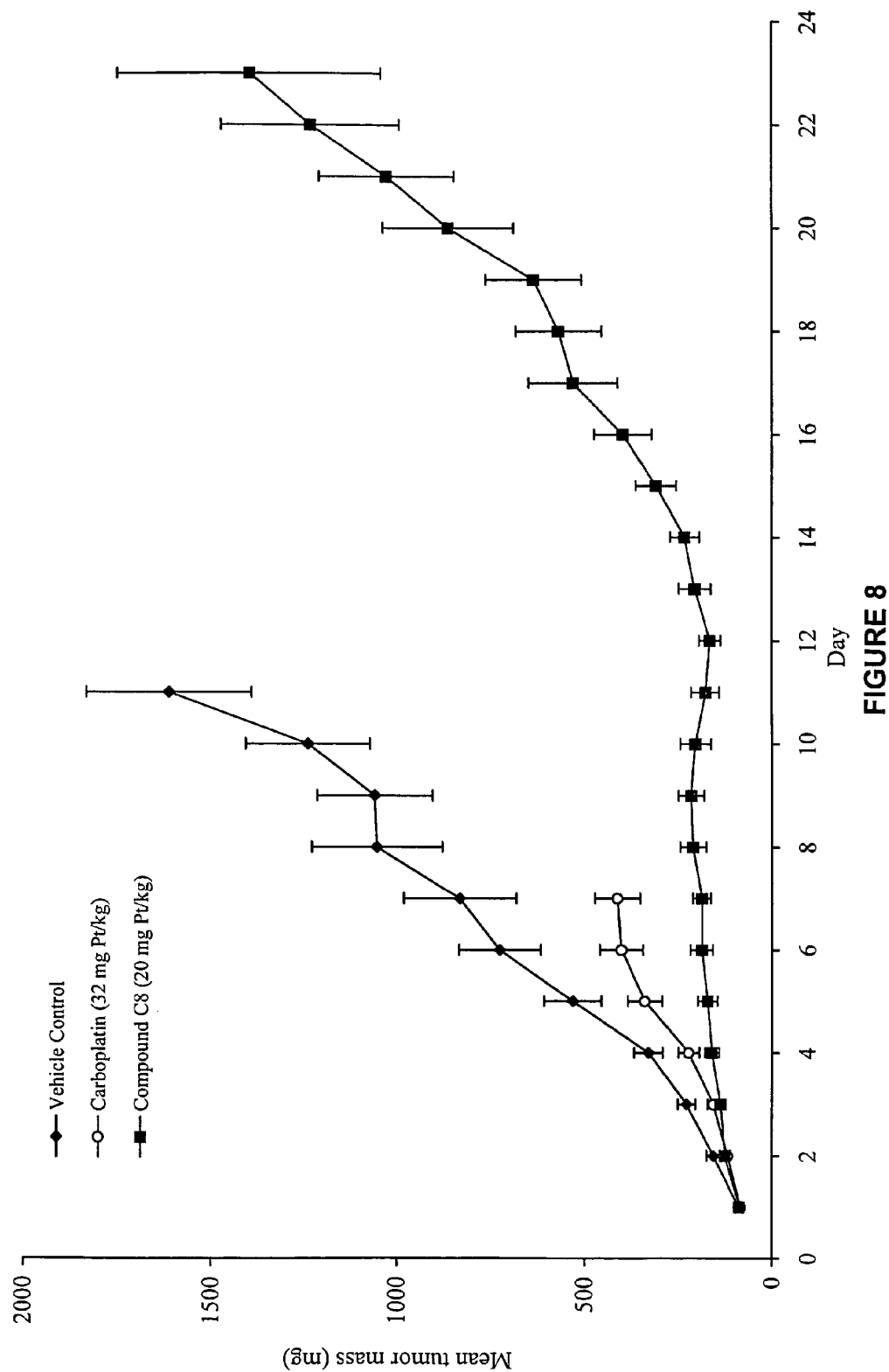
FIG. 8 is a graphical comparison of tumor growth inhibition of compound C8 of this invention versus a control and carboplatin.
Figure 9:
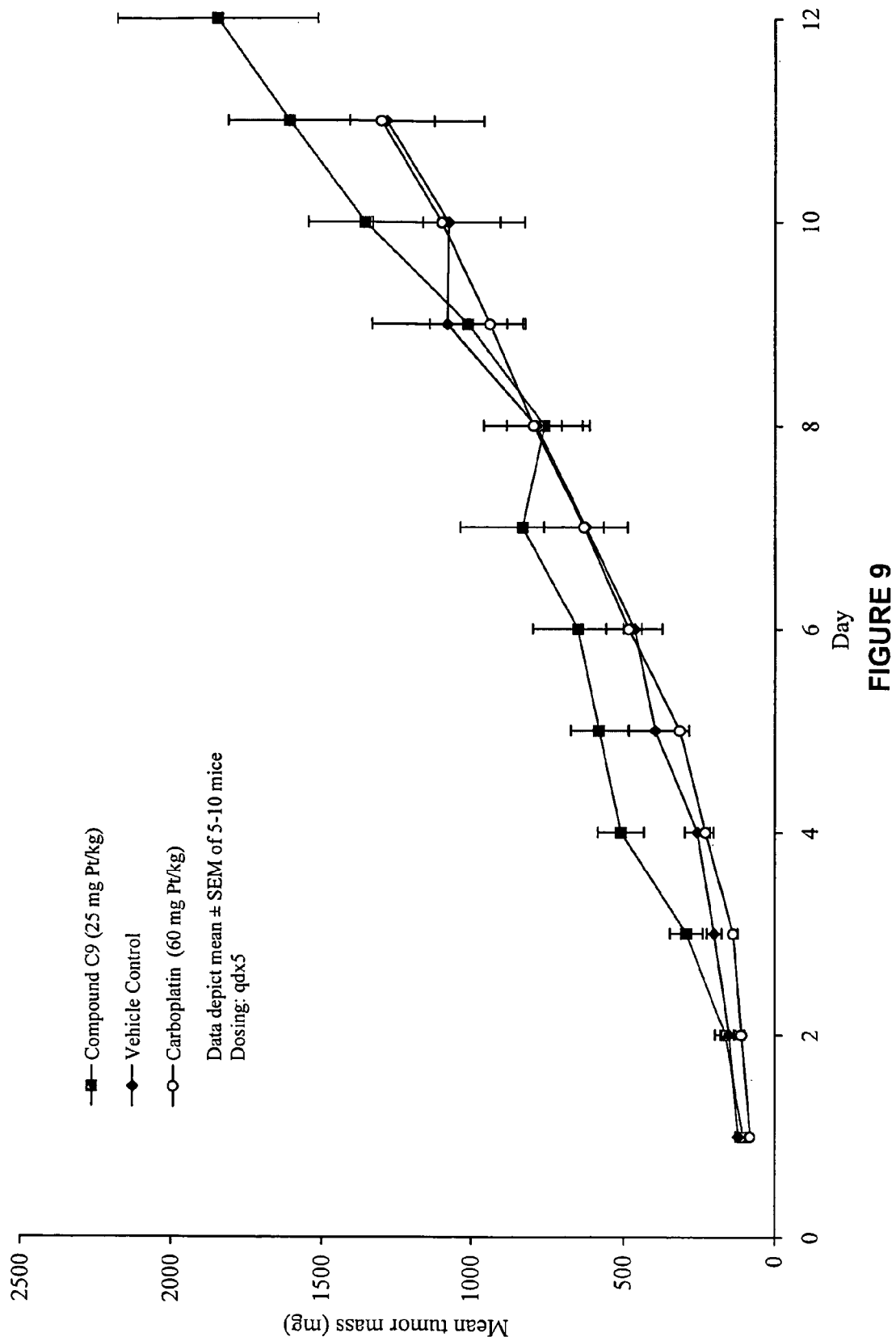
FIG. 9 is a graphical comparison of tumor growth inhibition of compound C9 of this invention versus a control and carboplatin.
Figure 10:
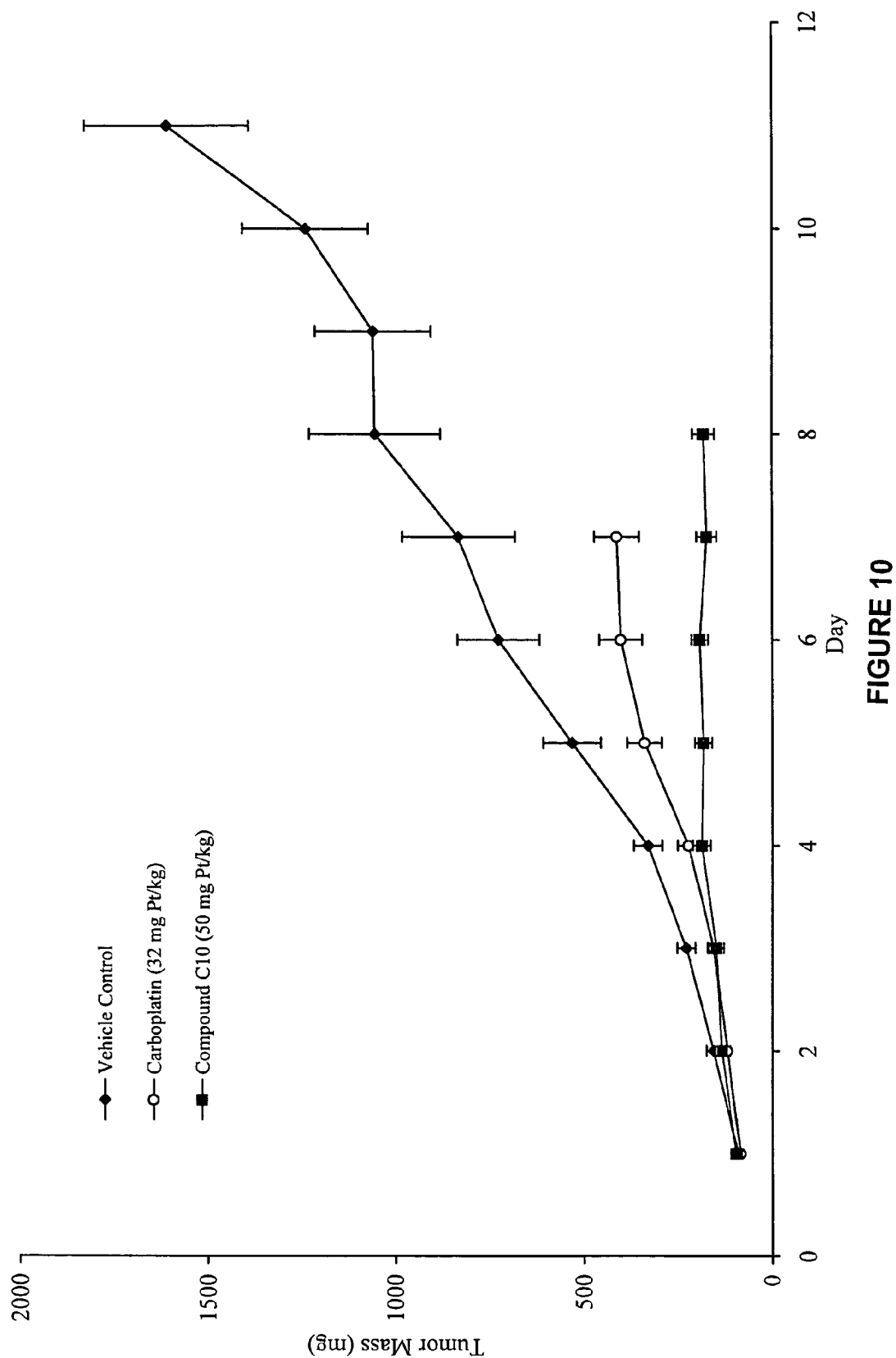
FIG. 10 is a graphical comparison of tumor growth inhibition of compound C10 of this invention versus a control and carboplatin.
Figure 11:
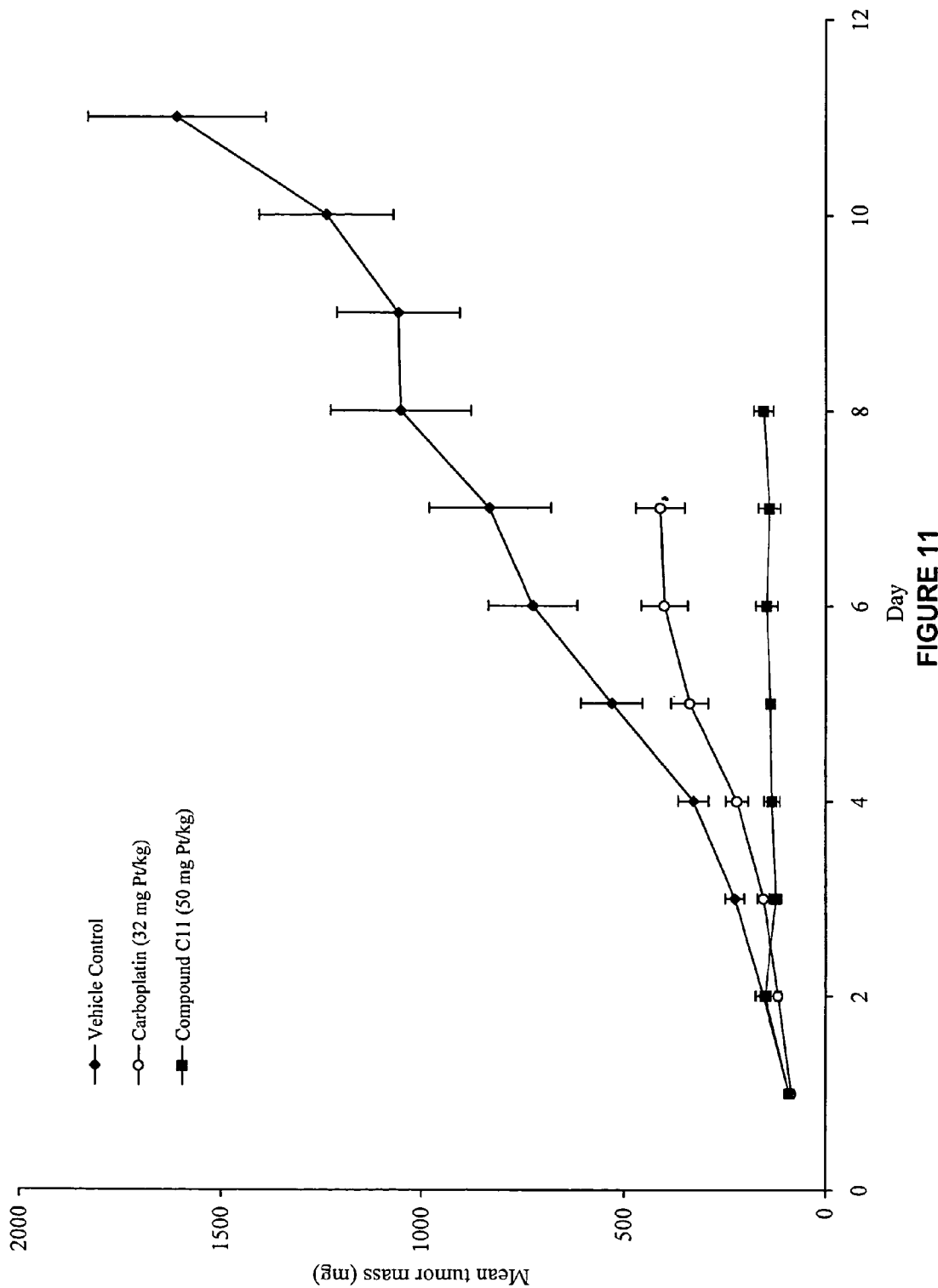
FIG. 11 is a graphical comparison of tumor growth inhibition of compound C11 of this invention versus a control and carboplatin.
Figure 12:
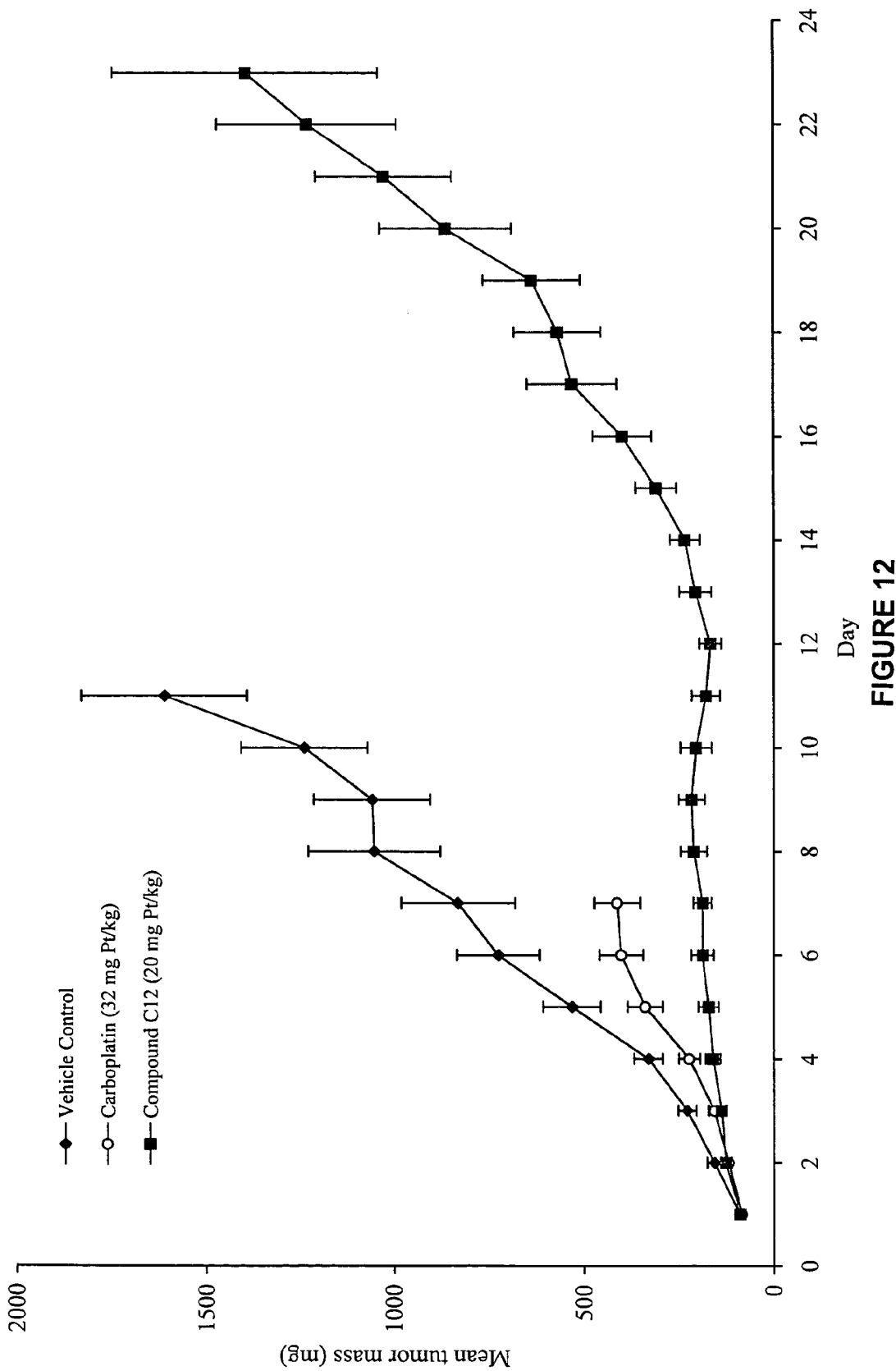
FIG. 12 is a graphical comparison of tumor growth inhibition of compound C12 of this invention versus a control and carboplatin.
Figure 13:
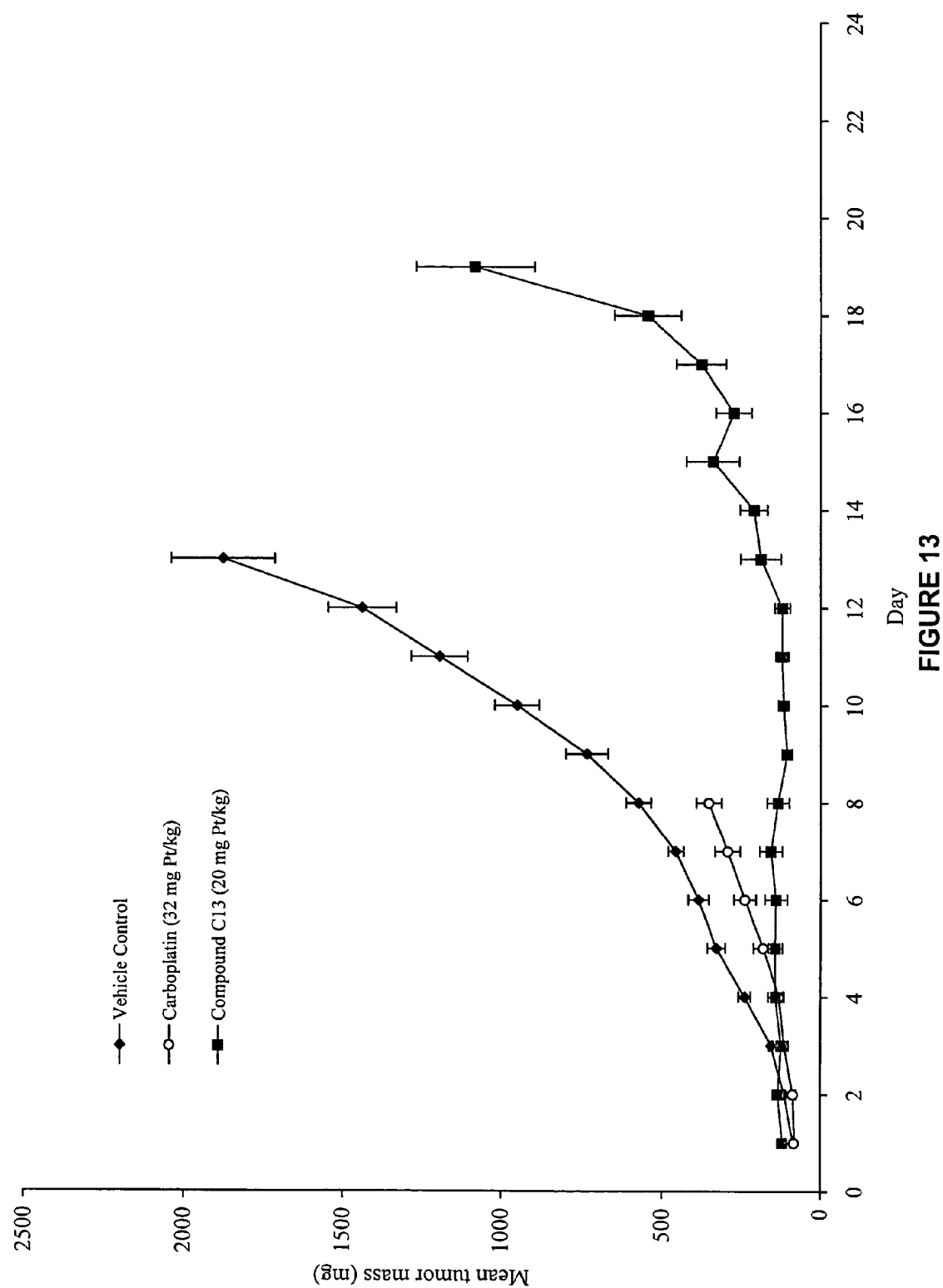
FIG. 13 is a graphical comparison of tumor growth inhibition of compound C13 of this invention versus a control and carboplatin.

As used herein, "alkyl" refers to a saturated (containing no multiple carbon-carbon bonds) aliphatic (containing no fully delocalized π-electron system), hydrocarbon containing, if otherwise unsubstituted, only carbon and hydrogen atoms. The designation ($n_1C$-$n_2C$)alkyl, wherein $n_1$ and $n_2$ are integers from one to 6, refers to straight or branched chain alkyl groups comprising from $n_0$ to and including $n_2$ carbon atoms. An alkyl group herein may be optionally substituted with one or more entities selected from the group consisting of halo, hydroxy, alkoxy, aryloxy, carbonyl, nitro, cyano, carboxyl and alkoxycarbonyl.

A "linker" refers to a group that spatially separates the Ama=Pt chelate from the polymeric backbone. The linker can be any sort of entity, such as, without limitation, a polyethylene glycol, an aminoacid or a polyaminoacid, one end of which is capable of forming a covalent bond with the polymer backbone and the other end of which is capable of forming a covalent bond with a platinum chelated end group.

In the structural features described herein as [amino acids]$_a$ or [amino acids]$_n$, [amino acids] refers to a (linker) entity comprised of amino acids. The "a" or "n" refers to the actual number of amino acids, i.e., 1, 2, 4 . . . etc., that comprise the [amino acids] linker. An amino acid is a compound that has in its chemical composition, a free amine, i.e. —$NH_2$, group and elsewhere in its structure a carboxyl, —COOH, group (depending on the milieu the amino acid finds itself in, the amine may exist as —$NH_3^+$ and the carboxyl as —$COO^-$, that is, the compound is a zwitterion). The use of the plural in (amino acids) is intended to convey the fact that, when "a" or "n" is 2 or more, that is the [amino acids] linker is comprised of two or more amino acids, each amino acid may be the same as, or different than, each other amino acid. For, example, without limitation, if a or n is 4, then [amino acids] consists of 4 individual amino acids, which may be the same or different. The amino acids are bonded to one another through peptide linkages; that is, recurring amide bonds:

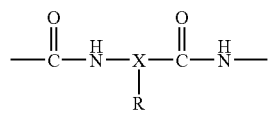

wherein X is a group such as, without limitation, (1C-20C) alkyl (e.g., if X is $CH_2$, then the amino acid is an α-amino acid), cycloalkyl, aryl, heteroaryl or heteroalicyclic. R can be any group known to those skilled in the art to be compatible with starting amino acids. It is understood that in the structure -(linker)-$R^{10}$ where (linker) is [amino acids] and $R^{10}$ is a backbone polymer, the $R^{10}$ may be at either end of the amino acid chain. That is, $R^{10}$ may be covalently bonded to the NH at one end of the peptide chain or to the C=O carbon at the other end. In some cases, either orientation is chemically feasible; in such cases both orientations are within the scope of this invention. In other cases, e.g., when Z is C=O, then the [amino acids] group will be in the orientation in which its NH group is bonded to the C=O carbon. It will be apparent to those skilled in the art which orientation(s) the [amino acids] linker may assume in a particular molecule based on the disclosures herein.

It is further understood that, for each iteration of the above peptide bond, X and R may be the same as or different than any other X or R in the chain; i.e., as noted above, the amino acids may be the same or different. The individual amino acids may be natural or synthetic. The natural amino acids include alanine (Ala, A), arginine (Arg, R), asparagines (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (The, T), tryptophan (Trp, W), tyrosine (Try, Y) and valine (Val, V). A poly(amino acids) group comprised of entirely natural amino acids is also know as an oligopeptide (for shorter chain length) or polypeptide (longer chains). While the truly "naturally-occurring" amino acids have "L" absolute stereochemistry the "L" form, the "D" form and the racemate (50:50 mixture of the two forms) will be considered "natural" amino acids for the purposes of this invention. Any of these may be used alone, in combination with other natural amino acids or in combination with synthetic amino acids, to form the -(amino acids)$_a$-group. Synthetic amino acids useful in this aspect of this invention include any compound with a basic —$NH_2$ group within 1-20 carbon atoms of a —C(O)OH group.

As used herein, a "backbone polymer" refers a scaffold structure formed by the repetitive reaction (polymerization) of one or more monomers, which are small molecule structural units from which the polymer is constructed. The scaffold, when formed, includes pendent groups (i.e., groups that were bonded to and part of the monomer(s)) that can react with terminal functional groups of linkers that themselves are, or can be, further substituted with various entities identified herein to form compounds of this invention. Such entities include, but are not limited to, water-solubilizing groups, tumor-seeking groups, MRI contrast agents, radioactive groups (for imaging or treatment) and/or non-platinum chemotherapeutics to be used in conjunction with the platinum complexes of this invention. A "natural" backbone polymer refers to polymers that can be found in nature such as, without limitation, polysaccharides, polypeptides, cellulose, collagen, lignins, xanthans, gelatin alginates, albumin, glycosamine glycans, celluloses, heparin, chondroitin 6-sulfate, hyaluronic acid, glycosaminoglycans (GAGs), dennatan sulfate, keratan sulfate, chitin, chitosan, dextran and dextrin.

Synthetic polymers useful with this invention include, without limitation, acrylic polymers, alkyd resins, aminoplasts, coumarone-indene resins, epoxy resins, fluoropolymers, phenolic resins, polyacetals, polyacylics, polyalkenylenes, polyalkenes, polyalkynylenes, polyamic acids, polyamines, polyimides, polyamides, polyanhydrides, polyarylenealkenylenes, polyarylenealkylenes, polyarylenes, polyazomethines, polybenzimidazoles, polybenzothiazoles, polybenzoxazinones, polybenzyls, polycarbodiimides, polycarbonates, polycarboranes, polycarbosilanes, polycyanurates, polydienes, polyester-polyurethanes, polyesters, polyetheretherketones, polyether-polyurethanes, polyethers, polyhydrazides, polyimidazoles, polyimides, polyimines, polyisocyanurates, polyketones, polyolefins, polyoxadiazoles, polyoxides, polyoxyalkylenes, polyoxyarylenes, polyoxymethylenes, polyoxyphenylenes, polyphenyls, polyphosphazenes, polypyrroles, polypyrrones, polyquinolines, polyquinoxalines, polysilanes, polysilazanes, polysiloxanes, polysilsequioxanes, polysulfides, polysulfonamides, polysulfones, polythiazoles, polythioalkylenes, polythioarylenes, polythioethers, polythiomethylenes, polythiphenylenes, polyureas, polyurethanes, polyvinyl acetals, polyvinyl butyrals, polyvinyl formals, vinyl polymers, PEG-based star molecules and dendrimers.

Semi-synthetic polymers are natural polymers that have been chemically modified to give them certain desirable characteristics. Examples of semi-synthetic polymers include, without limitation, hydroxypropylcellulose and carboxymethylcellulose, derived polypeptides.

Presently preferred backbone polymers include polyacrylate, polymethacrylate, polyacrylamide, poly(methacrylamide), poly(hydroxyethylacrylate), poly(hydroxyethylmethacryate), poly(hydroxyethylacrylamide), poly(hydroxyethylmethylacrylamide), poly(2-hydroxypropylmethacrylamide), poly(ethylene glycol), poly(aspartic acid), polyurethane, polyester, polyamide, polyglutamic acid, polypeptide, PEG star molecules, polysaccharide, dendrimer; ethylenediamine core poly(amidoamine) dendrimer, glycosamine glycan, carboxymethyl cellulose, hydroxypropyl cellulose, dextran, dextrin or a random or block copolymer of any two, three or four of the above. As used herein, a "copolymer" refers to a polymer made by polymerization of two or more different monomers. "Different monomers" refers both to basic monomeric differences, for example, without limitation, the formation of a polymer using acrylamide and methacrylamide, and to polymers formed from the same backbone polymer, for example, again without limitation, methyacrylamide, wherein the pendent nitrogen is substituted with different groups, some being substituted with, for example without limitation, N-(2-hydroxypropyl) groups and others with oligopeptide groups. A "random" copolymer refers to a polymer in which two or more monomers obey Bernoullian distribution in their arrangement in the completed polymer; e.g., AABCACCAB-BACBCB, etc. A "block" copolymer refers to a polymer in which two or more monomers are present in homogeneous sequences in the completed polymer; i.e., AAA-BBB-CCC-DDD, etc.

A polymer backbone of this invention has an average molecular weight distribution, as determined by size exclusion chromatgrapy (see Example 28), of from 1 to 500 kDa, presently preferably from 5 to 250 kDa and, presently more preferably, from 5 to 60 kDa.

As used herein, "halo" or "halogen" refers to fluorine (F), chlorine (Cl), bromine (Br) and iodine (1).

As used herein, "ammine" refers to ammonia, $NH_3$.

As used herein, a primary, secondary or tertiary alkyl amine refers to an $RNH_2$, an RR"NH or an RR'R" N group, wherein R, R' and R" independently represent, without limitation, alkyl, cycloalkyl, aryl, heteroaryl and heteroalicyclic moieties.

As used herein, "cycloalkyl" refers to an all-carbon cyclic or fused multicyclic ring, which, although it may contain one or more double bonds, maintains an essentially aliphatic character; that is, any double bonds present do not interact to form a delocalized π-electron system in the ring. For purposes of this invention, the ring may contain up to 8 carbon atoms. The designation $(n_1C-n_2C)$cycloalkyl refers to $n_1$ up to and including $n_2$ carbon atoms in the ring. As used herein, "fused" means that two cycloalkyl groups share at least one ring atom between them. Compounds such as spiro[4.4]nonane is considered "fused" for the purposes of this invention. More commonly, fused rings share two adjacent carbon atoms. An example of such a fused system is decalin. A "cycloalkylamine" refers to a cycloalkyl group substituted directly on the ring with an $-NH_2$ group. A cycloalkyl group may optionally be substituted with one or more groups selected from the group consisting of halo, hydroxy, alkoxy, aryloxy, carbonyl, nitro, cyano, carboxyl and alkoxycarbonyl.

As used herein, "aryl" or "aromatic" refers to an all-carbon 6-member ring (benzene, phenyl) or two or more fused 6-member rings (naphthylene, naphthyl) wherein "fused" means that the rings share two adjacent ring carbon atoms. The ring or ring system has a rr-electron system that is fully delocalized around the ring(s). An "arylamine" refers to an aryl group substituted with one or two $-NH_2$ groups. If one $-NH_2$ group is present, the compound is generally referred to as an aniline. If two $-NH_2$ are present, the compound is also referred to as a phenylenediamine. The arylamine may optionally be substituted with one or more additional entities selected from the group consisting of halo, hydroxy, alkoxy, aryloxy, carbonyl, nitro, cyano, carboxyl and alkoxycarbonyl.

As used herein, "heteroaryl" refers to a 5-member or 6-member ring or to two rings; i.e., two 5-member, two six-member or a 5- and a 6-member ring that are "fused," meaning they share two adjacent carbon atoms. The ring or fused ring system has a delocalized π-electron system. A "nitrogen heteroaryl" refers to a heteroaryl that contains at least one nitrogen in the ring. If the ring is a six-member ring, nitrogen is the only non-carbon atom that may be in the ring. If the ring is a 5-member ring, it may contain 1, 2, 3 or 4 nitrogen atoms and, optionally one oxygen or one sulfur atom. A nitrogen heteroaryl may be optionally substituted with one or more entities selected from the group consisting of halo, hydroxy, alkoxy, aryloxy, carbonyl, nitro, cyano, carboxyl and alkoxycarbonyl.

As used herein, "heteroalicyclic" refers to a cyclic or fused cyclic ring system that contains atoms other than carbon and that does not have a delocalized π-electron system in the ring. "Fused" means the same as stated above. A "nitrogen heteroalicyclic" refers to a heteroalicyclic having at least one nitrogen atom in the ring system. An "aminomethyl nitrogen heteroalicyclic" refers to a nitrogen heteroalicyclic that is substituted with an $-CH_2NH_2$ group. A heteroalicyclic may be optionally substituted with one or more entities selected from the group consisting of halo, hydroxy, alkoxy, mercapto, aryloxy, carbonyl, nitro, cyano, carboxyl and alkoxycarbonyl.

As used herein, "di(nitrogen hetearyl)" refers to two nitrogen heteroaryls that are joined by a single covalent bond between them. Examples, without limitation, of di(nitrogen heteoaryl) groups include:

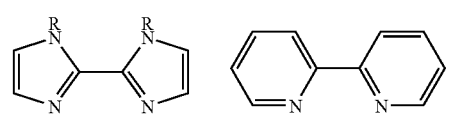

As used herein, "methylene di(nitrogen heteroaryl)" refers to two nitrogen heteroaryls each bonded by a single covalent bond to the same carbon atom (the methylene carbon). The methylene carbon may be further substituted with, for example, without limitation, an $-OH$ group. Examples, without limitation, of methylene di(nitrogen heteroaryl) groups include:

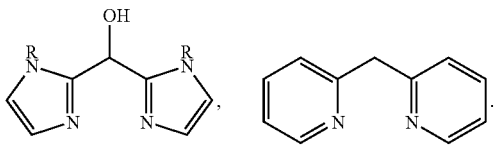

As used herein, a Pt complex" refers to a chemical compound in which a Pt atom is coordinated with 4, if Pt(II), or with 6, if Pt(IV), ligands.

As used herein, a "chelate" refers to a bidentate ligand that forms a ring with the Pt atom of a Pt complex.

As used herein a "tumor-seeking" group refers to an entity that is know to preferentially seek out and bond to surface structures on neoplastic cells that do not occur or are expressed to a substantially lesser degree by normal cells or entitles that preferentially accumulate in tumors over normal tissue. Tumor-seeking entities include, without limitation, monoclonal antibodies, antibody fragments, peptides, steroids, somatosin analogs, lectins, folic acid, its derivatives and analogs, vitamin B12, biotin, porphyrin, essential fatty acids, bioreductive molecules and polyanionic polysaccharides.

As used herein, "water-solubilizing" refers to a group that either improves the water solubility of a polymer herein or that confers water solubility on an otherwise insoluble polymer. Water-solubilizing groups useful with this invention include, without limitation, 2-hydroxyethyl, 2-hydroxypropyl, 2,3-dihydroxypropyl, 3-hydroxypropyl, poly(ethylene glycol) and (1C-6C)alkyl groups terminating in $SO_3$, sulfonato, quaternary ammonium or carboxy.

When designating the composition of a copolymer herein, a percentage (%) refers to the actual number of a particular monomer in the average polymeric molecule of that copolymer. For example, in a co-polymer of formula $(A_p/B_q/C_r)$ comprising 100 total monomers (in the average polymer chain) where "p" is defined as being from 0 to 25%, "q" as being from 5 to 50% and "r" as being from 50 to 95%, what is meant is that, of the 100 monomers in the average polymer strand, up to 25 are monomer A, up to 50 are monomer B and up to 95 are monomer C. It is understood that the term monomer includes the polymeric subunit derived from that monomer. That is, the "A" in $A_p$ is not a monomer per se but, rather, is a polymeric subunit based on a corresponding monomer. For example, without limitation, the polymeric subunit —$CH_2CH(CH_3)C(O)NH$— is derived from the monomer methylmethacrylamide, $CH_2$=$C(CH_3)C(O)NH_2$. Of course, in all cases, p+q+r=100%. The phrase "m is from 0 to 90% of r" means that a Pt complex modified by "m" in the chemical structure is present in from 1 to 90% of the monomer modified by r. For instance, if "r" is 70% and "m" is 90%, then a Pt complex is appended to 90% of the monomer fragment comprising 70% of the average polymer chain or 63% (90×70) of the total monomers comprising the polymer.

The following formulaic approach is used herein to describe the polymeric compounds of this invention: (polymer backbone)-(linker)-(leaving chelating group)=Pt=(stable chelating group), wherein the "=" indicates two single covalent or coordinate covalent bonds between the Pt and the attached group. An example, without limitation, is the compound p(HMPA)-GGG-Ama=Pt=DACH. p(HMPA) is the backbone polymer, poly(N-(2-hydroxypropyl)methylacrylamide-co-methacrylamide), GGG is the linker gly-gyl-gyl-, and Ama is the leaving Pt chelating group, amidomalonate, which is chelated to Pt by two coordinate covalent bonds. The Pt is also coordinated by two single bonds to a stable ligand, DACH (1R, 2R-diaminocyclohexane). Another example is the compound of formula p(HMPA)-GFLG-3C-Sulf-Asp=Pt=DACH where p(HMPA) is again the backbone polymer, GFLG-C3-Sulf is the linker, -gly-phe-leu-gly-$CH_2CH_2CH_2SO_2$— and Asp is the leaving Pt chelating group, amidoaspartate, which is chelated to Pt by two single coordinate bonds. The Pt is also chelated by two single coordinate bonds to the stable ligand, which, again, is DACH. In the above examples, it is understood that (linker)-(leaving chelating group)=Pt=(stable chelating group) groups are appended to methacrylamide monomers only.

Since the exact desired percentage of each of the components in a copolymer is not usually synthetically achievable despite the care taken to use the exact ratio of monomers, the use of the term "approximately" is used to signify that the number shown in the structural formula represents a theoretical value which may vary from that observed by analytical means by as much as ±10%. Thus, in the phrase, "q is approximately 90%," q in fact can be anywhere from 81-99% (90±10%).

As used herein, the term "cancer" refers to various types of malignant neoplasms, most of which can invade surrounding tissues, and may metastasize to different sites, as defined by Stedman's Medical Dictionary, 25th edition (Hensyl ed. 1990). Examples, without limitation, of cancers which may be treated using the compounds of the present invention include, but are not limited to, brain, ovarian, colon, prostate, kidney, bladder, breast, lung, oral and skin cancers.

As used herein, the terms "treat", "treating" and "treatment" refer to a method of alleviating or abrogating a solid tumor cancer and/or its attendant symptoms. In particular, the terms simply mean that the life expectancy of an individual affected with a cancer will be increased and/or that one or more of the symptoms of the disease will be reduced.

As used herein, "administer," "administering" or "administration" refers to the delivery of a compound or compounds of this invention or of a pharmaceutical composition containing a compound or compounds of this invention to a patient in a manner suitable for the treatment of a particular cancer.

A "patient" refers to any higher organism that is susceptible to solid tumor cancers. Examples of such higher organisms include, without limitation, mice, rats, rabbits, dogs, cats, horses, cows, pigs, sheep, fish and reptiles. Preferably, "patient" refers to a human being.

As used herein, a "chemotherapeutic" refers to a compound that is useful for treating a disease or disorder in a patient. In particular, a chemotherapeutic, as used herein, refers to a compound that is useful for treating a cancer, especially a solid tumor cancer, in a patient.

As used herein, the term "therapeutically effective amount" refers to that amount of a compound or combination of compounds of this invention which has the effect of (1) reducing the size of the tumor; (2) inhibiting (that is, slowing to some extent, preferably stopping) tumor metastasis; (3) inhibiting to some extent (that is slowing to some extent, preferably stopping) tumor growth; (4) relieving to some extent (or preferably eliminating) one or more symptoms associated with the cancer; and/or (5) extending survival time of the patient.

As used herein, a "pharmaceutical composition" refers to a mixture of one or more of the compounds of this invention with other chemical components such as pharmaceutically acceptable excipients. The purpose of a pharmacological composition is to facilitate administration of a compound of this invention to a patient.

As used herein, a "pharmaceutically acceptable excipient" refers to an excipient that does not cause significant irritation to an organism and does not abrogate the biological activity and properties of the administered composition. Examples, without limitation, of excipients include calcium carbonate, calcium phosphate, various sugars and types of starch, cellulose derivatives, gelatin, vegetable oils and polyethylene glycols.

As used herein, "pH stating" refers using a device that is capable of maintaining the pH of a solution within a selected range by either continuously or at specifice intervals measuring the pH of the solution and tittering in acid or base as necessary to bring the pH back into the desired range.

As used herein, the subscript "s" when use in conjunction with the formula of a compound of this invention refers to the range of molecular weights in kDaltons of the polymeric portion of the molecule.

Discussion

Platinum(II), also designated as Pt(II), forms four-coordinate square planar complexes with ligands with free electron pairs. In classic antitumor platinum complexes, two of the four ligands are selected so as to be labile under physiological conditions while the other two are stable. The stable groups are most often ammonia or amines at least one of which has an N—H bond capable of hydrogen bonding to the phosphate backbone of DNA. Generally speaking, the am(m)ine groups relate to tumor specificity and drug efficacy while the labile groups relate to stability and toxicity. The novel small-molecule complexes of this invention are designed to take advantage of various chemical, physical and biochemical features to achieve an optimal relationship between specificity, efficacy and toxicity and to thereby maximize the therapeutic index of the compounds.

For example, without limitation, some of the complexes of the present invention are 5-member ring chelates having various substituents that are expected to confer a broad range of biochemical characteristics on the resulting complex. The general structure of the 5-member ring chelates is:

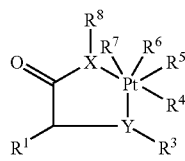

In the above compound:
Pt is in a +2 or a +4 oxidation state;
X and Y are independently selected from the group consisting of oxygen, nitrogen and sulfur, provided that, if X or Y is sulfur, the other is nitrogen or oxygen, wherein;
$R^1$ is selected from the group consisting of:
—O;
—$R^9$;
-(1C-6C)alkyl-$R^9$;
(1C-6C)alkyl-Z$R^9$;
C(O)O⁻R⁺;
—C(O)Z$R^9$; and,
-(1C-6C)alkyl-C(O)Z$R^9$, wherein:
Z is selected from the group consisting of oxygen and —NH—;
R⁺ is selected from the group consisting of Na⁺ and K⁺;
$R^9$ is selected from the group consisting of:
hydrogen,
-(1C-6C)alkyl optionally substituted with one or more
—OH groups; and,
-(linker)-$R^{10}$, wherein:
-(linker) is selected from the group consisting of:
—(OCH₂CH₂)$_a$O(C=O)$_b$—;
—(CH(OH))$_a$CH₂O(C=O)$_b$—;
—NH-(1C-20C)alkyl-C(=O)—;
—NH-poly(ethylene glycol)-NH—; and,

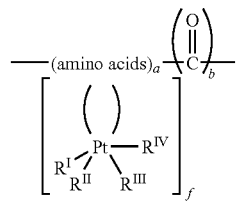

wherein:
a is 0-50;
b is 0 or 1;
f is 0, 1, 2, 3 or 4, provided that for each individual amino acid of the O— to 50 "a" amino acids, f is 0 or 1;
$R^I$ is the same as $R^4$;
$R^{II}$ is the same as $R^5$;
$R^{III}$ is the same as $R^6$; and,
$R^{IV}$ is the same as $R^7$;
$R^{10}$ is selected from the group consisting of:
hydrogen: and,
a natural, semi-synthetic or synthetic backbone polymer;
provided that:
when Y is nitrogen, $R^1$ is =O;
$R^3$ and $R^8$ are independently selected from the group consisting of:
—$R^9$;
-(1C-6C)alkyl-$R^9$;
—C(O)Z$R^9$;
—C(O)$R^9$;
—S(O)₂$R^{11}$;
—P(O)(O$R^9$)₂(O$R^{12}$);
—P(O)(O$R^9$)(O$R^{12}$)₂; and,
aryl optionally substituted with one or more entities independently selected from the group consisting of:
—$R^9$
—O$R^9$;
—N$R^9R^{12}$;
—NO₂;
halo;
—C≡N; and,
—C(O)Z$R^9$;
$R^{11}$ is selected from the group consisting of:
—$R^9$;
-(1C-6C)alkyl-$R^9$;
—N$R^9R^{12}$; and,
aryl optionally substituted with one or more entities selected from the group consisting of:
—$R^9$;
—O$R^9$;
—N$R^9R^{12}$;
—NO₂;
halo;
—C≡N; and,
—C(O)O$R^9$;

$R^{12}$ is selected from the group consisting of hydrogen, -(1C-6C)alkyl and, when $R^{12}$ is bonded to a phosphorus through an oxygen atoms, i.e., P—($OR^2$), $Na^+$ and $K^+$, provided that:

when X and/or Y is oxygen, $R^3$ and/or $R^8$ does not exist;
when X or Y is sulfur, $R^3$ or $R^8$ is -(1C-6C)alkyl;

$R^4$ and $R^5$ are independently selected from the group consisting of:

ammonia;
an optionally substituted primary, secondary or tertiary (1C-6C)alkyl amine;
an optionally substituted (3C-8C)cycloalkyl amine;
an optionally substituted aryl amine; an optionally substituted nitrogen heteroaryl;
an optionally substituted nitrogen heteroalicyclic;
an optionally substituted aminomethyl nitrogen heteroalicyclic; or, together, as $R^4$—$R^5$:
  an optionally substituted 1,2-, 1,3- or 1,4-diamino (1C-8C)alkane;
  an optionally substituted 1,2- or 1,4-diamino (3C-8C) cycloalkane;
  an optionally substituted 1,1- or 1,2-di(aminomethyl) (3C-8C)cycloalkane;
  an optionally substituted 1,1- or 1,2-di(aminomethyl) heteroalicyclic;
  an optionally substituted di(nitrogen heteroaryl); and,
  an optionally substituted methylene di(nitrogen heteroaryl);

if Pt is in the +2 oxidation state (Pt(II)), $R^6$ and $R^7$ do not exist; and, if Pt is in the +4 oxidation state (Pt(IV)), $R^6$ and $R^7$ are independently selected from the group consisting of —OH, $H_2O$, Cl and (1C-6C)alkylC(O)—.

Some specific examples of 5-member ring compounds of this inventions follow. It is emphasized that these compounds are not intended, nor are they to be construed, as limiting the scope of this invention in any way.

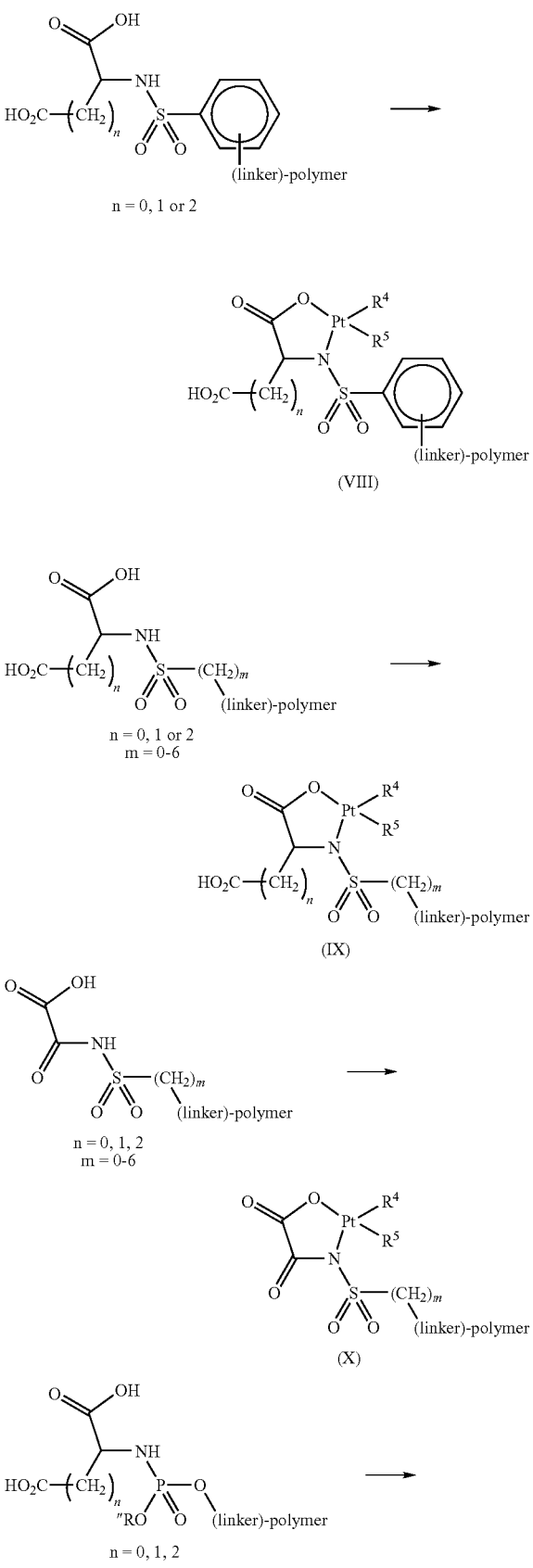

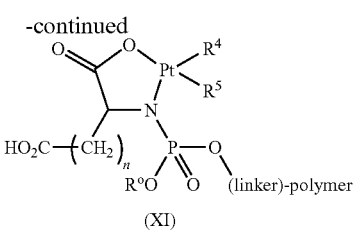

(XI)

In the above compounds, $R^4$ and $R^5$ are both $NH_3$ or together ($R^4$-$R^5$) form 1R, 2R-diaminocyclohexane. $R^0$ is a (1C-6C)alkyl group.

Compound (VI) chelates through a carboxamide nitrogen and a carboxylate oxygen and would be expected to be quite labile and therefore pharmaceutically active. Compound (VII), however, would be expected to be even more active because the nitrogen ligand is an imide anion which is more delocalized that a carboxamide anion and therefore is expected to be more labile. Likewise, the alkyl sulfonamide nitrogen ligand of compound (IX), the phosphamide ligand of compound (XI), the aryl sulfonamide of compound (VIII) and the sulfonimide of compound (X) are expected to exhibit a balance between lability and stability that contributes in an positive manner to the therapeutic index of the compound.

Also within the contemplation of this invention are 6-member ring Pt complexes having the general formula:

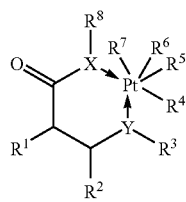

The various R groups have the same significance as in the 5-member ring compounds; $R^2$ is selected from among the same groups as $R^1$.

The 6-member ring chelates are expected to generally be more labile than the corresponding 5-member ring complexes. The chemical characteristics of 6-member rings compounds, however, will be susceptible to the same structural feature manipulations as the 5-member ring compounds. That is, 6-member ring imides are expected to be more labile than the corresponding amides and the corresponding alkyl sulfonamides, aryl sulfonamides, phosphamides, etc. are also expected to provide compounds with a useful balance of stability and lability. While the 6-member chelates may be formed from any combination of nitrogen, oxygen and sulfur (except as noted above), the 6-member N,O complex is also presently preferred. In fact, it is expected that, with amides having at least one hydrogen on the amide nitrogen and an oxygen in position to form a 5- or 6-member ring, an O,O complex may initially form but the amide will deprotonate to give a softer and therefore preferable ligand for Pt such that the O,O chelate rearranges to the N,O chelate. In the case of the 5-member ring O,O chelate, it is expected that, even in the presence of a deprotonated amide, an equilibrium may exist between the 5-member O,O and the 6-member N,O complexes.

Some specific examples of 6-member ring Pt complexes follow. As with the 5-member ring examples, the examples below are for illustrative purposes only and are not intended, nor are they to be construed, to limit the scope of this invention in any manner.

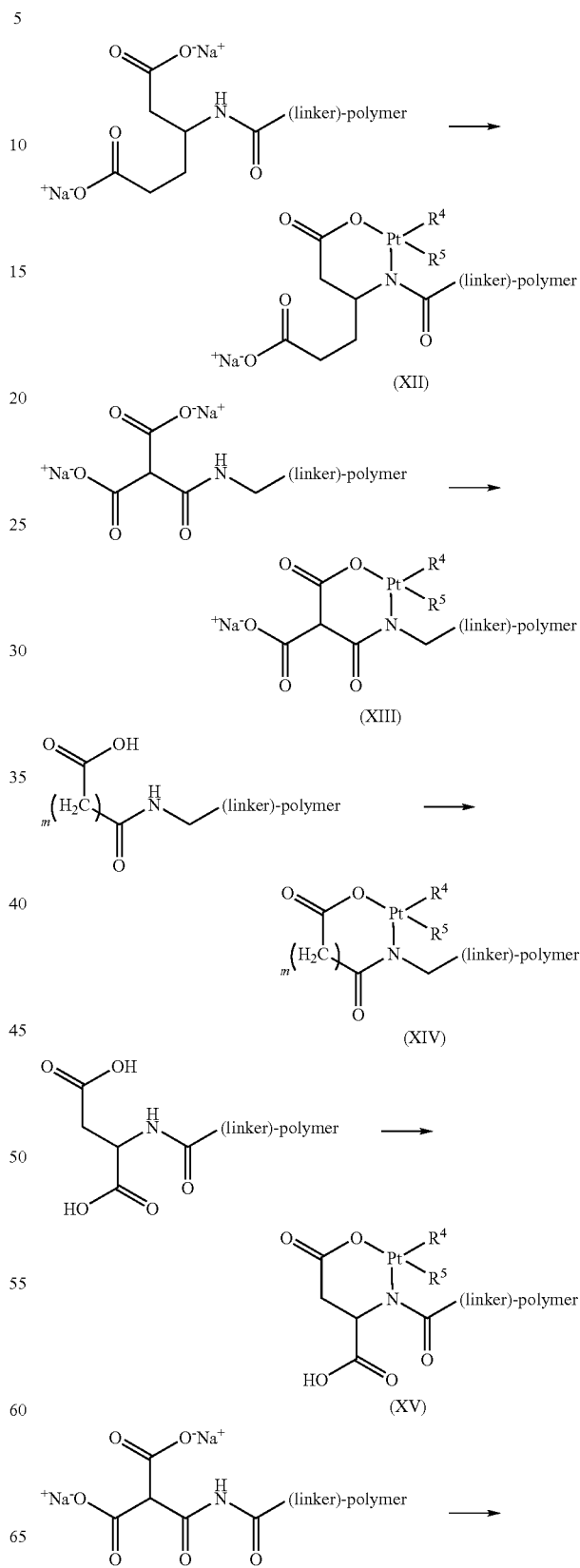

-continued

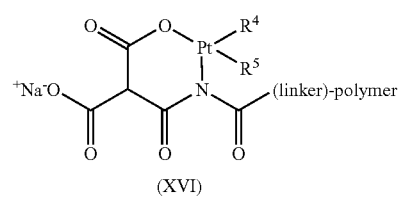

(XVI)

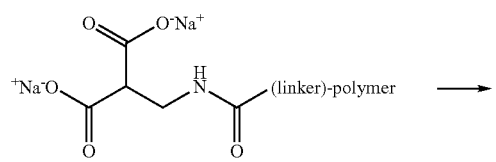

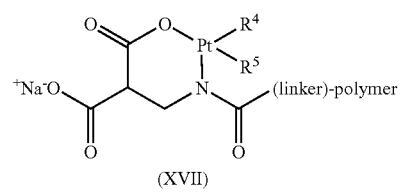

(XVII)

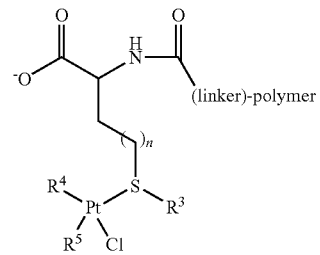

(XVIII)

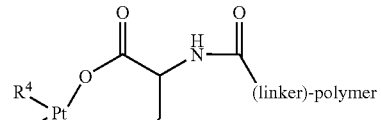

(XIX)

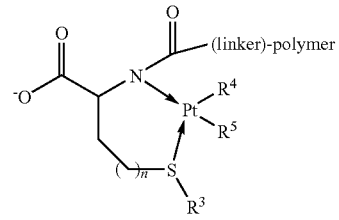

(XX)

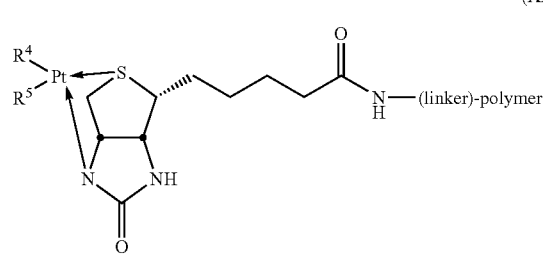

(XXI)

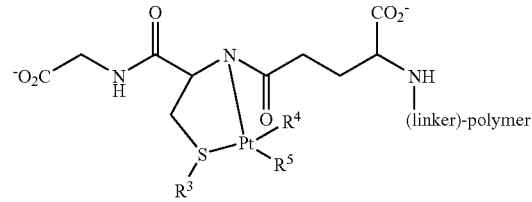

(XXII)

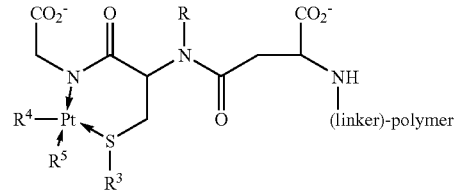

(XXIII)

$R^4$ and $R^5$ are both $NH_3$ or, together (i.e., $R^4$-$R^5$) are 1R, 2R-diaminocyclohexane.

Compound (XII) is an N,O-chelate of a carboxyl group and the nitrogen of β-glutamate, (XIII) is an N,O-chelate of a carboxyl and an amide with a second carboxylate group appended to the ring, (XIV) is an N,O-chelate of a carboxyl and an amide without an appended carboxylate; (XV) is and N,O-chelate of a carboxyl and the amide nitrogen of aspartate; (XVI) is an N,O-chelate of an carboxyl and an imide nitrogen and (XVII) is a chelate of a carboxyl and the amide nitrogen of 2-amidomethylmalonate.

While N,O chelates are presently preferred, some N,S chelates present intriguing possibilities and as such are within the scope of this invention. It is well known that Pt(II) species readily react with sulfur compounds (S-donors). Indeed, resistance to platinum chemotherapy directly correlates with glutathione levels where the free —SH group of the reduced glutathione binds virtually irreversibly (under physiological conditions) to the platinum thereby inactivating it. It has been shown, however, that the transport of platinum chemotherapeutics into the cell and perhaps all the way to the nucleus/DNA may be mediated by copper transport proteins (CTR1). CTRs are methionine rich which may explain how cisplatin and related compounds find their way past high concentrations of glutathione to reach the DNA. That is, the —$SCH_3$ group of methionine may coordinate with the platinum in a sufficiently stable manner to compete favorably with the —SH of glutathione but still be labile enough to release the Pt species once inside a neoplasm. This also suggests that ab initio prepared Pt-thioether complexes should show anti-cancer activity in vivo. Such complexes include Pt(II) complexes of mono- or di-thioethers and sulfoxides.

Several cis-diamine platinum(II) complexes of thioethers of this invention are shown below. As before, the examples shown are not intended, nor are they to be construed, to limit the scope of this invention in any manner.

$R^3$, $R^4$ and $R^5$ comprise the same range of possible groups as set forth above.

Compound (XVIII) is a monodentate complex with methionine. Compound (XIX) is an O,S bidentate complex, also of methionine. Compound (XX) is an N,S bidentate complex with S-alkyl cysteine. Also included in the scope of the invention are the corresponding sulfoxides of the compounds shown. It is also expected that the lability of the Pt—S bond will depend on the bulk of the R group on sulfur; that is, the larger the group the more strained and therefore more labile the Pt—S bond will be.

Compound (XXI) is a cis-diamine platinum(II) complex of biotin. Biotin has been found to be capable of targeting polymer-drug conjugates to certain surface cell receptors that are over-expressed on some tumors (unreported observation). Biotin is an attractive thioether because it is likely to be more reactive than other thioethers due to the strain of bridging across the two rings.

Even though glutathione itself deactivates Pt complexes, S-alkyl derivatives of glutathione are also expected to provide active thioether platinum adducts. The 5-membered S,N-chelate (XXII) is favored and is the expected product from S-alkyl glutathione. The 6-membered S,N-chelate (XXIII) can be obtained if the nitrogen that will otherwise form a 5-member ring is alkylated.

In addition to providing active chemotherapeutics, sulfur-containing compounds might also reduce the toxicity of the platinum complex. For instance, amifostine has been shown to remove methionine-platinum adducts in vitro and has been used clinically to reduce nephrotoxicity. Methionine itself has been shown to reduce ototoxicity in rats.

Seven-member ring complexes are also envisioned by this invention, although, as noted below, such may only be the case for Pt(IV) compounds. These are expected to be substantially more labile than either the 5- or 6-member ring complexes. In fact, only one 7-member dicarboxylato O,O-complex has heretofor been reported although 1,5-diamine bidentate complexes are known. It is expected that 7-member N,O complexes should form if the nitrogen is an imide, sulfonamide or phosphonamde.

In any of the above cases, i.e, 5-member, 6-member or 7-member chelates, the platinum can be divalent; i.e., in the +2 oxidation state (Pt(II), as shown, or it can be tetravalent, the +4 oxidation state (PtIV). Such complexes will consist of two additional ligands, such as, by way of non-limiting example, chlorine, water (the "aqua" ligand) and/or carboxyl. Pt(IV) complexes are known to be substantially more stable than the corresponding Pt(II) species; in fact, they are so stable that they are generally assumed to be pharmacologically inactive. The use of Pt(IV) may be particularly useful when forming 7-member ring bidentate chelates. Pt(IV) is readily reduced to Pt(II), the active species, under physiological conditions. The use of Pt(IV) complexes adds yet another layer of design control to the compounds of this invention and further broadens the palate of possible substitution patterns in search for optimal pharmaceutical chemotherapeutics.

As indicated above, if an O,O chelate is desired even when there is a nitrogen ligand in position to form a 5- or 6-member ring, the O,O compound can still be obtained by further substituting the nitrogen, e.g., the amide nitrogen below, so that it can no longer deprotonate to the softer, preferred amido ligand. R⁰ can be, for instance, a (1C-6C)alkyl group, which will prevent formation of the otherwise preferred 5-member ring N,O complex:

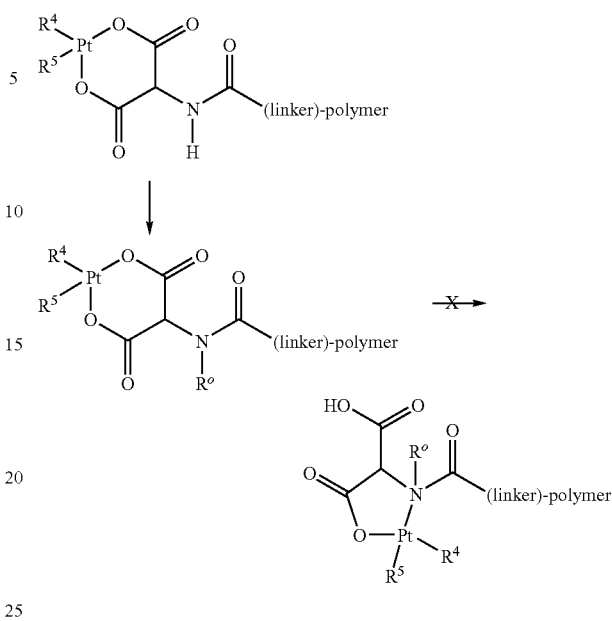

The various structural modifications of platinum complexes disclosed herein can also be manipulated so as to take advantage of differences in the physiological/biochemical environment in tumors compared to normal tissue. For example, the pH of normal tissue and of circulating blood is 7.4. The pH within tumors is often an order of magnitude lower, i.e, 6.2-6.5. The lower pH results from a lower oxygen partial pressure within tumor cells. The cells adapt to this by switching to anaerobic metabolic pathways which results in an increase in lactate production and concomitant reduction in extracellular pH. A platinum complex involving weakly basic ligands such as imines should provide chelates that are relatively stable at essentially neutral pH, i.e., 7.4, but are substantially less so at one pH unit lower where the more acidic medium can protonate the ligand resulting in the cleavage of the coordinate bond.

A presently preferred embodiment of this invention is a molecule comprising a backbone polymer to which (amino acids) linker groups bearing terminal Pt chelates have been appended wherein a proportion of the linker groups also have a Pt chelate along the linker chain between its point of attachment to the polymer and the terminal Pt complex. Such a Pt chelate/complex is sometimes referred to herein as an "intermediate Pt complex/chelate."

In addition, a compound in which an (amino acids) linker is further linked to a —NH(CH$_2$)$_v$SO$_2$— group, which, in turn, is covalently bonded to the leaving ligand chelate, is also a presently preferred embodiment of this invention.

The above molecule also comprises water-solubilizing groups in another presently preferred embodiment of this invention.

Furthermore, the above molecule, with or without the water-solubilizing groups, may comprise an active tumor targeting group (as opposed to the passive EPR-related accumulation also expected from the polymeric compounds of this invention) in yet another presently preferred embodiment of this invention.

The stability of a polymer-(linker)-Pt-complex of this invention and, thus, its ability to remain intact until it reaches a target tumor is dependent on several factors: the distance between the polymer backbone and the Pt complex(es), which correlates with the length of the linker, the composition of the "stable" ligand(s) and the composition of the leaving-ligand(s).

Table 1 shows the effect of the distance from the backbone polymer to the Pt complex and of the structure of the stable ligand/chelate on the stability of the molecule as represented by the percent small molecule Pt species, i.e., a Pt species no longer tethered to a polymeric backbone, released at 3 and 24 hours.

The compound tested comprised a poly(N-(2-hydroxypropyl)methacrylamide (90%)-co-(N-(linker)-Pt complex) methacrylamide (10%)) polymer and either cis-diammine or 1R,2R-diaminocyclohexane (DACH) as the stable ligands/chelate of the Pt complex. The leaving-ligand comprised an N,O bidentate ligand with amidoaspartate (Asp) or amidomalonate (Ama). As can be seen, Ama complexes are more stable than Asp complexes, the further from the backbone the complex is, the more stable it is and, cis-diammine stable-ligand complexes are more stable than DACH chelate complexes.

TABLE 1

| Linker between polymer and complex | Percent small platinum released from cis-diammine Pt(II) complex at 37° C. in PBS | | Percent small platinum released from 1R,2R-DACH Pt(II) complex at 37° C. in PBS | |
|---|---|---|---|---|
| | 3 hours | 24 hours | 3 hours | 24 hours |
| No linker-Ama=Pt= | 4.1% | 23.8% | 17.6% | 66.3% |
| Gyl-Gly-Ama=Pt= | 0.6% | 3.2% | 1.5% | 7.6% |
| Gly-Gly-Asp=Pt= | 3.9% | 11.0% | 4.4% | 12.6% |
| Gly-Phe-Leu-Gly-Ama=Pt= | 0.7% | 2.1% | 0.7% | 2.4% |
| Gly-Phe-Leu-Gly-Asp=Pt= | 1.5% | 4.7% | 2.0% | 6.5% |

The difference in percent Pt release due solely to the change from $NH_3$ to DACH as the stable ligand suggests that a substantial level of control over delivery of small molecule species to a target tumor is possible based on this structural variation alone. Thus, the use of a broad range of stable ligands is within the scope of this invention. Presently preferred stable ligands are amines or diamines of which the following are representative, non-limiting examples: $NH_3$, $CH_3CH_2NH_2$, $CH_3CH_2CH_2NH_2$, $CH_3CH(NH_2)CH_3$, $CH_3CH_2CH(NH_2)CH_3$, $H_2NCH_2CH_2CH_2NH_2$, $H_2NCH_2CH_2CH_2CH_2NH_2$, $H_2NCH_2CH_2CH(CH_3)CH_2NH_2$, $(HOCH_2)_2C(CH_2NH_2)_2$,

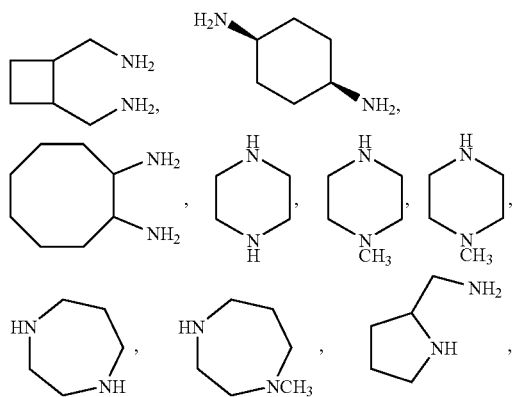

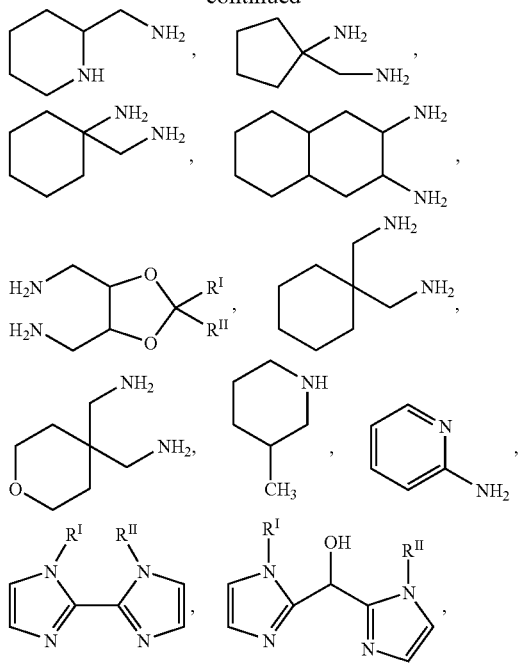

and $NH_2CH(R^{III})CH(R^{IV})NH_2$, wherein $R^I$ and $R^{II}$ are independently (1C-6C)alkyl and $R^{III}$ and $R^{IV}$ are independently hydrogen, (1C-6C)alkyl,

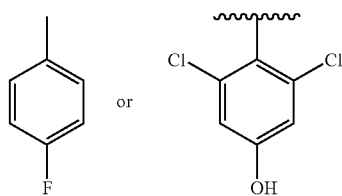

While (amino acids) linkers are presently preferred, other linkers are also within the contemplation and scope of this invention. For example, without limitation, a poly(ethylene glycol) with up to 10 ethylene units could be coupled with L-alanine or L-alanine-L-valine as the chelating agent. Such linkers would also be water-solubilizing. In the latter case, L-alanine-L-valine has been shown to be sensitive to cleavage by the enzyme thermolysin and thermolysin-like enzymes have been reported as being expressed by a number of tumor types (Suzawa, et al., *J. Control Release*, 2000, 69(1):27-41). Polymers containing such linkers can be monodisperse (all strands essentially the same size) or polydisperse (range of strand sizes) although particles with low dispersities, which are more easily pharmaceutically characterizable, are presently preferred.

The linkers of this invention may, but need not necessarily, be biodegradable. While biodegradability may be a desired characteristic in some cases, it has been found to not be necessary for the release of active Pt species. While not being bound to any particular theory, it is postulated that the bound Pt complex, despite the steric constraints at the N,O-complexing site, is still susceptible to hydrolytic cleavage at the linker thus releasing the diaqua small molecule Pt complex.

Other linkers useful for the preparation of molecules of this invention include ω-aminoalkanoic acids of from 1 to 20 carbon atoms wherein the terminal amino group is reacted with a pendent carboxylic acid group of a backbone polymer and the carboxylic acid group at the other end of the linker is used to form the chelate with Pt. The carbon atoms between the amino and the carboxyl group can be further substituted with water-solubilizing groups such as, without limitation, hydroxyl and/or guanidino.

Glucuronic acid can also be used as a linker along with other groups such as aromatic spacers (Y. L. Leu, *J. Med. Chem.*, 1999, 42:3623-28). Glucuronic acid is stable in water and plasma but is degraded β-glucuronidase, which is know to accumulate in the extracellular lysosomes of some tumors.

In addition to varying the backbone polymer, the composition of the linker and of the the stable ligands of a Pt(II) complex of a molecule of this invention, the use of Pt(IV) complexes is also within the scope of the invention.

The cytostatic or cytotoxic Pt(II) complexes owe their pharmacological activity to their ability to form adducts with DNA. Pt(IV) complexes do not form such adducts and are relatively biologically inert. Their very inertness, however, can be used to advantage. That is, Pt(IV) complexes should be amenable to oral administration and should be capable of entering and passing through the circulatory system unaffected. They then could circulate until they passively encounter a target tumors. Then, upon entering the tumor, they could convert to the active Pt(II) species. The stability of Pt(IV) complexes is also expected to permit formulation in aqueous compositions rather than, say, requiring a lyophilized powder that must be reconstituted.

The environment within many tumors is well-suited to effect the conversion of Pt(IV) species to Pt(II) species. That is, in vivo reduction of Pt(IV) to Pt(II) is believed to occur through a reductase enzyme in the presence of a reducing agent/anti-oxidant such as glutathione or ascorbic acid, a milieu commonly encountered in the extra-cellular environment of tumors.

Pt(IV) complexes can be prepared by oxidation (e.g., hydrogen peroxide or chlorine) of Pt(II) complexes in the presence of ligands such as acetate which will occupy the axial positions when the 4-coordinate Pt(II) species is oxidized to the 6-coordinate Pt(IV) species. It is expected that, using relatively mild oxidation techniques, the Pt(IV) complexes of any Pt(II) complex described herein can be readily obtained.

While drug delivery to tumors is generally improved by using a water-soluble backbone polymer or by appending water-solubilizing groups to a polymer backbone, delivery can be further enhanced by appending specific tumor-targeting groups to the backbone polymer. The rationale is that, by virtue of the affinity of the targeting group for a receptor exclusive to, or at least over-expressed by, neoplastic cells or for some other specific tumor characteristic, the concentration of the polymer in the vicinity of the tumor is increased compared to that in the vicinity of normal cells/tissues that do not exhibit the characteristic. Even if the affinity is low, such as in the case of a low binding constant (either intrinsically low, or diminished because the targeting group is bound to the polymer, and so is less able to interact with the target characteristic), increased concentration and/or selectivity of the drug is still to be expected. In addition, when the characteristic is a receptor and a single polymer strand of a drug hereof contains several targeting groups, there may be several receptor-ligand interactions for each polymer strand, amplifying the affinity of the polymer. This is known as the 'multi-valency' effect. Targeting groups such as folate and vitamin B12 are expected to be capable of taking advantage of this phenomenon.

It has been recognized that rapidly dividing cells undergo receptor-mediated uptake of certain vitamins. In particular, many types of neoplastic cells contain receptors which mediate rapid absorption of folic acid (Antony, *J. Biol. Chem.*, 1985, 260(28):14911-7). Thus, linking folic acid to chemotherapeutic agents has been recognized as a useful method for increasing the tumor concentration of chemotherapeutics (Leamon, C. P., Low, P. S., *Drug Discov. Today*, 2001, 6(1): 44-51; Wang, S., Low, P. S., *J. Control Release*, 1998, 53(1-3):39-48), U.S. Pat. Nos. 5,108,921; 5,416,016; 5,635,382; 5,820,847; 5,688,488). Thus, it is expected that folate, appended to the backbone of a polymer-linker-Pt complex of this invention, will likewise assist in the accumulation of the compounds in target tumors.

Tumor-targeting peptides are also presently of particular interest. Several tumor-targeting peptides have been described for use in radionuclide imaging (Behr, T. M., Gotthardt, M., Barth, A., Behe, M. Q., *J. Nucl. Med.*, 2001, 45(2):189-200), and in targeting of 1:1 peptide-chemotherapeutic agent conjugates (Schally, A. V., Nagy, A., *Eur. J. Endocrinol.*, 1999, 141(1):1-14). Other targeting peptides include, without limitation, somatostatin analogs and vasoactive intestinal peptide (VIP). VIP has shown promise for targeting colorectal cancer (Rao, et al., *Nuclear Medicine and Biology*, 2001, 28:445-450). These and other tumor-targeting peptides are likewise expected to be amenable to attachment to the polymer backbone of the compounds of this invention and to assist in the targeting of the compounds to tumors.

Essential fatty acids such as docosahexaenoic acid (DHA), while used by virtually all types of cells, are particularly avidly taken up by tumors, probably due to the uncontrolled growth characteristic of neoplastic cells. It is expected that fatty acids appended to the polymeric backbone of a compound of this invention will be useful to further faciliate the targeting of tumors.

Bioreductive molecules such as, without limitation, nitroimidazoles are known to bind to hypoxic tissue but not to normoxic tissue (P. Wardman, *Radiat. Phys. Chem.*, 1987, 30:423; Chapman, J. D., et al., *Advanced Topics on Radiosensitizers of Hypoxic Cells*, A. Breccia, C. Rimondi, and G. E. Adams, eds., Plenum Press, New York, pp. 91-103). That is, nitroimidazoles are reduced by reductases present in virtually all cells but in normoxic tissue, the reaction is rapidly reversed and the compound can be excreted. In hypoxic tissue, however, the reduced species is converted to an entity that forms covalent bonds with endogenous nucleophiles, thereby trapping the compound in the tissue. While some neoplastic tissues are similar to hypoxic tissues in their ability to trap bioreductive agents, they are different from hypoxic tissues in that the latter do not exhibit the EPR effect and it is expected that large molecules, such as the polymer-bound Pt complexes of this invention, when modified with bioreductive groups will preferentially invade and accumulate in tumor tissues even in the presence of hypoxic tissue. It is expected that a polymer-(linker)-Pt complex/bioreductive agent will be irreversible immobilized in the tumor after which small molecule Pt species can be released over virtually any desired time frame.

It is presently a particularly preferred embodiment of this invention, with regard to any of the compounds of this invention wherein the compound comprises a -(linker)-polymer group, as shown above, or a -(linker)-$R^{10}$ group wherein $R^{10}$ is a polymer, as seen below, that the linker group contains one or more additional Pt chelates at a location or locations intermediate between a terminal chelate (e.g., the compounds above) and the point of attachment of the linker to the polymer backbone. The additional Pt chelates may have the same or different structures than the terminal chelate and/or than each other.

Syntheses

The synthesis of presently preferred embodiment of this invention, i.e., polymer-backbone-containing compounds having poly(amino acids) linkers appended thereto, the linker each having a terminal Pt chelate and a proportion of them also having a second Pt chelate located between the terminal chelate and the point of attachment of the linker to the polymeric backbone, is also provided in the Examples section.

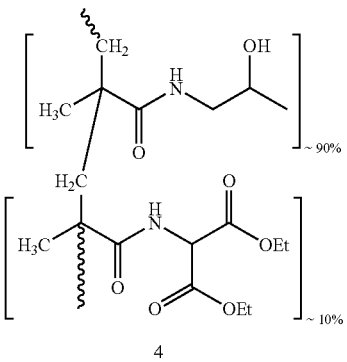

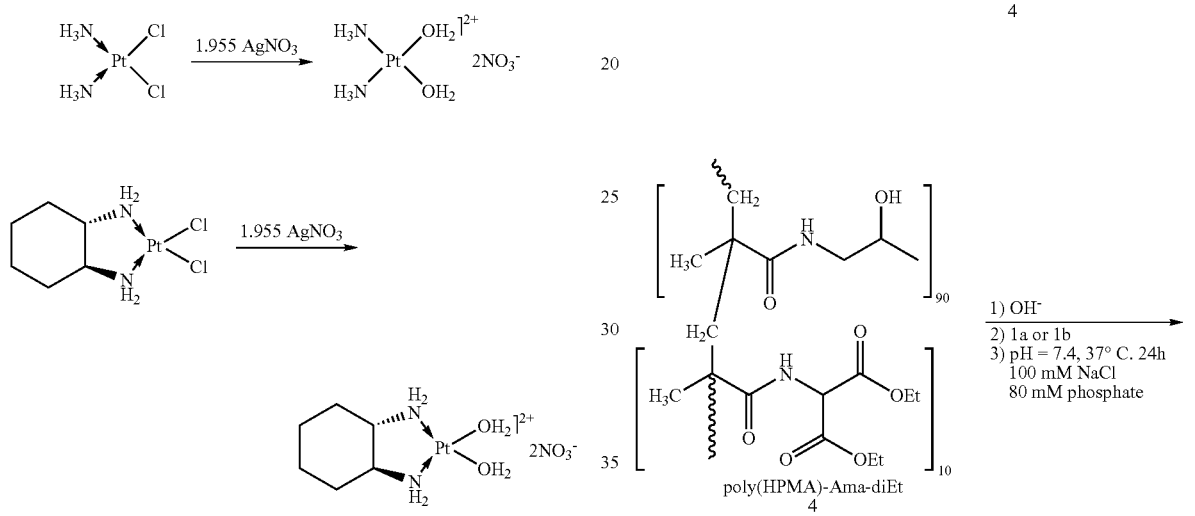

Scheme 1: Preparation of cis-diammine diaqua platinum(II) (1a) cation and 1R, 2R-diaminocyclohexyl-diaqua platinum(II) (1b) cation.

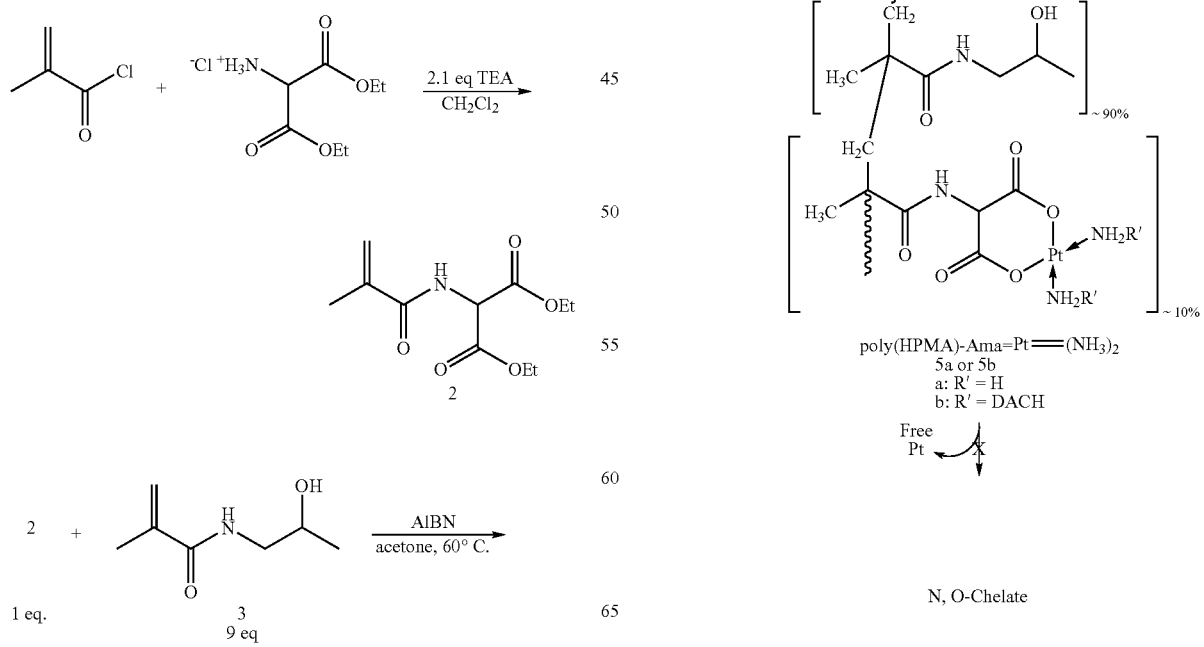

Scheme 2: Preparation of monomer MA-AmadiEt, poly(HPMA)-AmadiEt, and poly(HPMA)-Ama=Pt=(NH2R')2.
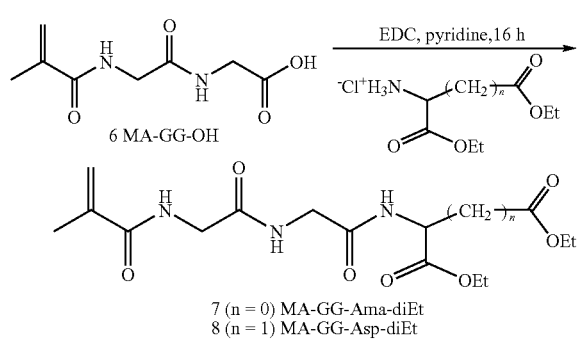
Scheme 3: Preparation of MA-GG-Ama-diEt, MA-GG-Asp-diEt, and MA-GG-ONp.
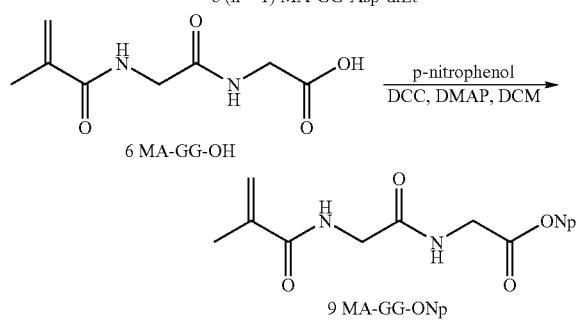
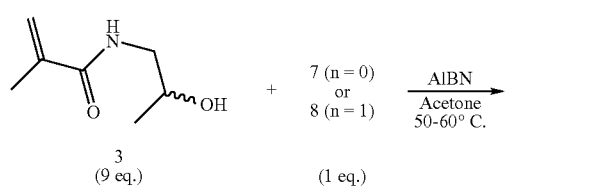
-continued
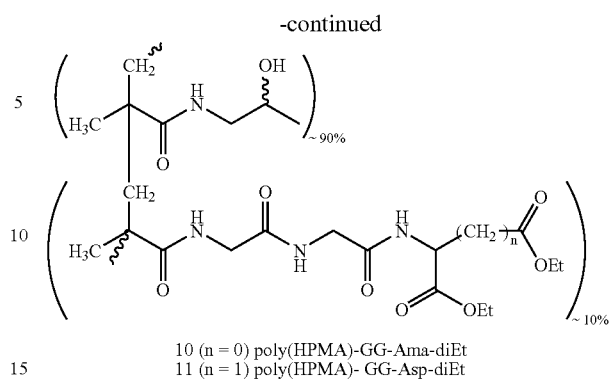
Scheme 4: Preparation of poly(HPMA)-GG-Ama-diEt (5), and poly(HPMA)-GG-Asp-diEt (6).
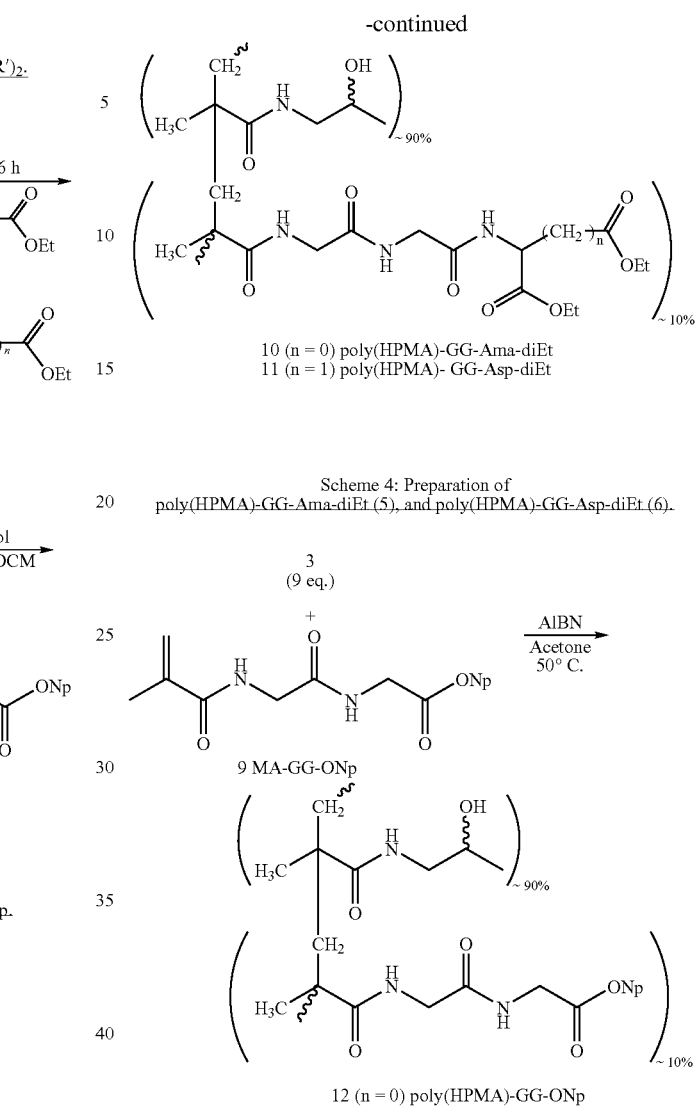
Scheme 5: Preparation of poly(HPMA)-GG-ONp (12).
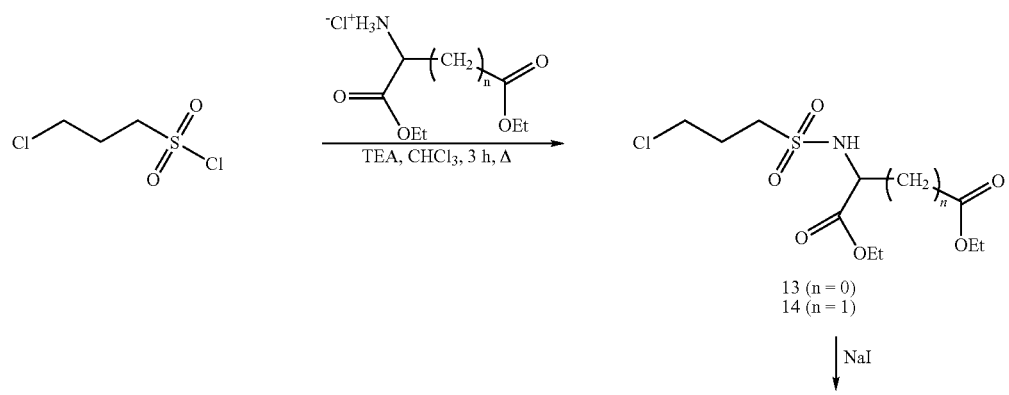

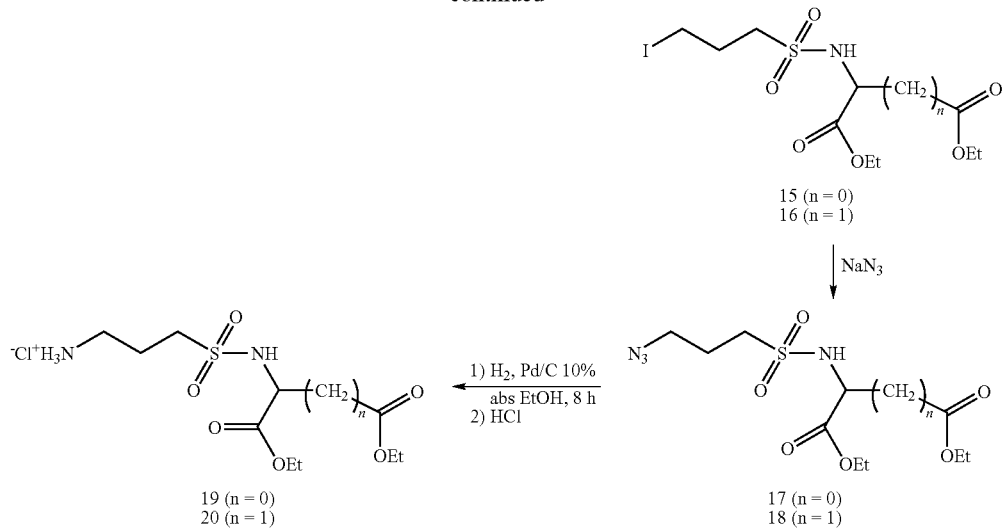
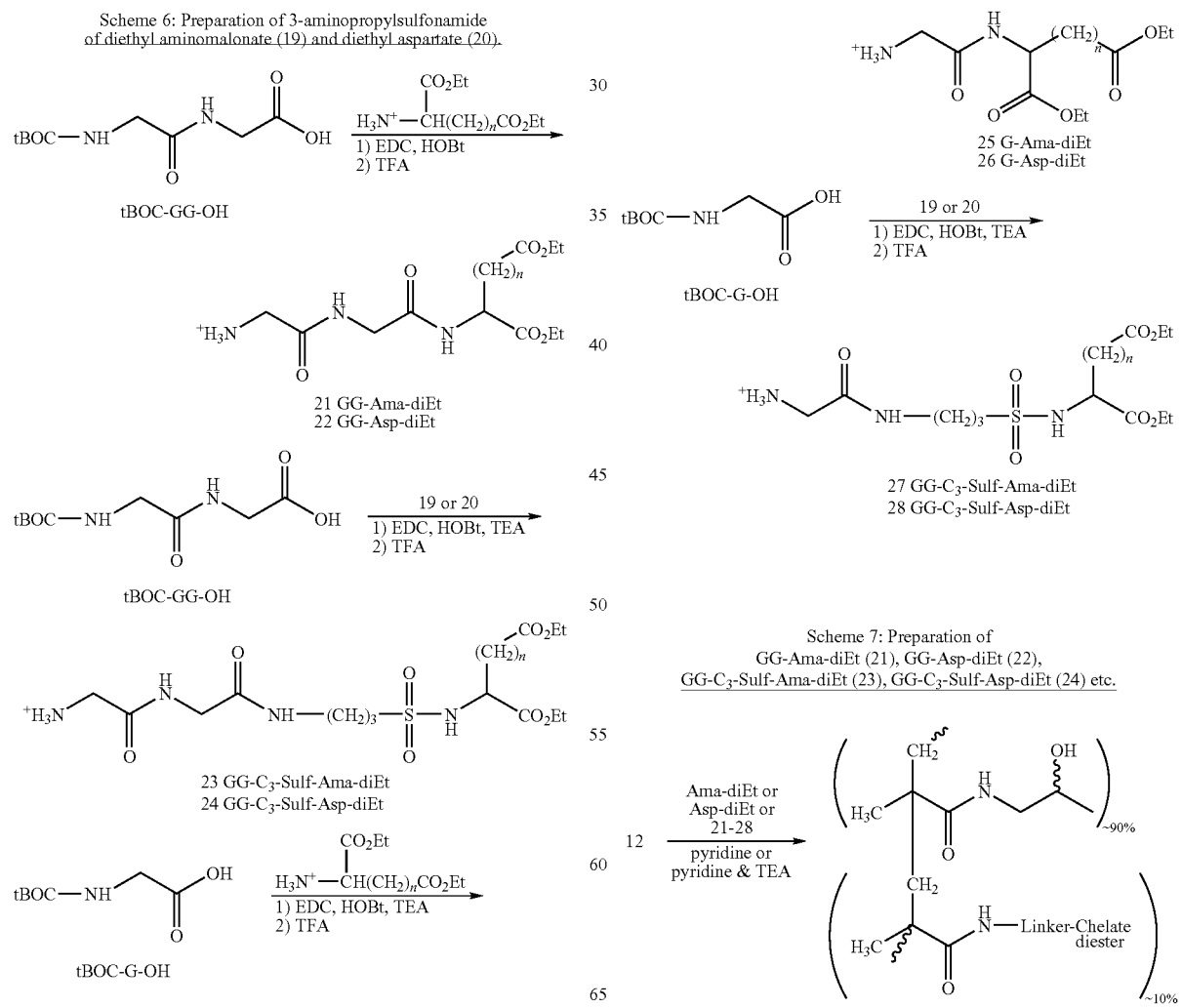

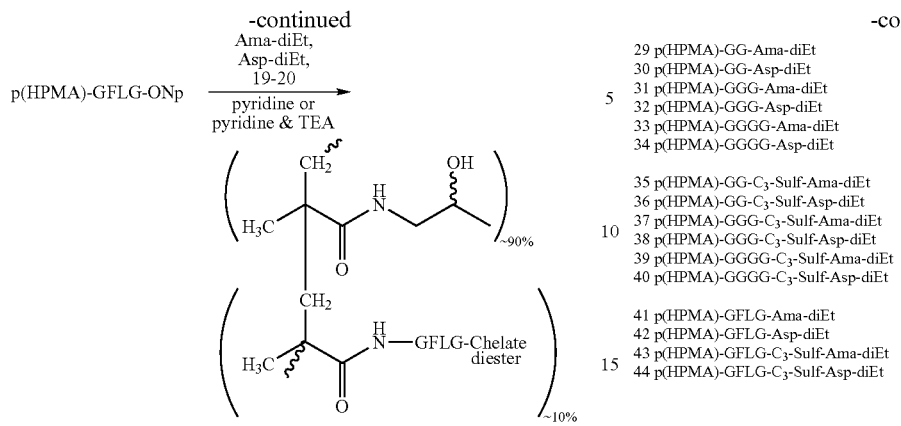

29 p(HPMA)-GG-Ama-diEt
30 p(HPMA)-GG-Asp-diEt
31 p(HPMA)-GGG-Ama-diEt
32 p(HPMA)-GGG-Asp-diEt
33 p(HPMA)-GGGG-Ama-diEt
34 p(HPMA)-GGGG-Asp-diEt 35 p(HPMA)-GG-$C_3$-Sulf-Ama-diEt
36 p(HPMA)-GG-$C_3$-Sulf-Asp-diEt
37 p(HPMA)-GGG-$C_3$-Sulf-Ama-diEt
38 p(HPMA)-GGG-$C_3$-Sulf-Asp-diEt
39 p(HPMA)-GGGG-$C_3$-Sulf-Ama-diEt
40 p(HPMA)-GGGG-$C_3$-Sulf-Asp-diEt 41 p(HPMA)-GFLG-Ama-diEt
42 p(HPMA)-GFLG-Asp-diEt
43 p(HPMA)-GFLG-$C_3$-Sulf-Ama-diEt
44 p(HPMA)-GFLG-$C_3$-Sulf-Asp-diEt Scheme 8: Preparation of various poly(HPMA)-Linker-Chelates.

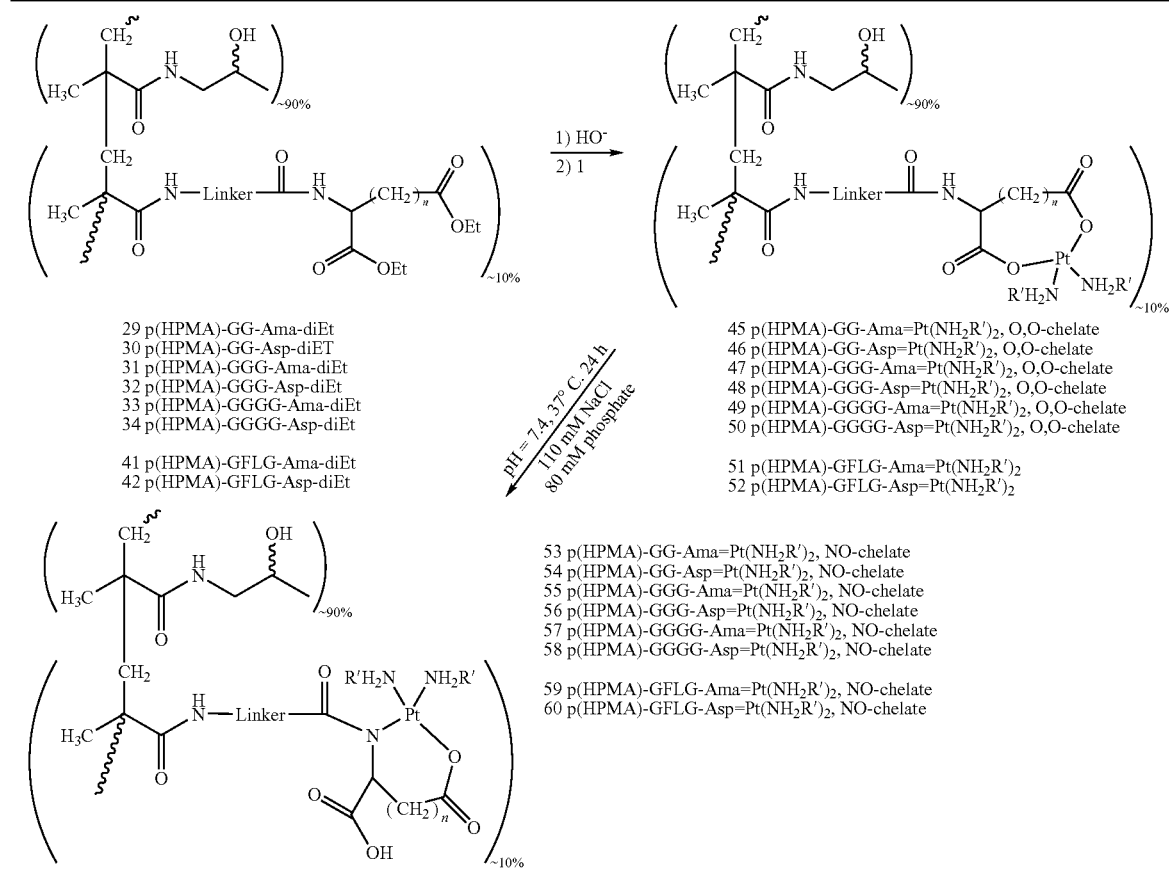

29 p(HPMA)-GG-Ama-diEt
30 p(HPMA)-GG-Asp-diET
31 p(HPMA)-GGG-Ama-diEt
32 p(HPMA)-GGG-Asp-diEt
33 p(HPMA)-GGGG-Ama-diEt
34 p(HPMA)-GGGG-Asp-diEt 41 p(HPMA)-GFLG-Ama-diEt
42 p(HPMA)-GFLG-Asp-diEt 45 p(HPMA)-GG-Ama=Pt($NH_2R'$)$_2$, O,O-chelate
46 p(HPMA)-GG-Asp=Pt($NH_2R'$)$_2$, O,O-chelate
47 p(HPMA)-GGG-Ama=Pt($NH_2R'$)$_2$, O,O-chelate
48 p(HPMA)-GGG-Asp=Pt($NH_2R'$)$_2$, O,O-chelate
49 p(HPMA)-GGGG-Ama=Pt($NH_2R'$)$_2$, O,O-chelate
50 p(HPMA)-GGGG-Asp=Pt($NH_2R'$)$_2$, O,O-chelate 51 p(HPMA)-GFLG-Ama=Pt($NH_2R'$)$_2$
52 p(HPMA)-GFLG-Asp=Pt($NH_2R'$)$_2$ 53 p(HPMA)-GG-Ama=Pt($NH_2R'$)$_2$, NO-chelate
54 p(HPMA)-GG-Asp=Pt($NH_2R'$)$_2$, NO-chelate
55 p(HPMA)-GGG-Ama=Pt($NH_2R'$)$_2$, NO-chelate
56 p(HPMA)-GGG-Asp=Pt($NH_2R'$)$_2$, NO-chelate
57 p(HPMA)-GGGG-Ama=Pt($NH_2R'$)$_2$, NO-chelate
58 p(HPMA)-GGGG-Asp=Pt($NH_2R'$)$_2$, NO-chelate 59 p(HPMA)-GFLG-Ama=Pt($NH_2R'$)$_2$, NO-chelate
60 p(HPMA)-GFLG-Asp=Pt($NH_2R'$)$_2$, NO-chelate

| ID | Linker-Chelate=Pt($NH_3$)$_2$ (N,O-) | ID | Linker Chelate=Pt=DACH (N,O-) |
|---|---|---|---|
| 53a | -GG-Ama=Pt($NH_3$)$_2$ | 53b | -GG-Ama=Pt=DACH |
| 54a | -GG-Asp=Pt($NH_3$)$_2$ | 54b | -GG-Asp=Pt=DACH |
| 55a | -GGG-Ama=Pt($NH_3$)$_2$ | 55b | -GGG-Ama=Pt=DACH |
| 56a | -GGG-Asp=Pt($NH_3$)$_2$ | 56b | -GGG-Asp=Pt=DACH |
| 57a | -GGGG-Ama=Pt($NH_3$)$_2$ | 57b | -GGGG-Ama=Pt=DACH |
| 58a | -GGGG-Asp=Pt($NH_3$)$_2$ | 58b | -GGGG-Asp=Pt=DACH |
| 59a | -GFLG-Ama=Pt($NH_3$)$_2$ | 59b | -GFLG-Ama=Pt=DACH |
| 60a | -GFLG-Asp=Pt($NH_3$)$_2$ | 60b | -GFLG-Asp=Pt=DACH |

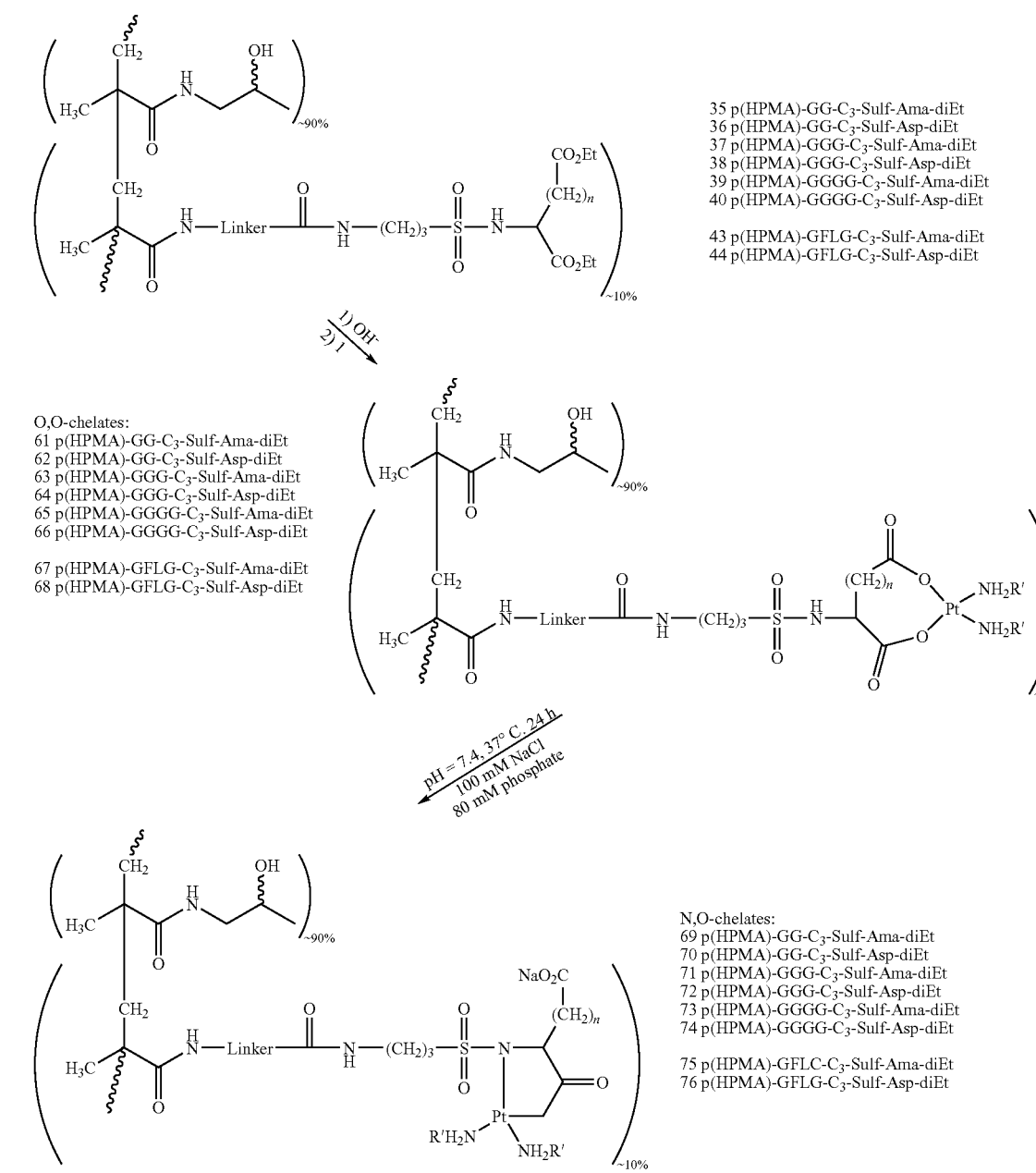

Scheme 10: Preparation of O,O- and N,O-amidomalonate and Amidoaspartate Pt(II)cis-diam(m)ine Chelates.

Biological Evaluation

It will be appreciated that, in any given series of compounds, a spectrum of biological activity will be observed. In its most preferred embodiments, the Pt complexes of this invention will demonstrate therapeutic indices superior to those of cisplatin, carboplatin and/or oxaliplatin. The following procedure may be used to evaluate the compounds of this invention. It is understood that other procedures well-known to those skilled in the art can be employed as well to test against othe tumor types or in other animal models. Such tests are within the scope of this invention.

C57BL/6 mice (10 animals per compound treatment group) were dosed with the amount of compound indicated. The mice were inoculated subcutaneously in the right rear flank with $10^6$ B16F10 murine melanoma cells. Beginning at day 6 post-implantation, tumor size was measured daily using calipers under light Methfurane anesthesia. The mass of the resulting tumor in milligrams was estimated using the formula $W^2(L)/2$ where W is the length of the shorter tumor dimension and L is the length of the longer dimension. Treatment was commenced when the tumor was 50-75 mg or larger. Each animal was followed individually so that Day 1 of treatment for each animal was the day on which that animal's tumor reached the appropriate size. The test compounds were administered intraperitoneally (i.p.) through the tail vein using a volume of 0.2-0.3 mL per 20 grams body weight. The animals were observed and weighed daily prior to dosing to establish the proper dosing volume for that day and such was continued until the end of the study.

Using the above procedure, a number of exemplary compounds of this invention were compared to carboplatin. The results are shown in Table 2 and FIGS. 1-13. As can be seen, most of the compounds tested were at least equivalent to carboplatin and many were superior.

Figure 14:
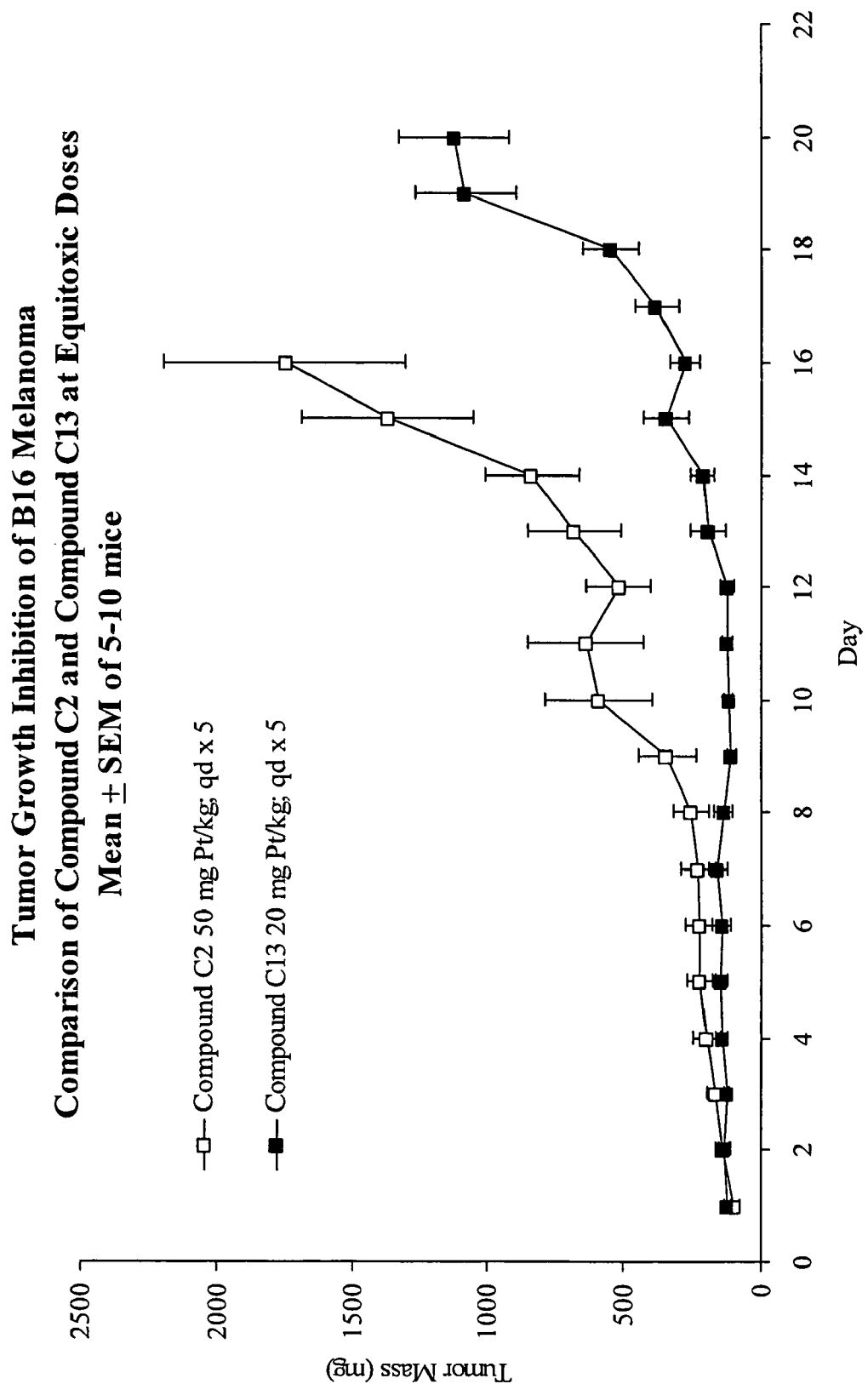
FIG. 14 is a graphical comparison of tumor growth inhibition of two compounds of this invention, C2 and C13 wherein C2 contains only the terminal Pt chelate and C13 contains additional intermediate Pt complexes on the linker.

In addition, a presently preferred compound of this invention, C13, p(HMPA)-GGG-AMA=Pt=DACH, which contains additional Pt chelated on a proportion of the GGG linkers at a site between the terminal Pt chelate and the point of attachment of the linker to the polymeric backbone, was compared to compound C2, p(HMPA)-GFLG-Ama=Pt=DACH, that is believed to contain only terminal Pt chelates. The above B16F10 murine melanoma model was used for this study also. Both compounds were administered at their respective maximum tolerated dosage (MTD). The results are shown in FIG. 14 wherein the points are the mean±SEM (standard error of the mean) of groups of ten mice and are plotted versus day of study (Day 1 being the first day of dosing) until half of each group was lost due to toxicity or sacrifice due to excessive tumor mass (2 g or greater).

As can be seen from the plot, compound C13 exhibits a prolonged delay in tumor growth compared to compound C2 at a lower dose (20 mgPt/kg vs. 50 mgPt/Kg), indicating that compound C13 has greater potency and efficacy than compound C2.

Pharmaceutical Applications and Preparations

A compound of the present invention can be administered as such to a human patient or can be administered in pharmaceutical compositions in which the foregoing materials are mixed with suitable excipient(s). Techniques for formulation and administration of drugs may be found in *Remington's Pharmacological Sciences*, Mack Publishing Co., Easton, Pa., latest edition.

Routes of Administration

Suitable routes of administration may include, without limitation, oral, rectal, transmucosal, intestinal administration, intramuscular, subcutaneous, intramedullary, intrathecal, direct intraventricular, intravenous, intravitreal, intraperitoneal, intranasal, or intraocular. The preferred routes of administration are oral and intravenous.

Alternatively, one may administer the compound in a local rather than systemic manner, for example, via injection of the compound into a tumor as a depot or sustained release formulation.

Compositions/Formulations

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable excipients that facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable excipients well-known in the art. Such excipients enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are normally provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

The compounds of this invention may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

The compositions containing the compound(s) of the invention can be administered for prophylactic or therapeutic treatment. In therapeutic applications, the compositions are administered to a patient suffering from an progressive cancer in an amount sufficient to cure or at least partially arrest the growth or spread of the cancer. An amount adequate to accomplish this is defined as "therapeutically effective amount or dose." Amounts effective for this use will depend on the severity and course of the cancer, previous therapy, the patient's health status and response to the drugs, and the judgment of the treating physician.

In prophylactic applications, compositions containing the compounds of the invention are administered to a patient who is either in remission or whose cancer is not progressing at a dangerous rate. The idea is that, while the cancer may not be eliminated, its progress can be arrested to a sufficient degree to maintain a reasonable quality of life for the patient. Such an amount is defined to be a "prophylactically effective amount or dose." As above, the precise amounts again depend on the patient's state of health, weight, and the like.

As the patient's condition improves, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

Dosage

According to this invention, a therapeutically effective amount of one or more of the compounds of this invention is administered to an organism suffering from a cancer. The proper dosage will depend on the severity and course of the infection, previous therapy, the patient's general health status, his or her response to the drugs, the therapeutic index of the drug, etc., all of which are within the knowledge, expertise and judgment of the treating physician.

In general, a suitable effective dose of the compound of the invention will be in the range of 0.1 to 10000 milligram (mg) per recipient per day, preferably in the range of 20 to 2000 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between about one to four times per day.

Once improvement of the patient's condition is observed, a maintenance dose may be administered if desired by the treating physician. The dosage, frequency, or both, can be reduced as a function of the patient's response to a level at which the improvement persists. When the symptoms have been alleviated to the desired level, treatment may be ceased although some patients may require intermittant treatment on a long-term basis should flare-ups of the symptoms reoccur.

EXAMPLES

The examples provided herein are not intended nor should they be construed as limiting the scope of this invention in any manner whatsoever. In addition, where structures are presented relating to polymeric compounds of this invention, it is understood that the structure show is for illustrative purposes only and is not intended, nor is it to be construed, as limiting the scope of this invention in any manner. For instance, the compound of Example 25 is shown as comprising a poly(N-(2-hydroxypropyl)acrylamide-co-N-((oligopeptidelinker)-

Pt complex)acrylamide) polymer wherein the stable bidentate ligand on the Pt complex is 1R, 2R-diaminocyclohexane and several different N,O and N,N chelates coordinating the Pt species at intermediate locations on the linker, each of these components can be replaced as described and claimed herein to provide other molecules of this invention. Furthermore, the number of Pt chelates shown is not intended, nor is it to be construed, to relate to the actual number or percentage of Pt species in the molecule as actually synthesized. In fact, as is described below, the amount of Pt per gram of compound of example 25 averages 37% more than that which would be expected if the linkers each only carried the one terminal Pt complex. Of course, depending on the synthetic method and amounts of reactants selected, this percentage is also controllably variable to give from 0% to 95% Pt content in excess of that calculated on a one linker/one Pt complex basis. Additionally, as will be apparent to those skilled in the art based on the disclosure and discussion herein, the specific structure of each linker-Pt chelate need not be exactly or only those shown; other N,O and N,N chelates are possible and all such chelates are within the scope of this invention.

Chemicals

Cisplatin, pyridine, ethanol, ethyl acetate, diethyl ether, diethylamino-malonate HCl salt, diethyl N-acetamidomalonate, $AgNO_3$, NaOH, IR,2R-diaminocyclohexane, polyglutamate-Na salt, KI and PBS were supplied by Sigma-Aldrich USA. The solvents used were HPLC grade and the reagents were ACS grade or better. The ion exchange resins, AG 501-X8(D) $H^+$, $HO^-$ forms, AG 50W-X8$H^+$, and Chelex 100 Biotech grade, were supplied by Bio-Rad Laboratories. Class 1 water was obtained using a Milli-Q water system. $K_2PtCl_4$ was supplied by All-Chemie Ltd., Mt. Pleasant, S.C. Filter-aid 289 pulp was obtained from Schleicher and Schuell. Poly(HPMA)-GFLG-ONp, poly(HPMA)-GFLG-Ama-diEt (45 kDa), and poly(HPMA)-GFLG-Ama-diEt (351 kDa) were synthesized by Polymer Laboratories, Shropshire, UK. Aminoacid analysis and MALDI-TOF-MS were performed by Peptide Technologies Corp. Gaithersburg, Md.

Apparatus and Instrumentation

Depending on the scale, 0.2 μm sterile filtrations were performed with either a 25 mm Whatman GD/X PVDF syringe filter, a Steritop media bottle filter with a GP Express membrane from Millipore, or a Millipak inline filter with a PVDF membrane from Millipore. A laminar flow hood with UV light was used for sterile operations. pH was measured with a Beckman Phi-34 pH meter with a gel electrode calibrated at pH 4 for low pH measurements and at pH 10 for high ones. Static electricity in lyophilized solids was neutralized with a Zerostat gun (Aldrich), guided by an electrostatic field meter from SIMCO, Hatfield, Pa. Platinum was analyzed by ICP-OES using a Jobin Yvon JY24 spectrometer on samples and standards diluted to 1-60 ppm in 3% $HNO_3$. Water was determined by Karl Fisher titration using an Aquastar C2000 from EM Science. Elemental analysis for Na, Cl, and P were performed by Desert Analytics, Tucson, Ariz. $^1H$ NMR spectra were obtained on a 400 MHz Unity/Inova system from Varian, Inc. $^{195}Pt$ NMR spectra were obtained on a 300 MHz Mercury system from Varian or a 300 MHz Avance Bruker system. Lyophilizations were performed using a Freezemobile 12EL from Virtus.

Aliquot Purification for Percent O,O'—Pt and N,O—Pt Chelates

The percent of O,O'- and N,O-chelate in timed aliquots of reactions mixtures were determined by removing enough of the reaction mixture (4-15 mL depending on concentration) to give greater than 100 mg of Pt-chelate if only $^{195}Pt$ NMR spectroscopy was to be done or about 200 mg if % Pt, and % $H_2O$ were also to be determined. The aliquots were purified by ultrafiltration using a Centricon Plus-20 centrifugal filter with a 5 kDa Biomax membrane from Millipore. The charged device was spun at the recommended RCF until less than 1 mL remained. The filtrate was discarded, the retentate was diluted with 15-18 mL water and the sample was centrifuged. This was repeated once more, and the retentate was lyophilized to give the sample for analysis.

Platinum Release from PBS

The percent of small platinum species released over time was measured by dissolving about 30 mg of the polymer-platinum conjugate in 15 mL of phosphate buffered saline (10 mM phosphate, 123 mM $Cl^-$) and incubating the solution at 37° C. in a water bath. At indicated times, 2.0 mL aliquots were transferred to a centrifugal filter with a 3 kDa nominal molecular weight cutoff (Centricon YM-3 from Millipore) and spun until >1.5 mL of filtrate had accumulated. The timed filtrates and the original solution were analyzed for platinum by ICP-OES. The percent of small Pt species released was determined using the formula: ((ppm Pt in filtrate)/(ppm Pt in stock solution)) X 100.

Tangential Flow Filtration

At scales larger than about 2 grams, O,O'—Pt and N,O—Pt chelates of polymers were purified by tangential flow filtration (TFF) using membranes with areas of 0.05-0.1 $m^2$ made of Biomax polyethersulfone with a 5 kD nominal molecular weight cutoff. Prior to filtration the system was cleaned and sanitized by pumping 0.1 N NaOH for 30-60 minutes at the recommended flow rate. The caustic was removed and fresh Milli-Q water was circulated until the pH of the retentate and permeate was essentially neutral (pH<8). The permeate flow rate was measured at an inlet pressure of 2.0 bar and an outlet pressure of 0.35 bar. Milli-Q water was also used as the makeup water.

NMR Spectoscopy $^{195}Pt$ NMR spectra were obtained from a filtered 0.70 mL solution in 93/7$H_2O$/$D_2O$ in a 5 mm tube. Enough sample (80-120 mg) was used to give a solution that was >50 mM in platinum. The probe was tuned for each sample. A pulse width of 90 degrees, an acquisition time of 10 msec, a spectral window of 100 kHz and no delay was used. The transmitter was tuned to approximately midway between the O,O'—Pt and N,O—Pt chelates shifts (−1896 ppm for cis-diammine Pt and at −2450 for DACH-Pt). Between 50,000 and 1 million transients were typically required to obtain a sufficient (>35: 1) s/n ratio for the cis-diammine-Pt and DACH=Pt species, respectively. The resulting FID was increasingly left-shifted until a flat baseline was obtained, a 100 Hz line broadening was applied, and a Fourier fill of 2048 was applied before processing. Integral regions were set and the spectrum's baseline was subjected to a spline fit using VNMR software v6.1. The sample was referenced externally to a 100 mM sample of $K_2PtCl_4$ in 95/5$H_2O$/$D_2O$ and 100 mM HCl at −1624 ppm. This was also used to determine the 90 degree pulse width and T1.

$^{13}C$ NMR spectra were obtained using the same sample used for the $^{195}Pt$ NMR. An acquisition time of 0.50 sec, a delay of 3.0 sec, about 70 degree pulse width and 5000-10000 transients were collected and a 3.5 Hz line broadening was applied. A s/n of >100 was typically obtained. Aqueous samples were referenced externally to 1,4-dioxane in 93/7$H_2O$/$D_2O$ at 67.19 ppm. Other samples were referenced to the solvent peak.

¹H NMR spectra were referenced to TMS or TMSP and obtained using standard parameters. Pre-saturation of the HOD signal was often used. Coupling constants (J) are in Hertz.

Example 1

Preparation of Platinating Solutions

A. Preparation of cis-diamminediaquaplatinum (II) Dinitrate (1a) Solution

A suspension of cisplatin (8.996 g, 29.98 mmol), $AgNO_3$ (9.959 g, 58.62 mmol), 3-5 drops of 5% $HNO_3$, and 190 mL of water were stirred overnight at about 23° C. in a foil-covered low actinic media bottle and then heated at 60-65° C. for 3.5 h. After cooling to ambient temperature, the mixture was filtered through a 0.22 μm filter to give a solution of 1a with a pH of approximately 2. A Pt and Ag analysis (ICP-OES) showed that it contained ca. 20,000-25,000 ppm of Pt and 4-14 ppm of Ag. Each preparation was analyzed for Pt, and, just prior to use, it was heated to 55° C. for 5 min then cooled to ambient temperature.

B. Preparation of 1R,2R-DACH-diaquaplatinum (II) Dinitrate (1b) Solution

A suspension of cis-1R,2R-diaminoccylohexane(DACH) dichloroplatinum (II) (2.99 g, 7.86 mmol), $Ag(NO_3)$ (2.6137 g, 15.38 mmol), 2-3 drops of 5% $HNO_3$ and 56 mL of water were stirred overnight at about 23° C. in a foil-covered media bottle then heated at 60-65° C. for 3.5 h. After cooling to ambient temperature the mixture was filtered through a 0.22 μm filter. The pH of the solution was about 2. Pt analysis showed that it contained ca. 15,000-25,000 ppm of Pt. Each preparation was analyzed for Pt and just prior to use it was heated to 55° C. for 5 min then cooled to ambient temperature.

Example 2

Preparation of poly(HPMA)-Ama=Pt=$(NH_3)_2$

A. Preparation of MA-Ama-diEt (2)

A dry 3-neck, 125 mL flask equipped with a thermometer, a stir bar, a pressure equalizing addition funnel, and an Argon inlet was charged with 10.58 g (50.0 mmol) of diethylaminomalonate HCl, 10.62 g (105 mmol) dry triethylamine, and 70 mL of dry $CH_2Cl_2$. After dissolution, the mixture was cooled to 4° C. and 6.53 g (6.11 mL, 50 mmol) of methacryloyl chloride was added dropwise so that the temperature remained below 5° C., and the mixture was then stirred overnight at ambient temperature. White crystals of TEA-HCl were collected by filtration with a second crop being collected after cooling to −20° C. for 3 h. The filtrate was successively washed with 30 mL each of 1 M $NaH_2PO_4$, 5% $NaHCO_3$, and brine. The $CH_2Cl_2$ layer was dried over anhydrous $MgSO_4$ and the solvent removed in vacuo. Dry diethyl ether was added to the residue and the mixture was held at −20° C. overnight. A mass of white crystals were collected and dried to give 6.72 g of 2. These was re-crystallized from MTBE to give 6.2 g of white crystals.

¹H-NMR ($D_2O$): δ 6.8 (br d, 1, NH), 5.83 (s, 1, =$CH_2$), 5.45 (m, 1, =$CH_2$), 5.19 (d, 1, J=6.8 Hz, $CHCO_2Et$), 4.28 (m, 4, $OCH_2CH_3$), 2.00 (s, 3, $CH_3$—(CO)=$CH_2$), and 1.31 (t, 6, J=7.2 Hz, $OCH_2CH_3$); ¹³C-NMR δ 166.4, 138.7, 121.1, 62.6, 56.5, 18.4, and 14.0.

B. Preparation of poly(HPMA)-Ama-diEt (4)

An oven-dried 250 mL pressure bottle with a gas inlet valve was charged with 10.00 g (69.84 mmol) of 2-hydroxypropylmethacrylamide (HPMA), 1.890 g (7.769 mmol) of 2, 83.3 g acetone (HPLC grade), 1.298 g p-nitrophenol (HONp) and a stir bar. The mixture was sparged with Argon for about 30 min, then 0.574 g (0.61 wt %) AIBN was added. After dissolution and sparging for 30 min the bottle and Argon inlet were sealed and the mixture placed at in a water bath at 60° C. After 24 h the mixture was cooled to ambient temperature, vacuum filtered, washed with acetone then diethyl ether, and dried in vacuo to give 8.67 g of very light yellow powder. This was dissolved in absolute EtOH and gently stirred with 2.5 g of IX resin ($H^+$, $OH^-$) for 2 h. The resin was removed and washed. The filtrates were combined and the volume reduced to 100-110 mL in vacuo. Next, 600 mL EtOAc and 200 mL ether were successively added in a slow stream. After stirring overnight, the precipitate that formed was collected by filtration and dried under a rubber dam to give 7.8 g (66%) of poly(HPMA)-AmadiEt 4.

¹H NMR ($D_2O$): δ 4.32 (br m, 4.4, $OCH_2CH_3$), 3.93 (br s, 12.8, $CH_2CH(OH)CH_3$), 3.3-2.9 (br m, 25.4, $CH_2CH(OH)CH_3$), 2.2-1.5 (br m, 21.1, $H_3CC(CO)CH_2$—), 1.4 (s), 1.3 (br t, $OCH_2CH_3$), 1.8-1.2 (br q, $CH_2CH(OH)CH_3$), 0.98 (s, $H_3CC(CO)CH_2$—). This gives a 12:1 ratio of HPMA:2 or 0.5098 mmol AmadiEt/gram of 3.

C. Poly(HPMA)-Ama=Pt=$(NH_3)_2$, O,O-Chelate (5a)

To a 250 mL media bottle equipped with a stir bar, 31 mL of water and 7.00 g (3.57 mmol AmadiEt groups) of 4. After stirring for 15 min, 21 mL water was added, and stirring was continued until a solution was achieved. The pH was raised to 13.2 with 10 mL of 2N NaOH. After 25 min 14 g of IX resin ($H^+$, $OH^-$ form) was added and the pH dropped to 4.5. The pH was raised to 7.4, and 40 mL of a 21,100 ppm Pt (4.33 mmol Pt, 1.2 eq Pt/Ama) solution of cis-diamminediaquaplatinum (II) dinitrate 1 was added. The pH dropped to 4.8, and the mixture was stirred overnight. After stirring overnight the pH dropped to 4.5, and an aliquot was taken for purification and analysis, which revealed 8.32% Pt; 3.5% $H_2O$; % Pt Release at 3 & 24 h, 3.4%, 27.9%; 0.39% free Pt.

¹⁹⁵Pt NMR (93/7$H_2O$/$D_2O$): δ −1720 (br s).

After the aliquot was collected, 2.76 g of Chelex resin was added and the mixture stirred for 90 min. The pH rose to 5.5, the resin was removed by sterile filtration (Millipore Steritop) and the solution (290 mL) was made 100 mM in NaCl, and 80 mM in phosphate by addition of 1.695 g (29.0 mmol) NaCl, 0.681 g $NaH_2PO_4.H_2O$, and 4.896 g $Na_2HPO_4.7H_2O$. The solution was heated to 37° C. and placed in an oven at 38° C. for 24 h. The solution was purified by TFF and lyophilized to give 5.49 g of 5a as an off-white solid: 6.1% Pt, 7.2% $H_2O$; % Pt Release at 3 & 24 h, 4.1%, 23.8%; 0.57% free Pt, ¹⁹⁵Pt NMR (93/7$H_2O$/$D_2O$): δ −1710 (v br s, noisy) and no peak near −2055 ppm.

¹³C NMR (93/7$H_2O$/$D_2O$): δ 175.1, 174.9, 174.7, 169.5, 168.9, 61.3, 61.1, 58.1, 57, 54, 49.5, 47.3, 42.7, 40.8, 40.4, 15.7, 15.5, 13.4, and 12.0; $M_w$=23.7 kDa, $M_n$=15.6 kD.

Example 3

Preparation of poly(HPMA)-GG-Ama=Pt=$(NH_3)_2$, 38 kDa

A. Poly(HPMA)-GG-Ama-diEt (10)

An oven-dried foil-covered 250 mL media bottle equipped with a stir bar and cap with a gas inlet valve and bubbler was charged with 1.80 g (5.04 mmol) of MA-GG-Ama-diEt 7, 6.49 g (45.33 mmol) of HPMA, 0.841 g (6.04 mmol) of p-nitrophenol (HONp), and 46.7 g of HPLC-grade acetone. The cap with Argon bubbler and valve was replaced and the mixture was stirred until dissolution then sparged again with Argon for 30 min. The cap was removed, and 0.40 g (0.398 mmol) of AIBN dissolved in 5 mL of acetone was added by syringe. The syringe was rinsed with 5 mL of acetone in 1 mL increments that were each added to the solution. The reaction mixture was sparged with Ar for 1 h more then immersed in a 50° C. water bath for 48 h. After cooling to ambient temperature the polymer was filtered through a medium glass frit, washed three times with 50 mL of diethyl ether and dried under a rubber dam to give 7.1 g of a pale yellow solid. The solid was dissolved in 35 mL of absolute EtOH then precipitated with 250 mL of dry ethyl acetate. After stirring for 1 h, the precipitate was collected, washed three times with 50 mL of diethyl ether, and dried under a rubber dam overnight to give 7.0 g of 10 as a white solid: 0.608 mmol Ama-diEt/g polymer.

$^1$H NMR ($D_2O$): δ 4.3 (br q, 4H, $OCH_2CH_3$), 4.1 (br.s., 2H, $NHCH_2C=O$), 3.9 (br.s., $NHCH_2CHOHCH_3$), 3.3-2.9 (m, $NHCH_2CHOHCH_3$, $CH_2$ of glycines), 2.25-1.6 (m, $CH_2$ of polymer backbone), 1.3 (t, $OCH_2CH_3$), 1.2 (s, $NHCH_2CHOHCH_3$), 1.0 (s, $CH_3$ of polymer backbone). The $^1$H NMR spectrum of this material showed that it contained no small molecules except for <1% each of EtOH and EtOAc.

B. Preparation of poly(HPMA)-GG-Ama=Pt($NH_3$)$_2$ (O,O Chelate) (45)

A 100 mL media bottle equipped with a stir bar was charged with 2.0 g of 10 (1.2 mmol), and 17 mL water. The solution was stirred for 2 h until the polymer dissolved. 2.9 mL of 2 M NaOH was added and the pH was maintained at 12.6 for 2 h. 2.0 g of Bio-Rex MSZ 501 D resin was added and the solution stirred until the pH fell to 7. The resin was filtered, and the pH of the filtrate was raised to 7.4 with 2N NaOH. 9.75 mL (1.4 mmol Pt) of a 28,032 ppm solution of 1a was then added. The pH was adjusted to 5.4 with 2 M NaOH and the solution was stirred for 8 h, then 0.877 g of Chelex 100 resin was added. After stirring for 2 h, the resin was removed by filtration and 10 mL (200 mg of polymer) was taken for $^{195}$Pt NMR analysis. The aliquot was purified by centrifugal ultrafiltration then lyophilized to give 45.

$^{195}$Pt NMR (93/:7$H_2O$/$D_2O$): δ 1731 (s, 92%-O,O-chelate), −2051 (s, 8%-N,O-chelate).

$^1$H NMR ($D_2O$): δ 7.8 (br.d., NH), 6.0 (s), 4.2 (s), 4.0 (s), 3.2 (d, $CH_2$— of HPMA side chain), 1.8 (d, $CH_2$— of polymer backbone), 1.2 (s, $CH_3$ of HPMA side chain), 0.9 (s, $CH_3$ of polymer backbone).

C. Preparation of poly(HPMA)-GG-Ama=Pt($NH_3$)$_2$ (N,O Chelate) (53a)

To the remaining 90 mL of the above solution, 0.5260 g (9.01 mmol) NaCl, 0.2114 g $NaH_2PO_4.H_2O$ (1.53 mmol), and 1.519 g $Na_2HPO_4.7H_2O$ (6.13 mmol) were added and stirred until dissolved. The pH was adjusted to 7.4 and the solution was incubated at 38° C. for 24 h. Two 10 mL aliquots were taken at 8.5 h, and 21.5 h. The aliquots and remaining polymer were purified by centrifugal ultrafiltration and subjected to $^{195}$Pt NMR.

$^{195}$Pt NMR of 8.5 hr chelate conversion aliquot (93/7$H_2O$/$D_2O$): δ −1731 (s, 24.4%-O,O-chelate of Pt($NH_3$)$_2$), −2051 (s, 75.6%-N,O-chelate of Pt($NH_3$)$_2$).

$^{195}$Pt NMR of 21.5 h chelate conversion aliquot (93:7$H_2O$: $D_2O$) δ −2051 (>95%-N,O chelate of Pt($NH_3$)$_2$).

$^{195}$Pt NMR of 24 hr chelate conversion aliquot (93:7$H_2O$: $D_2O$): δ −2051 (>95%-N,O Chelate of Pt($NH_3$)$_2$).

$^1$H NMR of 24 h chelate conversion aliquot ($D_2O$): δ 4.8 (s HOD), 4.2 (s), 4.0 (s), 3.2 (d, $CH_2$— of HPMA side chain), 1.8 (d, $CH_2$— of polymer backbone), 1.2 (s, $CH_3$ of HPMA side chain), 0.9 (s, $CH_3$ of polymer backbone). SEC $M_p$ 33.1 kD, $M_w$ 38.3 kD, $M_n$ 18.5 kD, and PDI=2.09.

Example 4

Preparation of poly(HPMA)-GG-Ama=Pt=1R,2R-DACH, 38 kDa (53b)

A 2.0 g sample of poly(HPMA)-GG-Ama-diEt 10 was hydrolyzed and treated as described in Example 3B to give a solution of poly(HPMA)-GG-Ama($CO_2Na$)$_2$ at pH=7.4. To this, 10.8 mL (1.4 mmol Pt) of a 24,941 ppm solution of PtDACH($H_2O$)$_2^{2+}$ 1 b was added. The pH was adjusted to 5.4 with 2 M NaOH, and the solution was stirred for 8 h. Chelex 100 resin (0.865 g) was added, the solution stirred for 2 h and then filtered to give 60 mL of filtrate after washing the resin. The filtrate was made 110 mM in NaCl and 80 mM in phosphate by addition of 0.3803 g (6.52 mmol) NaCl, 0.1336 g (0.97 mmol) $NaH_2PO_4.H_2O$, and 1.028 g (3.88 mmol) $Na_2HPO_4.7H_2O$. The solution was incubated at 38° C. for 24 h, then purified by centrifugal ultrafiltration and lyophilized to give 53b.

$^{195}$Pt NMR of polymer after 24 h chelate conversion (93: 7$H_2O$: $D_2O$): δ −22295 (>95%-N,O Chelate of PtDACH). $^1$H NMR ($D_2O$) δ 6.3 (s, amide protons) 4.8 (s HOD), 4.2 (s), 4.0 (s), 3.2 (d, $CH_2$— of HPMA side chain), 1.8 (d, $CH_2$— of polymer backbone), 1.2 (s, $CH_3$ of HPMA side chain), 0.9 (s, $CH_3$ of polymer backbone).

SEC $M_p$ 31.9 kD, $M_w$ 40.3 kD, $M_n$ 21.6 kD, and PDI=1.87.

Example 5

Preparation of poly(HPMA)-GG-Asp=Pt=($NH_3$)$_2$, 47 kDa

A. Preparation of MA-GG-Asp-diEt (8)

An oven-dried 500 mL media bottle wrapped in foil and equipped with a stir bar, septum cap, and drying tube was charged with MA-GG-OH (6, 1.9520 g, 9.6159 mmol), Asp-diEt HCl (4.4292 g, 19.62 mmol), EDC (4.7025 g, 24.53 mmol) and HOBt (0.1463 g, 0.9553 mmol) in an inert atmosphere. Dry pyridine (40 mL) was added and the mixture stirred for 17 h. The pyridine was removed in vacuo and three 10 mL portions of toluene were added. The solution was shaken for a few minutes and the toluene was removed in vacuo to yield a viscous orange residue. The residue was dissolved in $CHCl_3$ (100 mL), transferred to a 1 L round bottomed flask with 70 g Si-gel, and the $CHCl_3$ removed in vacuo. The residue was put in a 150 mL coarse frit loaded with 1 inch of fresh silica gel and eluted with 4×300 mL of acetone. The first three fractions were combined and concentrated to dryness. The residue was recrystallized from absolute EtOH, at 0° C. for 2 h. The precipitate was collected, washed with $Et_2O$, recrystallized twice from EtOAc, washed with diethyl ether and dried in vacuo to give 0.85 g of 8 as a white powder.

$^1$H NMR ($CDCl_3$): δ 7.20, (br s, 1, NH), 7.17, (br s, 1, NH), 6.89, (br s, 1, NH), 5.81 (s, H, vinyl), 5.39 (s, H, vinyl), 4.84 (dt, 1, αCH Asp), 4.25-3.97 (m: 8, 2-$CH_2$-gly, 2-$OCH_2CH_3$), 2.90 (2 pr AB d, 2, $CH_2$-Asp), 1.98 (s, 3, $CCH_3$), 1.26 (m: 2 overlapping t, 6, —$OCH_2CH_3$).

B. Preparation of poly(HPMA)-GG-Asp-diEt, about 47 kDa (11)

An oven-dried 250 mL media bottle equipped with a magnetic stir bar and covered in aluminum foil was charged with 5.2 g (36.4 mmol) HPMA monomer 3, 1.5 g (4.0 mmol) 8 (MA-GG-Ama-diEt), 0.6742 g (4.84 mmol) HONp, and 35.8 g acetone. The bottle was capped and the monomers were stirred under a bubbling flow of Argon until dissolved and the solution was further purged for 30 minutes. 0.323 g (1.97 mmol) of azobisisobutyronitrile (AIBN) was dissolved in 5 mL of acetone and added via syringe. The syringe was rinsed with 5 mL of acetone in 1 mL increments that were each added to the solution. The solution was purged with Argon for 1 h after the addition of the AIBN. The bottle was immersed in a 50° C. $H_2O$ bath for 24 h, then removed and cooled to room temperature. The foil was removed revealing the polymer as a pale yellow precipitate occupying nearly the entire volume of the acetone. The polymer was filtered through a medium glass frit. The filter cake was washed three times with 50 mL of diethyl ether and dried under a rubber dam to give 6.8 g of a pale yellow solid. The solid was dissolved in 700 mL of absolute EtOH and stirred for 3 h. The product was precipitated with 700 mL of dry ethyl acetate. The mixture was stirred for 1 h then filtered through a coarse glass frit. The filter cake was washed three times with 100 mL of diethyl ether. The filter cake was dried under a rubber dam for three hours and under vacuum overnight. The product was collected as 6.11 g of a white solid. The $^1$H NMR spectrum of this material showed that it contained peaks characteristic of both HPMA and MA-Ame and no small molecules except for <1% each of EtOH and EtOAc.

$^1$H NMR ($D_2O$) δ 4.2 (br q, $OCH_2CH_3$), 4.1 (br s, $NHCH(CO_2Et)_2$), 3.9 (br.s., $NHCH_2CHOHCH_3$), 3.8 (br.s., $NHCH_2C(O)$), 3.3-2.9 (m, $NHCH_2CHOHCH_3$), 2.2-1.6 (m, $CH_2$ of polymer backbone), 1.3 (t, $OCH_2CH_3$), 1.2 (s, $NHCH_2CHOHCH_3$), 1.0 (s, $CH_3$ of polymer backbone).

Example 6

Preparation of poly(HPMA)-GG-Asp=Pt=1R,2R-DACH, 35-45 kDa

Poly(HPMA)-GG-Asp=Pt=1R,2R-DACH, 35-45 (54b) was prepared by treating poly(HEMA)-GG-Asp-diEt (11) as described in example 4.

Example 7

Preparation of poly(HPMA)-GG-ONp, 23 kDa

A. Preparation of poly(HPMA)-GG-ONp (12) about 23 kDa

An oven-dried 500 mL media bottle equipped with a stir bar and covered with aluminum foil was charged with 34.31 g (239.6 mmol) HPMA monomer, 7.0 g (21.8 mmol) methacroyl-gly-gly-p-nitrophenol (MA-GG-ONp, 9), and 272.6 g acetone. The bottle was capped and then sparged with Argon for 30 min after dissolution. 1.99 g (12.11 mmol) of AIBN dissolved in 5 mL of acetone was added via syringe. The syringe was rinsed with 5 mL of acetone in 1 mL increments that were each added to the solution. The solution was sparged with argon for 45 min. The bottle was sealed, immersed in a 50° C. $H_2O$ bath for 48 h., and then allowed to cool to ambient temperature. The yellow reaction mixture was transferred to 200 mL centrifuge bottles and the solid was isolated by centrifugal sedimentation at 3840 RCF for 10 min. The liquid was decanted and the solid was washed with 50 mL of diethyl ether then centrifuged and decanted as above. This washing was repeated two more times. After drying in vacuo, 34.31 g of a cream-colored solid was obtained. The solid was dissolved in 140 mL of absolute EtOH and then precipitated by addition of 1.5 L of dry ethyl acetate to the stirring mixture. After 1 h, the solid was isolated by centrifugal sedimentation and washed three times with 100 mL of diethyl ether. After drying in vacuo overnight 31.65 g of 12 was obtained as a white solid.

$^1$H NMR (DMSO-$d_6$): δ 8.7 (s-amide NH), 8.3 (d, ONp aromatic H), 7.4 (d-ONp aromatic H), 4.8 (s, $CH_2CHOHCH_3$), 4.3 (s, $CH_2$— of glycine), 3.7 (s, $CH_2CHOHCH_3$), 3 (s, $CH_2CHOHCH_3$), 1.5 (br, m, $CH_2$ of polymer backbone), 1.0 (s, $CH_3$ of polymer backbone), 0.9 (d, $CH_2CHOHCH_3$); No small molecules except for <1% each of EtOH and EtOAc.

Example 8

Preparation of 3-aminopropylsulfonamidomalonate, diethyl ester, HCl (17)

A. 3-Chloropropanesulfonyl Aminomalonate Diethyl Ester (13)

To a suspension of diethylaminomalonate HCl (24.34 g, 0.115 mol) in 400 mL of chloroform was added 50 mL of triethylamine to give a clear solution. A solution of 3-chloropropanesulfonyl chloride (21.25 g, 0.12 mol) in 100 mL of chloroform was added in a steady stream. The resulting mixture was refluxed for 3 h. The reaction mixture was cooled gradually to ambient temperature and then extracted with 1 N HCl (2×300 mL) and with water (2×300 mL). The organic phase was dried over anhydrous $Na_2SO_4$ and solvent was removed in vacuo to give) 29.05 g of 13.

$^1$H NMR ($CDCl_3$): δ 1.31 (t, 6, $OCH_2CH_3$), 2.33 (m, 2, $CH_2$), 3.28 (t, 2, $CH_2$), 3.68 (t, 2, $CH_2$), 4.26 (m, 4, $OCH_2CH_3$), 4.84 (d, 1, CH), 5.59 (d, 1, NH). $^{13}$C NMR ($CDCl_3$) δ 13.6, 26.3, 42.5, 51.2, 58.5, 62.7, 165.9.

B. 3-Iodopropanesulfonyl Aminomalonate Diethyl Ester (15)

To a solution of NaI (34.47 g, 0.23 mol) in 400 mL of acetone was added 3-chloropropanesulfonyl aminomalonate diethyl ester 13 (29.05 g, 0.092 mol). The reaction mixture was refluxed for 6 h and then cooled to ambient temperature. NaCl was removed by filtration. The filtrate was stripped in vacuo, the residue was dissolved in 300 mL of dichloromethane and then it was washed with aqueous sodium thiosulfate (3×250 mL) and water (3×250 mL). The organic layer was dried over $Na_2SO_4$ and the solvent was removed in vacuo to give 29.07 g of the desired product.

$^1$H NMR ($CDCl_3$): δ 1.31 (t, 6, $OCH_2CH_3$), 2.36 (m, 2, $CH_2$), 3.24 (t, 2, $CH_2$), 3.31 (t, 2, $CH_2$), 4.26 (m, 4, $OCH_2CH_3$), 4.85 (d, 1, CH), 5.98 (d, 1, NH). $^{13}$C NMR ($CDCl_3$) δ 3.00, 13.7, 27.1, 54.5, 58.6, 62.7, 165.9.

C. 3-Azidopropanesulfonyl Aminomalonate Diethyl Ester (17)

Method A: to a solution of 3-iodopropanesulfonylaminomalonate diethyl ester (29.00 g, 0.071 mol) in 300 mL of $CCl_4$, a solution of sodium azide (11.38 g, 0.175 mol) in 50 mL of water and trioctylmethylammonium chloride were added. The resulting mixture was stirred at 80° C. for 16 h. The reaction mixture was allowed to cool to ambient temperature. The aqueous layer was separated and washed with dichloromethane (100 mL). The organic layers were combined and washed with water (3×100 mL) then dried over anhydrous $Na_2SO_4$. The solvent was then removed in vacuo to give 18.94 g of 17.

Method B: to a solution of 3-chloropropanesulfonylaminomalonate diethyl ester (44.21 g, 0.14 mol) in 200 mL of DMF was added sodium azide (29.25 g, 0.45 mol). The reaction mixture was stirred at 90° C. for 16 h then cooled to ambient temperature. The mixture was poured into ice water and extracted with dichloromethane. The combined organic layers were washed with brine and dried over anhydrous sodium sulfate. The solvent was removed in vacuo to give 28.02 g of 17.

¹H NMR (CDCl₃): δ 1.31 (t, 6H, CH₃), 2.13 (m, 2H, CH₂), 3.21 (t, 2H, CH₂), 3.50 (t, 2H, CH₂), 4.22-4.35 (m, 5H, CH₂ and CH), 6.17 (d, 1H, NH). ¹³C NMR (CDCl₃) δ 13.7, 22.9, 50.9, 53.3, 58.4, 62.4, 165.8.

D. 3-Aminopropanesulfonyl Aminomalonate Diethyl Ester (19)

A solution of 3-azidopropanesulfonyl aminomalonate diethyl ester (17, 27.60 g, 0.086 mol) in ethanol (70 mL) and 1 g of palladium on carbon (10%, wt) were placed in a Parr hydrogenation apparatus. The mixture was put under 60 psi of hydrogen for 8 h. The hydrogen was refilled every 2 hours. The mixture was then filtered through Celite. A solution of 1 N HCl in ethanol (10 mL) was added and the solvent was removed in vacuo. The residue was purified by column chromatography on Al₂O₃ using CH₂Cl₂/MeOH (4/1, v/v) as eluant to give 26.84 g of 19.

¹H NMR (CDCl₃): δ 1.30 (t, 6, CH₃), 2.12 (m, 2, CH₂), 3.21 (t, 2, CH₂), 3.50 (t, 2, CH₂), 4.26 (m, 4, CH₂), 4.84 (d, 1, CH), 6.09 (d, 1, NH), 8.29 (br.s, 2, NH₃). ¹³C NMR (CDCl₃) δ 13.6, 26.3, 42.5, 51.2, 58.5, 62.7, 165.9.

Example 9

Preparation of 3-aminopropylsulfonamidoaspartate, diethyl ester, HCl

A. 3-Chloropropanesulfonyl Aspartate Diethyl Ester (14)

To a suspension of diethylaspartate hydrochloride (25.00 g, 0.11 mol) in 250 mL of chloroform was added 50 mL of triethylamine to give a clear solution. A solution of 3-chloropropanesulfonyl chloride (21.25 g, 0.12 mol) in 50 mL chloroform was added in a continuous stream, then the mixture was refluxed for 3 h. The reaction mixture was allowed to cool gradually to ambient temperature and then it was washed with 1 N HCl (2×300 mL) and water (2×300 mL). The organic phase was dried over anhydrous Na₂SO₄ and the solvent was removed in vacuo to give 30.62 g of 14.

¹H NMR (CDCl₃): δ 1.22-1.31 (2 t, 6, OCH₂CH₃), 2.30 (m, 2, CH₂), 2.89-3.04 (2 prAB d, 2, CH₂), 3.28 (t, 2, CH₂), 3.69 (t, 2, CH₂), 4.13-4.27 (m, 4, OCH₂CH₃), 4.39 (m, 1, CH), 5.89 (d, 1, NH). ¹³C NMR (CDCl₃) δ 13.8, 13.8, 26.5, 37.7, 42.7, 50.7, 52.2, 170.7, 10.4.

B. 3-Iodopropanesulfonyl Aspartate Diethyl Ester (16)

To a solution of NaI (11.44 g, 75.0 mmol) in 250 mL of acetone was added 3-chloropropanesulfonylaspartate diethyl ester (14, 10.00 g, 0.03 mol). The reaction mixture was refluxed for 6 h and then cooled to ambient temperature. The NaCl precipitate removed by filtration and the acetone was removed in vacuo. The residue was dissolved in 150 mL of CH₂Cl₂ and washed successively with a sodium thiosulfate solution (3×100 mL) and water (3×100 mL). The organic layer was dried over Na₂SO₄, and the solvent was removed in vacuo to give 9.78 g of the desired product.

¹H NMR (CDCl₃): δ 1.29 and 1.31 (two t, 6, OCH₂CH₃), 2.35 (m, 2, CH₂), 2.89-3.04 (d of AB d, 2, CH₂), 3.21 (t, 2, CH₂), 3.31 (t, 2, CH₂), 4.14-4.27 (m, 4, CH₂CH₃), 4.35 (m, 1, CH), 5.50 (d, 1, NH). ¹³C NMR (CDCl₃) δ 3.0, 14.1, 27.4, 38.0, 52.5, 54.4, 61.4, 62.4, 170.5, 170.6.

C. 3-Azidopropanesulfonyl Aspartate Diethyl Ester (18)

Method A: to a solution of 3-iodopropanesulfonylaspartate diethyl ester (5.50 g, 0.013 mol) in 100 mL of CCl₄, a solution of NaN₃ (2.11 g, 0.325 mol) in 30 mL of water and trioctylmethylammonium chloride (65 mg) were added. The resulting mixture was stirred at 80° C. for 16 h. The reaction mixture was allowed to cool to ambient temperature and the phases were separated. The aqueous layer was washed with CH₂Cl₂ (50 mL) and the combined organic layers were washed with water (3×50 mL), then dried over anhydrous Na₂SO₄. The solvent was removed in vacuo to give 3.60 g of 18.

Method B: to a solution of 3-chloropropanesulfonylaspartate diethyl ester (17.50 g, 0.053 mol) in DMF (250 mL) was added 10.4 g (0.16 mol) of sodium azide. The reaction mixture was stirred at 90° C. for 16 h then cooled to room temperature. The mixture was chilled to 4° C. and extracted with dichloromethane. The combined organic layers were washed with brine and dried over anhydrous NaSO₄. The solvent was removed in vacuo to give 13.29 g of 18.

¹H NMR (CDCl₃): δ 1.26 and 1.28(2 t, 6H, CH₃), 2.12 (m, 2H, CH₂), 2.87-3.02 (2 prAB d, 2, CH₂), 3.20 (t, 2, CH₂), 3.49 (t, 2, CH₂), 4.13-4.26 (m, 4, CH₂), 4.39 (m, 1, CH), 5.90 (d, 1, NH).

¹³C NMR (CDCl₃) δ 13.5, 13.6, 23.8, 37.6, 49.2, 50.3, 52.1, 60.8, 61.8, 170.1, 170.3.

D. 3-Aminopropanesulfonyl Aspartate Diethyl Ester (20)

A solution of 3-azidopropanesulfonyl aspartate diethyl ester (3.60 g, 0.01 mol) in ethanol (50 mL) and Pd/C (250 mg) were placed in a Parr hydrogenation apparatus. The mixture was put under 60 psi of H₂ for 8 h with the H₂ being refilled every 2 hours. The mixture was filtered through Celite, then 1 N HCl in ethanol (2 mL) was added to the filtrate. The solvent was removed in vacuo. The residue was purified by column chromatography on Al₂O₃ using CH₂Cl₂/MeOH (4/1, v/v) as eluant to give 3.19 g of 20.

¹H NMR (DMSO): δ 1.15-1.21 (d of t, 6, CH₃), 1.98 (m, 2, CH₂), 2.72-2.77 (d of AB d, 2, CH₂), 2.85 (t, 2, CH₂), 3.18 (t, 2, CH₂), 4.03-4.13 (m, 4, CH₂), 4.26 (m, 1, CH), 8.00 (d, 1, NH), 8.35 (br.s, 3, NH₃).

Example 10

Preparation of Gly-Gly-3-aminopropylsulfonamido-malonate, diethyl ester, TFA (23)

To a stirred solution of t-BOC-Gly-Gly-OH (9.2896 g, 0.0400 mol) and HOBt (6.1260 g, 0.0400 mol) in DMF (18 mL) at 0° C. was added DCC (8.2532 g, 0.0400 mol). The mixture was stirred at 0° C. for 45 min. In a separate flask, TEA (5.0595 g, 0.0500 mol) was added to a mixture of 3-amino-propanesulfonamido-malonate diethyl ester HCl salt (19, 13.3136 g, 0.0400 mol) and 10 mL DMF. This mixture was stirred at room temperature for 10 min, filtered and the filtrate placed under high vacuum in a 50 mL flask for 5 min. The DMF solution of 3-aminopropanesulfonamidoaspartate diethyl ester with TEA was then added to the prestirred t-Boc-Gly-Gly-OH/HOBt/DCC mixture. The resulting mixture was stirred at 0° C. for 2 h, allowed to come to ambient temperature, and stirred for an additional 6 h. The mixture was filtered, and the filtrate was poured into 300 mL of water and extracted with CH₂Cl₂ (3×400 mL). The combined organic layers were washed with brine (3×300 mL) and water (3×300 mL), dried over anhydrous Na₂SO₄, and filtered. The solvent was removed in vacuo. The residue was purified by Si-gel column chromatography using CH₂Cl₂/Acetone, 99/1 to 0/100 as eluant to give 9.10 g of product as a white solid.

¹H NMR (CDCl₃): δ 7.47 (t, 1H, NH), 7.35 (t, 1H, NH), 6.24 (d, 1H, NH), 5.83 (d, 1H, NH), 4.83 (d, 1H, CH), 4.20-4.27 (m, 4H, OCH₂CH₃), 3.91 (d, 2H, Gly-CH₂), 3.83 (d, 2H, Gly-CH₂), 3.37 (m, 2H, CH₂), 3.16 (t, 2H, CH₂), 2.28 (m, 2H, CH₂), 1.44 (s, 9H, t-Butyl), 1.32 (t, 6H, CH₃).

A solution of t-BOC-Gly-Gly-3-aminopropylsulfonamidomalonate diethyl ester (7.7880 g, 0.0200 mol), in 40 mL of TFA/DCM 1/1 was stirred under an Argon atmosphere. After 2 h, TLC analysis (DCM/MeOH, 9/1, v/v) indicated the reaction was complete, and the solvent was removed in vacuo. The residue was triturated with 5 mL diethyl ether, filtered, and the precipitate dried in vacuo to give 7.66 g of 23.

$^1$H NMR (CDCl$_3$): δ 8.53 (t, 3H, NH$_2$ TFA salt), 7.66 (t, 1H, NH), 7.61 (t, 1H, NH), 6.44 (d, 1H, NH), 4.36 (d, 1H, CH), 4.19-4.26 (m, 4H, CH$_2$), 3.91 (d, 2H, CH$_2$), 3.80 (d, 2H, CH$_2$), 3.37 (m, 2H, CH$_2$), 3.16 (t, 2H, CH$_2$), 2.33 (q, 2H, CH$_2$), 1.29 (t, 6H, CH$_3$).

Example 11

Preparation of
Gly-Gly-3-aminopropylsulfonamido-aspartate,
diethyl ester, TFA (24)

To a stirred solution of t-BOC-Gly-Gly-OH (3.7158 g, 0.0160 mol) and HOBt (2.4504 g, 0.0160 mol) in DMF (15 mL) at 0° C. was added DCC (3.3013 g, 0.0160 mol). The mixture was stirred at 0° C. for 45 min. In a separate flask, TEA (2.024 g, 0.200 mol) was added to a mixture of 3-aminopropanesulfonamido-aspartate diethyl ester HCl salt (20, 5.5650 g, 0.0160 mol) and 3 mL of DMF. The mixture was stirred at room temperature for 10 min, filtered and the filtrate placed under high vacuum in a 50 mL flask for 5 min. After 45 min of stirring the t-Boc-Gly-Gly-OH/HOBt/VDCC mixture, the DMF solution of 3-aminopropanesulfonamidoaspartate diethyl ester with TEA was added. The resulting mixture was stirred at 0° C. for 2 h, allowed to come to ambient temperature, and stirred for an additional 10 h. The mixture was filtered, and the filtrate was poured into 300 mL of water and extracted with CH$_2$Cl$_2$ (3×200 mL). The combined organic layers were washed with brine (3×100 mL) and water (3×100 mL), dried over Na$_2$SO$_4$, and filtered. The solvent was removed in vacuo. The residue was purified by Si-gel column chromatography using CH$_2$Cl$_2$/acetone, 99/1 to 0/100, as eluant to give 4.80 g of product as a colorless oil.

$^1$H NMR (CDCl$_3$): δ 7.45 (t, 1H, NH), 7.34 (t, 1H, NH), 6.25 (d, 1H, NH), 5.82 (t, 1H, NH), 4.43 (m, 1H, CHCH$_2$), 4.14-4.24 (m, 4H, OCH$_2$CH$_3$), 3.93 (d, 2H, Gly-CH$_2$), 3.83 (d, 2H, Gly-H$_2$), 3.37 (m, 2H, CH$_2$), 3.16 (t, 2H, CH$_2$), 2.88-3.02 (d of a prAB d, 2H, CH$_2$, J=4.5, J=15), 2.18 (m, 2H, CH$_2$), 1.44 (s, 9H, t-Butyl), 1.23-1.30 (m, 6H, CH$_3$).

$^{13}$C NMR (CDCl$_3$) 6170.8, 170.5, 170.4, 169.3, 156.3, 80.0, 62.1, 61.1, 52.4, 50.9, 44.1, 42.8, 37.8, 37.4, 28.1, 23.5, 13.9, 13.8.

A solution of t-BOC-Gly-Gly-3-aminopropylsulfonamidoaspartate diethyl ester (4.80 g, 0.0091 mol), in 40 mL of TFA/DCM 1/1 was stirred under an argon atmosphere. After 2 h, TLC analysis (DCM/MeOH, 9/1, v/v) indicated the reaction was complete, and the solvent was removed in vacuo. The residue was triturated with 5 mL of diethyl ether, filtered, and the precipitate dried in vacuo to give 4.70 g of 24.

$^1$H NMR (CDCl$_3$): δ 8.53 (t, 2H, NH$_2$), 7.66 (t, 1H, NH), 7.61 (t, 1H, NH), 6.44 (d, 1H, NH), 4.36 (m, 1H, CH), 4.09-4.16 (m, 4H, CH$_2$), 3.94 (d, 2H, CH$_2$), 3.83 (d, 2H, CH$_2$), 3.37 (m, 2H, CH$_2$), 3.16 (t, 2H, CH$_2$), 2.88-3.02 (d of a prAB d, 2H, CH$_2$, J=4.5 Hz, J=15 Hz), 2.03 (m, 2H, CH$_2$), 1.20-1.29 (m, 6H, CH$_3$).

$^{13}$C NMR (CDCl$_3$) δ 171.5, 170.8, 170.4, 167.6, 164.0, 117.5, 62.5, 61.4, 60.5, 52.4, 50.9, 42.8, 37.8, 37.4, 23.4, 13.8, 13.7.

Example 12

Preparation of Gly-Ama-diEt, TFA Salt (23)

A mixture of 324.98 g of sodium bicarbonate and 1500 mL of water was added slowly to diethylaminomalonate hydrochloride (740.78 g, 3.50 mol) in a 4 L Erlenmeyer flask. Dichloromethane (1000 mL) was added after the addition of sodium bicarbonate/water mixture was completed. The resulting two phase mixture was vigorously stirred for 15 min and then separated in a separatory funnel. The organic layer was collected, 500 mL dichloromethane was added to the aqueous layer and the mixture was stirred for 15 min and then allowed to separate. The pH of aqueous layer was 7.8. The combined dichloromethane layers were dried over anhydrous sodium sulfate and filtered. Dichloromethane was removed in vacuo until the volume was reduced to about 600 mL. This solution was placed into a 2000 mL 3-neck round-bottom flask, t-BOC-Gly-OH (569.34 g, 3.25 mol) was added and the resulting mixture was stirred and cooled to 10° C. DCC (670.57 g, 3.25 mol) was dissolved in 400 mL DCM and added via addition funnel to the vigorously stirred diethylaminomalonate/t-BOC-Gly-AME mixture with the temperature being maintained below 25° C. The DCC addition was complete in about 2.5 hrs. After all of DCC was added, the mixture was stirred for an additional 45 min in a salt/ice bath to bring the temperature of the mixture to 5° C. The cooling bath was removed and the reaction mixture stirred for an additional 4 hrs at ambient temperature and then allowed to sit overnight.

The white precipitate that formed was removed by filtration and washed with 100 mL of dichloromethane. The filtrate and DCM wash were combined and the solvent removed in vacuo to give a yellow crystalline material which was dried under vacuum to give 881.8 g of product.

$^1$H NMR (CDCl3): δ 7.44 (d, 1H, NH), 5.69 (t, 1H, NH), 5.19 (d, 1H, CH), 4.27 (m, 4H, CH$_2$), 3.90 (d, 2H, CH$_2$), 1.46 (s, 9H, CH$_3$), 1.29 (t, 6H, CH$_3$).

To a solution of t-BOC-Gly-Ama, diEt (985.2 g, 2.96 mol) in 770 mL of dichloromethane, TFA (770 mL) was added. The resulting mixture was stirred for 8 h. In about 6 h a precipite formed and was filtered and recrystallized from chloroform to give 1025.1 g of 25.

$^1$H NMR (DMSO): δ 9.34 (d, 1H, NH), 8.13 (b.s., 3H, NH$_2$ TFA salt), 5.17 (d, 1H, CH), 4.20 (m, 4H, CH$_2$), 3.71 (d, 2H, CH$_2$), 1.22 (t, 6H, CH$_3$).

Example 13

Preparation of poly(HPMA)-GFLG-Asp=Pt(NH$_2$R'), 22 kDa

A. Preparation of poly(HPMA)-GFLG-Asp-diEt (42)

An oven-dried 250 mL media bottle equipped with a stir bar and septum cap was charged in an inert atmosphere with poly(HPMA)-GFLG-ONp (12) (15.01 g, 6.604 mmol ONp groups) and Asp-diEt HCl (5.98 g, 26.5 mmol). Pyridine (208 mL) was added by cannulation and the resulting solution was stirred at ambient temperature for 17 h at which time HPLC showed the reaction was complete. The mixture was heated at 40-45° C. for 3 h and cooled to ambient temperature. The crude product was precipitated with 1.5 L of dry EtOAc. After stirring at ambient temperature overnight, crude 42 was collected on a coarse frit, washed three times with 60 mL of EtOAc and dried under a rubber dam to give 17.42 g of a pale yellow solid. The solid was dissolved in 175 mL of absolute EtOH and 54 g of AG 501-X8 (D) IX resin ($H^+$ and $OH^-$ forms) was added and the mixture gently stirred for 2; 5 h. The resin was removed by filtration, the volume of EtOH was reduced to a 17% (wt/vol) solution, and 42 was precipitated with 2 L of EtOAc and 0.2 L of diethyl ether. After stirring overnight, the precipitate was collected, washed, dried as above to give 1.3.94 g of 42 as an off-white powder.

$^1$H NMR ($D_2O$): δ 7.7-7.3 (4 br.s., NH and ArH), 4.68 (br.s., αH-phe), 4.3 (br.s., 1H, αH-leu), 4.15 (br.m., 4H, $OCH_2CH_3$), 3.92 (br.s., $NHCH_2CH(OH)CH_3$), 3.18 and 3.1 (br.d., 10H, $NHCH_2CH(OH)CH_3$), 3.0 (br.s., 2H, $CH_2$-Asp), 2.1-1.2 (m, $CH_2CCH_3$, $CH_2$-leu, CH-leu), 1.19 (br.s., $NHCH_2CH(OH)CH_3$), 0.98 (br.s., $CH_2CCH_3$), 0.8 (br.s., $CH_3$-leu).

B. Preparation of poly(HPMA)-GFLG-Asp=Pt($NH_3$)$_2$ (60a)

1. Hydrolysis of poly(HPMA)-GFLG-Asp-diEt

To a 50 mL centrifuge tube equipped with a stir bar was added 1.50 g of poly(HPMA)-GFLG-Asp-diEt (0.66 mmol Asp-diEt) and 20 mL of water. After stirring for 1 h, 1.06 mL (2.12 mmol) of 2 N NaOH was added to raise the pH to 12.5-12.7. After 53 min, 1.50 g of Bio-Rex MSZ 501 (D) resin was added and, after the pH was below 7, the solution was sterile filtered. The pH of the filtrate was raised to 7.4 with 2 N NaOH to give a solution of poly(HPMA)-GFLG-Asp-($CO_2Na$)$_2$.

2. Preparation of poly(HPMA)-GFLG-Asp=Pt($NH_3$)$_2$, O,O-chelate

To the solution of poly(HPMA)-GFLG-Asp-($CO_2Na$)$_2$ at pH 7.4 was added 5.93 mL (0.792 mmol) of 1a to give a reaction mixture with a pH of 5.10. While stirring overnight the pH dropped to about 3.5. The pH was adjusted to 5.4 with 2 N NaOH, Chelex 100 resin was added, the mixture stirred gently for 2 h and then the resin was removed by sterile filtration to give 35.5 mL of filtrate containing 60a.

3. Preparation of poly(HPMA)-GFLG-Asp=Pt($NH_3$)$_2$, N,O-chelate

The 35.5 mL of 60a was made 110 mM in NaCl and 80 mM phosphate (pH=7.4) by addition of 0.2075 g (3.55 mmol) NaCl, 0.0784 g (0.568 mmol) $NaH_2PO_4H_2O$, and 0.610 g (2.27 mmol) $Na_2HPO_4$ $7H_2O$. The pH was adjusted to 7.4 with 2 N NaOH. The solution was warmed to 38° C. in a water bath then placed in a 38° C. oven for 24 h. The dark brown solution was purified by repeated centrifugal ultrafiltration and then lyophilized to give 1.10 g of a brown solid: 6.74% Pt.

$^1$H NMR ($H_2O$): δ 7.4 and 7.3 (br s, 5, ArH), 4.65 (br s, 1, α-H-phe), 4.47 (br m, 1, Asp), 4.35 (br s, 1, α-H-leu0, 3.90 (br s, 1, $CH_2CHOHCH_3$), 3.85-3.60 (br m, 2, Asp), 3.50-2.90 (br d, 2, $CH_2CHOHCH_3$), 3.80-3.60 (br m, 2, $CH_2$-gly), 2.40-1.47 (br m, $CH_2$ of polymer backbone), 1.47-1.05 (br s, $CH_2CHOHCH_3$), 1.05-0.50 (br m, $CH_3$ of polymer backbone);

$^{195}$Pt NMR (($H_2O$: $D_2O$, 9/:7): δ −2023 (s), −2066 (br s), 2 N,O— chelates, ratio of 1:10.

SEC: $M_p$=24.7 kD, $M_w$=25.2 kD, $M_n$=12.0 kD, and $M_w/M_n$=2.10. Percent Pt in PBS at 37° C., 1.95% at 3 h, 5.85% at 24 h.

Example 14

Preparation of poly(HPMA)-GFLG-NH—($CH_2$)$_3$—S(O)$_2$Ama=Pt($NH_2R'$), $M_w$=24 kDa A. Preparation of poly(HPMA)-GFLG-$C_3$-Sulf-Ama-diEt (44)

An oven-dried 100 mL media bottle equipped with a stir bar and septum cap was charged with 2.24 g (6.74 mmol) $NH_2$—$C_3$-Sulf-Ama-diEt HCl (20) and 80 mL anhydrous pyridine and stirred. Then 8.03 g of poly(HPMA)-GFLG-ONp (12) was added, the mixture stirred until it dissolved and then held at 40-45° C. for 44.5 h. During this time aliquots were analyzed for free and total HONp. After 43 h the reaction was found to be complete. The crude product was precipitated with 0.6 L of dry EtOAc and 0.2 L of diethyl ether. After stirring at ambient temperature for 1.5 h, the precipitate was isolated by centrifugal sedimentation at 3840 RCF at 15° C. for 10 min. The supernatant was discarded, and the pellet was washed, centrifuged and decanted three times with 30 mL of diethyl ether. After drying, the solid was dissolved in 80 mL absolute EtOH and gently stirred with 25.0 g of AG 501-X8 (D) IX resin ($H^+$ & $^-$OH forms). After 2.5 h, the resin was removed by filtration, and the polymer was precipitated with 0.9 L of EtOAc and 0.2 L of diethyl ether. After stirring for 1 h, the polymer was isolated and washed by centrifugal sedimentation. The product was dried in vacuo to give 7.08 g of 44 as an off-white powder.

$^1$H NMR ($CD_3OD$): δ 7.48 (br.s., NH & ArH), 7.28 (br.s., αH-phe), 4.81 (br.s. 1H, α-H-asp), 4.44 (br.s 1H, αH-leu), 4.11 (br.m., 4H, $OCH_2CH_3$), 3.63 (br.s., $NHCH_2CH(OH)CH_3$ and $CH_2$-gly), 3.18 and 3.00 (br.m., $NHCH_2CH(OH)CH_3$), 2.88 (br s, 2H, $CH_2$-Asp), 2.1-1.2 (m, —$CH_2CCH_3$, $CH_2$-leu, CH-leu), 1.19 (brs, $NHCH_2CH(OH)CH_3$), 0.94 (brs, —$CH_2CCH_3$), 0.8 (brs, $CH_3$-leu).

B. Preparation of poly(HPMA)-GFLG-$C_3$-Sulf-Ama=Pt($NH_3$)$_2$(75a)

1. Hydrolysis of poly(HPMA)-GFLG-$C_3$-Sulf-Ama-diEt

The hydrolysis was performed as described in Example 15.B.1 using poly(HPMA)-GFLG-Ama-Sulf-C3-diEt (0.50 g, 0.2110 mmol Ame-diEt residues), 4.2 mL $H_2O$ (to form a 12% solution), 2 N NaOH (0.295 mL, 0.590 mmol), and Bio-Rex MSZ 501 (D) resin (0.50 g).

2. Preparation of poly(HPMA)-GFLG-$C_3$-Sulf-Ama=Pt($NH_3$)$_2$ O,O-chelate

The platination was performed as described in Example 15.B.2 with 1.60 mL (0.253 mmol) of 1a, and 0.1540 g of Chelex resin.

3. Preparation of poly(HPMA)-GFLG-$C_3$-Sulf-Ama=Pt($NH_3$)$_2$ N,O-Chelate:

This chelate conversion and purification was performed as in Example 15.B.3 using 0.0482 g (0.8248 mmol) NaCl, 0.0166 g (0.1203 mmol) $NaH_2PO_4H_2O$, and 0.1287 g (0.4801 mmol) $Na_2HPO_4.7H_2O$. After purification and lyophilization 0.219 g of 75a was obtained as a brown solid.

$^1$H NMR ($D_2O$): δ 7.38 (br d, 5, Ar), 4.68 (br s, 1, α-H-phe), 4.40 (br s, 1, α-H-leu), 3.95 (br s, H, —$CH_2CHOHCH_3$), 3.80-3.50 (m, propyl), 3.20 (br d, $CH_2CHOHCH_3$), 2.40-1.47 (br m, $CH_2$ of polymer backbone), 1.47-1.05 (br s, $CH_2CHOHCH_3$), 1.05-0.50 (br s, $CH_3$ of polymer backbone).

$^{195}$Pt NMR ($H_2O$/$D_2O$, 93/7): δ −2015 (br s), N,O-chelate 100%;

SEC: $M_p$=21.1 kD, $M_w$=24.0 kD, $M_n$=7.6 kD, and PDI=3.18.

Pt release in PBS at 37° C., 3.02% at 3 h, 5.44% at 24 h.

C. Preparation of poly(HPMA)-GFLG-$C_3$-Sulf-Ama=PtDACH (71b)

1. Hydrolysis of poly(HPMA)-GFLG-C$_3$-Sulf-Ama-diEt

This hydrolysis was performed under the same conditions as those used in Example 15. Quantities of reagents used were: poly(HPMA)-GFLG-Ama-Sulf-C3-diEt (5.50 g, 2.321 mmol Ame-diEt residues), 46 mL H$_2$O (to form a 12% solution), 2 N NaOH (3.241 mL, 6.48 mmol), Bio-Rex MSZ 501(D) resin (5.50 g).

2. Preparation of poly(HPMA)-GFLG-C$_3$-Sulf-Ama=PtDACH, O,O-chelate

This preparation was performed under the same conditions as those used in Example 15 using a cis-[PtDACH(H$_2$O)$_2$]$^{2+}$2 NO$_3^-$ 1b platinating solution. Quantities of reagents used were: 20.50 mL of a 26,487 ppm Pt solution of a cis-[PtDACH(H$_2$O)$_2$]$^{2+}$.2 NO$_3^-$ and Chelex resin (1.6943 g).

3. Preparation of poly(HPMA)-GFLG-C$_3$-Sulf-Ama=PtDACH, N,O-Chelate 71 b

This preparation was performed under the same conditions as those used in Example 1. The purification was performed using tangential flow filtration. Quantities of reagents used were: 0.6428 g (11 mmol) NaCl, 0.2208 g (1.60 mmol) NaH$_2$PO$_4$, and 1.7156 g (6.40 mmol) Na$_2$HPO$_4$. The product was obtained as 4.10 g of a brown solid. % Pt=6.58.

$^1$H NMR (D20): δ 7.38 (br d, 5, Ar), 4.68 (br s, 1, α-H-phe), 4.40 (br s, 1, α-H-leu), 3.95 (br s, H, —CH$_2$CHOHCH$_3$), 3.80-3.50 3.80-3.50 (m, propyl), 3.20 (br d, CH$_2$CHOHCH$_3$), 2.60-2.20 (br m, DACH-CH$_2$), 2.20-1.47 (br m, CH$_2$ of polymer backbone), 1.47-1.10 (br s, CH$_2$CHOHCH$_3$), 1.10-0.50 (br s, CH$_3$ of polymer backbone).

Pt release in PBS at 37 C, 2.12% at 3 hr, 4.54% at 24 hr.

Example 15

Preparation of poly(HPMA)-GFLG-NH—(CH$_2$)$_3$—S(O)$_2$-Asp=Pt(NH$_2$R'), 22 kDa (76)

Poly(HPMA)-GFLG-NH—(CH$_2$)$_3$—S(O)$_2$-Asp=Pt(NH$_2$R') (76) was prepared by hydrolysis of poly(HPMA)-GFLG-NH—(CH$_2$)$_3$—S(O)$_2$-Asp-diEt followed by treatment with 1a or 1b according to procedure described in Examples 13 and 14.

Example 16

Preparation of poly(HPMA)-GG-Ama=Pt(NH$_2$R'), 22 kDa

A. Coupling of poly(HPMA)-GG-ONp to Ame

An oven-dried 500 mL media bottle equipped with a stir bar and septum cap was charged with 6.0 g of poly(HPMA)-GG-ONp (12, 3.162 mmol of ONp) and 2.673 g (12.6 mmol) diethyl aminomalonate HCl (Ama-diEt HCl). Dry pyridine (87 mL) was cannulated into the flask and the mixture was stirred at 40° C. until a solution was obtained. The extent of the reaction was determined by measuring the free and total HONp. When the free HONp equaled the total HONp the poly(HPMA)-GG-Ama-diEt (29) was precipitated by addition of 800 mL of dry ethyl acetate and stirred for 1 h. The mixture was transferred to 200 mL centrifuge bottles and the solid isolated by centrifugal sedimentation at 3840 RCF for 10 min. The sediment was washed three times with 100 mL of diethyl ether. The sediment was dissolved in 70 mL of EtOH and gently stirred with 18 g of AG 501-X8(D) IX resin (H$^+$ & OH$^-$ forms) for 1 hr. The resin was filtered and the polymer precipitated and purified by centrifugal sedimentation. After drying in vacuo, 6.25 g of a white powder was obtained.

$^1$H NMR (DMSO-d$_6$): δ 7.3 (m, amide NH), 5.1 (d, NHC), 4.6 (s, CH$_2$CHOHCH$_3$), 4.2 (q, NHC), 3.6 (s, CH$_2$CHOHCH$_3$), 3.1 (s, CH$_2$CHOHCH$_3$), 1.7 (br.m., CH$_2$ of polymer backbone), 1.2 (q, NHC), 1.1 (s, CH$_3$ of polymer backbone), 0.9 (s, CH$_2$CHOHCH$_3$), and no small molecules except for <1% of EtOH and EtOAc.

B. Platination of poly(HPMA)GG-Ama-diEt with cis DDP (~25 kDa) (53a)

A 50 mL centrifuge tube equipped with a stir bar was charged with 0.5 g (0.2635 mmol Ame residues) of p(HPMA)-GGAme, and 4.2 mL of Milli-Q H$_2$O. After dissolution, 0.347 mL (0.694 mmol NaOH) of 2 M NaOH was added and the pH maintained at 12.6 for 90 minutes. The solution was then stirred with 0.71 g of Bio-Rex MSZ 501 D resin. The pH fell to 7.84 after which the resin was removed by filtration. The pH of the filtrate was then adjusted to 7.31 with 2 M NaOH.

C. Preparation of poly(HPMA)-GG-Ama=Pt(NH$_3$)$_2$, O,O-Chelate

To the above pH 7.3 solution, 2.40 mL (0.316 mmol Pt) of a 30,149 ppm solution of cis-[Pt(NH$_3$)$_2$(H$_2$O)$_2$]$^{2+}$.2NO$_3^-$(1a) was added. The pH was quickly adjusted to 5.6 with 2 M NaOH. While stirring overnight the pH dropped to 3.31. It was again raised to 5.4, then 0.192 g of Chelex resin was added. After gently stirring for 90 min, the resin was removed by sterile filtration to give 9 mL of a slightly colored solution of 45.

D. Preparation of poly(HPMA)-GG-Ama=Pt(NH$_3$)$_2$ N,O Chelate

The above 9 mL of filtrate was made 110 mM in NaCl and 80 mM phosphate (pH=7.4) by adding 0.069 g (0,89 mmol) NaCl, 0.019 g (0.142 mmol) NaH$_2$PO$_4$.H$_2$O, and 0.153 g (0.57 mmol) Na$_2$HPO$_4$.7H$_2$O. The pH was adjusted to 7.4 and the solution warmed to 38° C. in a water bath and then transferred to a 38° C. oven for 24 h. The solution was purified by centrifugal ultrafiltration and lyophilized to yield 0.413 g of an off-white solid 53a: 10.5% Pt, 7.31% H$_2$O; % Pt Release at 3 & 24 h, 1.4%, 4.6%.

$^{195}$Pt NMR (93:7H$_2$O: D$_2$O): δ −2060 (br s, N,O Chelate of Pt).

SEC: M$_p$=24.6 kDa, M$_w$=25.4 kDa, M$_n$=17.6 kDa, M$_w$/M$_n$=1.44.

E. Preparation of poly(HPMA)-GG-Ama=Pt=1R,2R-DACH. (~24 kDa) (53b)

A 250 mL media bottle equipped with a stir bar was charged with 5.0 g (2.635 mmol Ama-diEt) of p(HPMA)-GG-Ama-diEt and 42 mL of Milli-Q H$_2$O. After dissolution, 3.47 mL (6.94 mmol NaOH) of 2 M NaOH was added and the pH maintained at 12.6 for 90 minutes. Next, 5 g of Bio-Rex MSZ 501 D resin was added and the mixture gently stirred until the pH fell to 7.41 at which time the resin was removed by filtration. The pH of the filtrate was then adjusted to 7.49 with 2 M NaOH.

F. Preparation of poly(HPMA)-GG-Ama=Pt=1R,2R-DACH, O,O-Chelate (45)

To the above filtrate at pH 7.5, 25.9 mL (3.16 mmol Pt) of a 23,808 ppm solution of 1b was added. The pH was adjusted to 5.23. After stirring overnight, the pH fell to 4.11. The pH was re-adjusted to 5.4 with 2 M NaOH, and 1.92 g of Chelex resin was added, the mixture gently stirred and then sterile filtered to give 100 mL of filtrate.

G. Preparation of poly(HPMA)-GG-Ama=Pt t=1R,2R-DACH, N,O-Chelate (53b)

The above filtrate was made 110 mM in NaCl and 80 mM phosphate by addition of 0.648 g (11 mmol) NaCl, 0.221 g (1.6 mmol) NaH$_2$PO$_4$.H$_2$O, and 1.71 g (6.4 mmol) Na$_2$HPO$_4$.7H$_2$O. The pH was adjusted to 7.4 and the mixture warmed to 38° C. in a H$_2$O bath and then transferred to a 38° C. oven for 24 h. The solution was subjected to TFF purification and lyophilized to yield 4.31 g of an off-white solid: 9.7% Pt, 7.62% $H_2O$; % Pt Release at 3 & 24 h, 1.3%, 5.5%.

$^1$H NMR ($D_2O$): δ 6.3 (s, amide protons) 4.8 (s, HOD), 4.2 (s), 4.0 (s), 3.2 (d, $CH_2$ of HPMA side chain), 1.8 (d, $CH_2$ of polymer backbone), 1.2 (s, $CH_3$ of HPMA side chain), 0.9 (s, $CH_3$ of polymer backbone).

SEC $M_p$=24.1 kDa, $M_w$=24.4 kDa, $M_n$=15.7 kDa, $M_w/M_n$=1.56.

Example 17

Preparation of poly(HPMA)-GG-Asp=Pt(NH$_2$R'), 22 kDa (54)

A. Coupling of poly(HPMA)-GG-ONp to AspdiEt

An oven-dried 500 mL media bottle equipped with a stir bar and septum cap was charged with 6.0 g (3.162 mmol of ONp) of p(HPMA)-GG-ONp (12), 2.85 g (12.6 mmol) diethyl aspartate HCl (Asp-diEt) after which 89 mL dry pyridine was added. The bottle was capped and the solids were stirred until dissolved. The solution was transferred to a 40° C. $H_2O$ bath. The extent of the reaction was determined by measuring the free and total HONp. After 48 h the reaction was found to be complete. The product was precipitated with 800 mL of dry ethyl acetate, stirred for 1 h and then isolated by centrifuge sedimentation. The sediment was washed three times with 100 mL of diethyl ether. The sediment was dissolved in 75 mL of absolute EtOH, stirred with 18.9 g of AG 501-X8(D) IX resin (H$^+$ & OH$^-$ forms) for 1 h and filtered. The polymer was precipitated and purified by centrifuge sedimentation and dried in vacuo to yield 6.01 g of 30.

$^1$H NMR (DMSO-d$_6$): δ 7.3 (m, amide NH), 4.7 (s, $CH_2CHOHCH_3$), 4.5 (t-d, NHC) 4.2 (q, NHC), 3.6 (s, $CH_2CHOHCH_3$), 3.0 (s, $CH_2CHOHCH_3$), 1.7 (br.m., $CH_2$ of polymer backbone), 1.2 (q, NHC), 1.1 (s, $CH_3$ of polymer backbone), 0.9 (s, $CH_2CHOHCH_3$), and no small molecules except for <1% each of EtOH and EtOAc.

B. Preparation of Low Molecular Weight poly(HPMA)-GG-Asp=Pt(NH$_3$)$_2$

Hydrolysis of poly(HPMA)-GG-Asp-diEt was performed under the same conditions as those in Example 13 using poly(HPMA)-GG-Asp-diEt (0.50 g, 0.2635 mmol Asp-diEt residues), 4.2 mL $H_2O$ (to form a 12% solution), 2 N NaOH (0.35 mL, 0.70 mmol) and Bio-Rex MSZ 501(D) resin (0.50 g).

C. Preparation of poly(HPMA)-GG-Asp=Pt(NH$_3$)$_2$, O,O-chelate (46)

This preparation was performed under the same conditions as those in Example 13 using 2.05 mL of a 30,149 ppm Pt solution of cis-[Pt(NH$_3$)$_2$(H$_2$O)$_2$]$^{2+}$.2 NO$_3^-$ (1a) and Chelex resin (0.1923 g).

D. Preparation of poly(HPMA)-GG-Asp=Pt(NH$_3$)$_2$, N,O-chelate (54a)

This preparation and purification was performed under the same conditions as those in Example 13 using 0.1318 g (2.25 mmol) NaCl, 0.0453 g (0.3283 mmol) NaH$_2$PO$_4$, and 0.3517 g (1.312 mmol) Na$_2$HPO$_4$. The product was obtained as a brown solid (0.138 g). Pt release in PBS at 38.C: 3.92% at 3 hr, 11.02% at 24 hr.

E. Preparation of Low Molecular Weight poly(HPMA)-GG-Asp=PtDACH (54b)

Hydrolysis of poly(HPMA)-GG-Asp-diEt was performed under the same conditions as those in Example 13 using poly(HPMA)-GG-Asp-diEt (5.00 g, 2.635 mmol Asp-diEt residues), 42 mL $H_2O$ (to form a 12% solution), 2 N NaOH (3.48 mL, 6.96 mmol) and Bio-Rex MSZ 501(D) resin (5.00 g).

F. Preparation of poly(HPMA)-GG-Asp=PtDACH, O,O-chelate (46)

This preparation was performed under the same conditions as those in Example 13 using 24410 ppm Pt cis-[PtDACH (H$_2$O)$_2$]$^{2+}$.2 NO$_3$— platinating solution and Chelex resin (1.9235 g).

G. Preparation of poly(HPMA)-GG-Asp=PtDACH, N,O-Chelate (54b)

This preparation was performed under the same conditions as those in Example 16 using 0.6428 g (11 mmol) NaCl, 0.2208 g (1.60 mmol) NaH$_2$PO$_4$, and 1.7156 g (6.40 mmol) of Na$_2$HPO$_4$. The purification was performed using tangential flow filtration. % Pt=8.76.

$^1$H NMR (D20): δ 3.90 (br s, 1, —CH$_2$CHOHCH$_3$), 3.40-2.90 (br d, 2, —CH$_2$CHOHCH$_3$), 2.80-2.37 (m, CH$_2$-gly), 2.35-1.49 (broad envelope, CH$_2$ of polymer backbone), 1.49-1.10 (br s, (—CH$_2$CHOHCH$_3$), 1.10-0.30 (br s, —CH$_3$ of polymer backbone).

$^{195}$Pt NMR (H$_2$O: D$_2$O, 93:7, 64.4 MHz): δ –2261 (br s), –2287 (br s), –2577 (br s), 2 N,O-chelates and 1 tetra-N chelate, in a ratio of N,O: N,N of 8:1.

SEC $M_p$=21.3 kD, $M_w$=21.6 kD, $M_n$=13.2 kD, and PDI=1.64; Pt release in PBS at 37° C., 3.20% at 3 h, 10.68% at 24 h.

Example 18

Preparation of poly(HPMA)-GG-NH—(CH$_2$)$_3$—S(O)$_2$-Ama=Pt(NH$_2$R'), 22 kDa (69)

A. Preparation of poly(HPMA)-GG-C$_3$-Sulf-Ama=Pt(NH$_3$)$_2$ (69a)

Hydrolysis of poly(HPMA)-GG-C$_3$-Sulf-Ama-diE was performed under the same conditions as in Example 13 using poly(HPMA)-GG-Ama-Sulf-C3-diEt (0.50 g, 0.2635 mmol Asp-diEt residues), 4.2 mL H$_2$O (to form a 12% solution), 2 N NaOH (0.35 m, 0.70 mmol) and Bio-Rex MSZ 501(D) resin (0.50 g).

B. Preparation of poly(HPMA)-GG-C$_3$-Sulf-Ama=Pt(NH$_3$)$_2$ O,O-Chelate

This preparation was performed under the same conditions as those in Example 13 using 2.05 mL of a 30,060 ppm Pt solution of cis-[Pt(NH$_3$)$_2$(H$_2$O)$_2$]$^{2+}$.2 NO$_3^-$ (1a) and Chelex resin (0.1923 g).

C. Preparation of poly(HPMA)-GG-C$_3$-Sulf-Ama=Pt(NH$_3$)$_2$ N,O-Chelate

This preparation and purification was performed under the same conditions as those in Example 13 using 0.077 g (1.3175 mmol) NaCl, 0.0265 g (0.1920 mmol) NaH$_2$PO$_4$ and 0.2059 g (0.7681 mmol) Na$_2$HPO$_4$. Product 69a was obtained as 0.134 g of brown solid.

$^{195}$Pt NMR (H$_2$O: D$_2$O, 93:7, 64.4 MHz); 6-2018 (br s), N,O-chelate 100%.

SEC $M_p$=20.3 kD, $M_w$=21.6 kD, $M_n$=14.5 kD, and PDI=1.49.

Example 19

Preparation of poly(HPMA)-GG-NH—(CH$_2$)$_3$—S(O)$_2$-Asp=Pt(NH$_2$R'), 22 kDa (70)

A. Preparation of poly(HPMA)-GG-C$_3$-Sulf-Asp=Pt(NH$_3$)$_2$ (70a)

Hydrolysis of poly(HPMA)-GG-C$_3$-Sulf-Asp-diEt was performed under the same conditions as in Example 13 using poly(HPMA)-GG-Asp-Sulf-C3-diEt (0.50 g, 0.2635 mmol Asp-diEt residues), 4.2 mL H$_2$O (to form a 12% solution), 2 N NaOH (0.35 mL, 0.70 mmol) and Bio-Rex MSZ 501 (D) resin (0.50 g).

B. Preparation of poly(HPMA)-GG-C$_3$-Sulf-Asp=Pt (NH$_3$)$_2$ O,O-Chelate

This preparation was performed under the same conditions as those in Example 13 using 2.05 mL of a 30,060 ppm Pt solution of cis-[Pt(NH$_3$)$_2$(H$_2$O)$_2$]$^{2+}$.2 NO$_3^-$ ′(1a) and Chelex resin (0.1923 g).

C. Preparation of poly(HPMA)-GG-C$_3$-Sulf-Asp=Pt (NH$_3$)$_2$ N,O-Chelate (70a)

This preparation and purification was performed under the same conditions as those in Example 13 using 0.077 g (1.3175 mmol) NaCl, 0.0265 g (0.1920 mmol) NaH$_2$PO$_4$, and 0.2059 g (0.7681 mmol) Na$_2$HPO$_4$. The product was obtained as 0.231 g of brown solid.

$^{195}$Pt NMR (H$_2$O: D$_2$O, 93:7, 64.4 MHz): 6-2016 (br s), −2044 (br s), 2 N,O-chelates in a ratio of 1:4.

SEC M$_p$=20.5 kD, M$_w$=22.4 kD, M$_n$=14.3 kD, and PDI=1.57.

Example 20

Preparation of poly(HPMA)-GGGG-Ama=Pt (NH$_2$R'), 22 kDa (58)

A. Preparation of poly(HPMA)-GGGG-Ama-diEt, 22 kDa (33)

An oven-dried 250-mL r.b. equipped with stir bar and septum was charged with 5.724 g (14.19 mmol) of TFA GG-Ama-diEt (21), purged with N$_2$ and then 70 mL of dry pyridine was added by cannulation. After dissolution, 7.015 g of poly(HPMA)-GG-ONp was added in three portions, each portion being added after the previous one dissolved. The mixture was warmed to 40° C. and the extent of reaction monitored by HPLC. After 23 h the reaction was found to be complete and 0.7 L of dry EtOAc and 0.1 L of dry diethyl ether were added at ambient temperature and the mixture stirred for 1 h to precipitate the polymer. The mixture was centrifuged at 3840 RCF for 10 min at 4° C. and decanted. The solid was dissolved in 60 mL absolute EtOH and stirred with 22.0 g of AG 501-X8 (D) IX resin (H$^+$ & OH$^-$ forms) for 2.5 h. The resin was removed by filtration and the polymer precipitated with addition of 800 mL of EtOAc. After stirring for 1 h, the precipitate was isolated by centrifugation, washed successively with EtOAc and ether and dried in vacuo to give 5.77 g of 33 as an off-white powder.

B. Platination of poly(HPMA)-GGGG-Ama-diEt (31) with 1b (22 kDa)

1. Hydrolysis of poly(HPMA)-GGGG-Ama-diEt

A 250 mL bottle containing a stir bar, 5.5 g (2.895 mmol Ame residues) of poly(HPMA)-GGGG-Ama-diEt (33), and 46 mL of Milli-Q H$_2$O was stirred until a solution was obtained. The pH was raised to 12.6 with 3.81 mL (7.62 mmol) of 2 M NaOH and held there for 90 min. The mixture was neutralized with 5.5 g of Bio-Rex MSZ 501D resin to lower the pH to 7.51 after which the resin was removed by filtration. The initial pH of the filtrate was 2.1 which was raised to 6.93 with 2 M NaOH to give a solution of poly (HPMA)-GGGG-Ama(CO$_2$Na)$_2$ 2. Preparation of poly(HPMA)-GGGG-Ama=PtDACH O,O-Chelate (49)

To the above solution of poly(HPMA)-GGGG-Ama (CO$_2$Na)$_2$ was added 27.5 mL (3.47 mmol Pt) of a solution of 1b. The pH, which fell to 4.41, was adjusted to 5.14 with 2 M NaOH. While stirring overnight, the pH fell to 2.44. The pH was re-adjusted to 5.4 with 2 M NaOH and 2.114 g of Chelex-100 resin was added and the mixture gently stirred. After 90 min, the resin was removed by sterile filtration to give 100 mL of filtrate.

3. Preparation of poly(HPMA)-GGGG-Ama=PtDACH, N,O Chelate (57b)

The above 100 mL of filtrate above was made 110 mM in NaCl and 80 mM phosphate (pH=7.4) with 0.648 g (11 mmol) NaCl, 0.221 g (1.6 mmol) NaH$_2$PO$_4$.H$_2$O, 1.71 g (6.4 mmol) Na$_2$HPO$_4$.7H$_2$O, and 2 M NaOH. The solution was warmed to 38° C. in a H$_2$O bath and transferred to a 38° C. oven for 24 h. The solution was purified by TFF and lyophilized to yield 4.31 g of an off-white solid: 8.86% Pt, 9.35% H$_2$O; % Pt Release at 3 & 24 h, 0.972%, 3.173%.

$^{195}$Pt NMR (93:7H$_2$O: D$_2$O): δ −2229.2, −2262.1, and −2292.1 (s).

Example 21

Preparation of poly(HPMA)-GGGG-Asp=Pt (NH$_2$R'), 22 kDa

A. Preparation of poly(HPMA)-GGGG-Asp-diEt, about 22 kDa (34)

An oven-dried 500-mL media bottle equipped with a stir bar and septum cap was charged with 4.399 g (10.54 mmol) TFA GG-Asp-diEt (22) and 100 mL of dry pyridine was added by cannulation. Upon dissolution, 10.02 g of poly (HPMA)-GG-ONp (12) was added in three portions, each portion being added after the previous one dissolved. The mixture was warmed to 40° C. and the extent of reaction was monitored by an HPLC assay for free and total HONp. The reaction was complete after 21 h and was cooled to ambient temperature. The pyridine was removed in vacuo, the residue was dissolved in absolute EtOH to give an approximately 30% w/v solution. The product was precipitated with 0.7 L of dry EtOAc and 0.1 L of diethyl ether. After stirring for 1 h, the mixture was centrifuged at 3840 RCF for 5 min at 5° C. The supernatant was discarded, the solid was dissolved in about 70 mL of absolute EtOH and stirred with 41.0 g of AG 501-X8 (D) IX resin (H$^+$ & OH$^-$ forms) for 2.5 h. The resin was removed by filtration and 0.9 L of EtOAc was added. After stirring for 1 h, the product was isolated by centrifugation, washed with EtOAc and diethyl ether and dried in vacuo to give 34 as an off-white powder.

Example 22

Preparation of poly(HPMA)-GGGG-NH—(CH$_2$)$_3$—S(O)$_2$-Ama=Pt(NH$_2$R'), 22 kDa (73)

Poly(HPMA)-GGGG-NH—(CH$_2$)$_3$—S(O)$_2$-Ama=Pt (NH$_2$R') was prepared by hydrolysis of 65 followed by treatment with 1a or 1b as described in Examples 13 and 14.

Example 23

Preparation of poly(HPMA)-GGGG-NH—(CH$_2$)$_3$—S(O)$_2$-Asp=Pt(NH$_2$R'), 22 kDa (74)

Poly(HPMA)-GGGG-NH—(CH$_2$)$_3$—S(O)$_2$-Asp=Pt (NH$_2$R') was prepared by hydrolysis of 66 followed by treatment with 1a or 1b as described in Examples 13 and 14.

Example 24

Preparation of N-acetyl-Asp=Pt(NH$_3$)$_2$

A. Platination of N-acetylaspartate with 1a at pH=2

To a solution of 250 mg (1.42 mmol) of N-acetylaspartic acid in 5 mL water in a 20 mL vial equipped with a stir bar, 11.4 mL (1.35 mmol Pt) of 1a was added. The pH fell to 1.8 and was adjusted to 2.1 with 2 M NaOH. The bright yellow solution was stirred for 3 h and then 64.3 mg (1.1 mmol) NaCl was added and the mixture stirred until the salt dissolved. The solution was incubated for 24 h at 370 C during which time it turned dark orange and orange crystals formed.

$^{195}$Pt NMR: δ −1398.5, −1584.5 (s cis Pt(II) (H$_2$O)$_2$ (NH$_3$)$_2$), −2042.1 (s Pt N,O-chelate).

B. Platination of N-acetylaspartate with 1a at pH=5.4.

The above procedure was repeated at pH=5.4. The resulting solution after incubation was brick red and contained dark red crystals. The crystals were insoluble in all NMR solvents tried.

$^{13}$C NMR of the red solution (95 H$_2$O: 5 D2O): δ 175.6, 175.1, 174.7, 173.2, 169.1, 47.9, 46.8, 45.7, 37, 7, 34.0, 17.5.

$^{195}$Pt NMR: δ −1584.5 (s cis Pt(II) (H$_2$O)$_2$(NH$_3$)$_2$), −1808.7, −2037.5, −2060, −2104.

Example 25

Preparation of poly(HPMA)-GGG-Ama=Pt=1R, 2R-DACH (Compound C13)

A. DACH=Pt(OH$_2$)$_2^{2+}$ (1R, 2R)DACH=PtCl$_2$ (1.91 g, 5.02 mmol) and AgNO$_3$ (1.67 g, 9.83 mmol) were added to an aluminum foil covered 100 mL media bottle containing a stir bar. Milli-Q water (35.9 mL) and 5% HNO$_3$ (150 µL) were added. The vessel was placed in a 60° C. water bath and the mixture stirred vigorously for 15 h. It was then transferred to an ice bath for 15 mins and the precipitate was removed by filtration. The filter cake was washed with Milli-Q water. The filtrate volume was 43.2 mL. A sample of this solution was analyzed for platinum content by ICP: theoretical ppm Pt-22,742 ppm; found −22, 503 ppm (98.9% yield).

B. Hydrolysis of poly(HPMA)-GGG-Ama-diEt

To a 100 mL media bottle equipped with a stir bar was added 4.9184 g of poly(HPMA)-GGG-Ama-diEt (2.33 mmol Ama-diEt residues). Milli-Q water (36.6 mL) was added with stirring to dissolve the polymer. 2N NaOH (3.17 mL, 6.34 mmol) was added to raise the pH to 12.45-12.65. The pH was maintained at this range for 30 mins, then 5.00 g of Bio-Rex MSZ 501 (D) resin was added. When the pH<7, the resin was removed by sterile filtration. The pH of the filtrate was raised to 7.4 with 2 N NaOH to give a solution of poly(HPMA)-GGG-Ama-(CO$_2$Na)$_2$.

C. Poly(HPMA)-GGG-Ama=Pt=1R, 2R-DACH, O,O-chelate

To the pH 7.4 solution of poly(HPMA)-GGG-Ama-(CO$_2$Na)$_2$ was added 38.2 mL of a 22,503 ppm Pt solution of cis-[PtDACH(H$_2$O)$_2$]$^{2+}$.2 NO$_3$— to give a reaction mixture having a pH of 4.80. This was adjusted to pH 5.4 using 2 N NaOH, and stirred for 2 h with the pH maintained between 5.2-5.5. Chelex 100 resin (2.70 g) was added and the mixture stirred for 90 min, then the resin was removed by sterile filtration.

D. Poly(HPMA)-GGG-Ama=Pt=1R, 2R-DACH, N,O-chelate

After removal of the Chelex 100 resin, the filtrate was diluted to a volume of 133 mL (3.75 wt. %). The solution was made 110 mM in NaCl and 80 mM phosphate (pH=7.4) by adding 0.8587 g (14.7 mmol) of NaCl, 0.2939 g (2.13 mmol) of NaH$_2$PO$_4$, and 2.2920 g (8.55 mmol) of Na$_2$HPO$_4$. The solution was warmed to 38° C. in a water bath then placed in a 38° C. incubator for 17 hrs, sterile filtered and purified by tangential flow filtration. The solution was then lyophilized to yield 3.98 g of a flaky brown solid containing 9.54% Pt.

$^1$H NMR (300 MHz, D$_2$O): δ 0.99 (RCH$_2$C(CH$_3$)R, (broad singlet, 3H); 1.19-1.20 (RCH(OH)CH$_3$, d, 3H, 5 Hz); resonances from 1.28 to 1.50 ppm (not conclusively identified); 1.51-2.67 (RCH$_2$C(CH$_3$)R and the DACH methine and methylene protons (broad unresolved envelope)); 2.75-3.50 (RNHCH$_2$CH(OH)CH$_3$ (two broad peaks)); 3.64-4.30 (RNHCH$_2$CH(OH)CH$_3$ and RNHCH$_2$C(O)R (unresolved envelope); 4.78 (HOD); 5.15 (NHCH(C(O))$_2$ (small singlet, mostly exchanged out)); 5.35 and 6.10 (DACH NH$_2$ (mostly exchanged out)); 7.50 (glycyl NH (mostly exchanged out)).

$^{195}$Pt NMR (H$_2$O: D$_2$O, 93:7, 64.4 MHz): δ 2 major N,O-chelate peaks at δ−2290 and −2262 (96% of total integrated peaks), and N,N-chelate peaks at δ−2578 and −2620 (4% of total integrated peaks).

SEC M$_w$=23.1 kDa, M$_n$=16.2 kDa, PDI=1.43

Example 26

Preparation of GAG-Gly-Ama=Pt(OH)$_2$(NH$_3$)$_2$

The following scheme will provide the title compound:

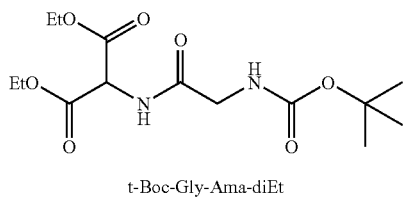

t-Boc-Gly-Ama-diEt

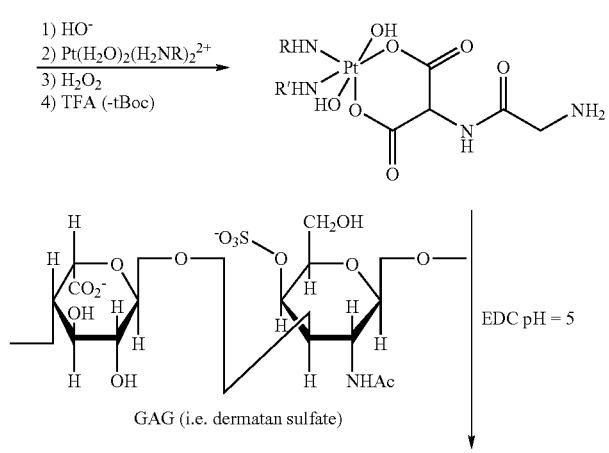

GAG (i.e. dermatan sulfate)

-continued

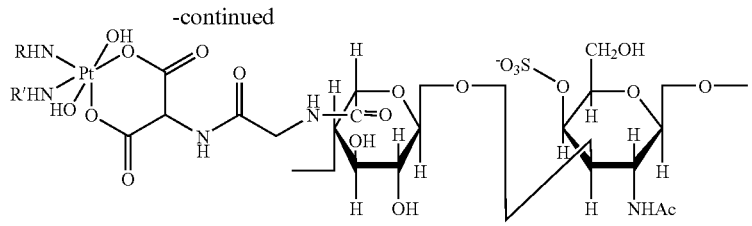

While only one carboxylate of the GAG is shown, nearly any proportion of the carboxyls could be substituted using the above procedure. The choice of how many would be substituted would depend on how the substitution affects the targeting ability of the GAG. The procedure is readily modifiable by techniques disclosed herein and those known to skilled artisans to include linkers in addition to, or other than, glycine and other axial Pt(IV) ligands such as Cl or O-acyl. This procedure is expected to be extendible to other GAGs, polyaspartate, polyglutamate and, in fact, with any polymer containing free —C(O)OH groups. The sulfates may also be substituted by techniques well known in the art.

Example 27

Actual and Theoretical Percent Platinum in Compound C13 After Correction for Water and ONp Content of Polymer Precursor.

The percent theoretical Pt was calculated from the ONp content of the polymer used to make the platinate polymer. It was assumed that each ONp is converted to an Ama group. Based on the ONp content, the smallest equivalent weight of the corresponding platinum-containing polymer was calculated. The percent theoretical Pt was calculated as the ratio of the actual percent Pt and the percent Pt from the smallest equivalent weight of the platinum polymer conjugate. The results are shown in Table 3.

TABLE 3

| Lot no. | % Pt | % Water | % Pt (dry wt) | mmol ONp per g of ONp-polymer | Theor % Pt (dry wt.) | % of Theor. Pt |
|---|---|---|---|---|---|---|
| 1 | 8.44 | 11.57 | 9.54 | 0.403 | 6.85 | 139% |
| 2 | 8.50 | 8.59 | 9.30 | 0.403 | 6.85 | 136% |
| 3 | 8.70 | 11.16 | 9.79 | 0.408 | 6.93 | 141% |
| 4 | 8.72 | 11.02 | 9.80 | 0.408 | 6.93 | 141% |
| 5 | 8.54 | 9.14 | 9.40 | 0.408 | 6.93 | 136% |
| 6 | 8.10 | 10.23 | 9.02 | 0.4308 | 7.26 | 124% |
| 7 | 10.00 | 12.2 | 11.39 | 0.5115 | 8.36 | 136% |
| 8 | 8.51 | 12.08 | 9.68 | 0.4216 | 7.11 | 136% |
| 9 | 9.83 | 12.04 | 11.18 | 0.5115 | 8.36 | 134% |
| 10 | 9.00 | 7.83 | 9.76 | 0.4744 | 7.85 | 124% |
| 11 | 10.68 | 9.13 | 11.75 | 0.4986 | 8.25 | 143% |
| 12 | 10.63 | 8.87 | 11.66 | 0.4667 | 7.80 | 150% |
| 13 | 11.11 | 8.85 | 12.19 | 0.5252 | 8.59 | 142% |
| Averages | 8.98 | 10.33 | 10.02 | 0.45 | 7.54 | 137% |

All percentages are wt/wt.
The % Pt (dry wt) is: % Pt/(1 − % water/100).

The theoretical % Pt is based on smallest equivalent weight of the ONp polymer and the smallest equivalent weight of the corresponding Compound 13.

The data demonstrates that there are other chelating sites along the linker between the polymer backbone and the Pt-complexing end group. Referring to Example 1, for example, there is 20-40% more Pt than can be accounted for by the number of Ama groups of the Ame-polymer precursor.

Example 28

Size Exclusion Chromatography

The average molecular weight distribution of the polymeric compounds of this invention were determined by size exclusion chromatography. In brief, compounds were analyzed on an SEC system consisting of an HPLC instrument equipped with two PL Aquagel-OH Mixed 8 gm columns (Polymer Labs) and an RI detector. Column ovens were held at 35° C. The mobile phase, consisting of a 35/65 mixture of methanol/water containing 10 mMLiClO$_4$, was pumped at a flow rate of 1.0 mL/min. Each analysis required 30 minutes. The column was calibrated with PEO/PEG standards and the results were fitted to a $4^{th}$ order polynomial of log($M_p$) as a function of reciprocal retention time. The reported values for $M_w$ and $M_n$ represent the average of three determinations of 100 µL taken from a 2 mg/mL sample dissolved in the mobile phase.

Example 29

Preparation of poly(HPMA)-GGGG-Ama=Pt-1R,2R-DACH

A. Hydrolysis of p(HPMA)-GGGG-Ame
Poly(HPMA)-GGGG-Ame (2.50, 1.21 mmol Ame groups) was transferred into a 100 mL media bottle containing a stir bar and dionized, pure water (18.5 mL) was added. Upon dissolution of the polymer 2N NaOH (1.60 mL, 0.32 mmol) was added, and the stirring solution rose to pH 12.67. The solution was maintained at pH 12.4-12.6 for 25 min, reduced to pH 7.4 by slow addition of 5% HNO3 (1.4 mL) to give a solution of poly(HPMA)-GGGG-Ama-(CO$_2$Na)$_2$ at approximately pH 6-7.

B. Preparation of poly(HPMA)-GGGG-Ama=Pt-1R,2R-DACH, N,O-chelates
To the stirring solution of poly(HPMA)-GGGG-Ama-(CO$_2$Na)$_2$ at pH 7.4 was added 17.3 mL (2.43 mmol) of a 24,721 ppm solution of DACH=Pt(NO$_3$)$_2$ to give a reaction mixture with a pH of 4.59. This was raised to pH 5.4 with 2N NaOH, the solution was stirred at pH 5.2-5.4 for 2 h, and filtered. The pH was the raised to 7.4 and placed in a 38° C. water bath where the pH was maintained at 7.4 for 18 h using a Mettler DL25 autotitrator loaded with 2N NaOH. The solution was filtered, and the filtrate was purified by tangential flow filtration and then lyophilized to give 2.54 g of a brown solid. $^{195}$Pt NMR (H$_2$O:D$_2$O, 93:7): δ −2263 and −2289 (br m, N,O-chelate, 96% of total), −2607 (br m, N,N-chelate), −2952 (s, <1%). 11.97% Pt, 12.32% H$_2$O 13.65% Pt (anhydrous, after correction for water); 1.62 equiv Pt/equiv Ame.

Example 30

Preparation poly(HPMA)-GGGG-Ama=Pt-1R,2R-DACH

A sample of poly(HPMA)-GGGG-Ama=Pt-1R,2R-DACH was prepared in a nearly identical manner to the previous example but 25.9 mL (3.64 mmol, 3.0 equiv/Ame) of a 27,421 ppm Pt solution of DACH=Pt(NO$_3$)$_2$ was used to give 2.83 g (93%) of a brown solid: $^{195}$Pt NMR (H$_2$O:D20, 93:7) δ −2262 (br m) and −2287 (br s); 14.25% Pt; 9.10% H$_2$O; 15.68% Pt (anhydrous, after correction for water); 1.86 equiv Pt/equiv Ame.

CONCLUSION

Thus, the present invention provides a number of new platinum complex compounds expected to be useful in the treatment of solid tumor cancers.

Although certain embodiments and examples have been used to describe the present invention, it will be apparent to those skilled in the art that changes in the embodiments and examples shown may be made without departing from the scope and spirit of this invention.

---

---

What is claimed:

1. A compound having the chemical structure:

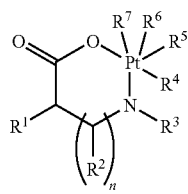
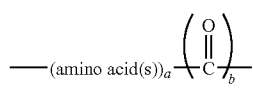

wherein:
- a is 2-50;
- b is 0 or 1;
- R$^{10}$ is selected from the group consisting of:
  - hydrogen; and,
  - a natural, semi-synthetic or synthetic backbone polymer;

wherein:
- n is 0 or 1;
- Pt is in a +2 or a +4 oxidation state;

wherein;
- R$^1$ and R$^2$ are independently selected from the group consisting of:
  - =O;
  - H;
  - —C(O)OH;
  - -(1C-6C)alkyl-C(O)OH;
  - —C(O)O$^-$R$^+$;

wherein:
  - R$^+$ is selected from the group consisting of Na$^+$ and K$^+$;

provided that:
  - when R$^2$ is =O, R$^1$ is not =O;
- R$^3$ is selected from the group consisting of:
  - —R$^9$;
  - -(1C-6C)alkyl-R$^9$;
  - —S(O)$_2$R$^{11}$;
- R$^9$ is -(linker)-R$^{10}$, wherein:
  - -(linker) is $R^{11}$ is selected from the group consisting of:
—$R^9$;
-(1C-6C)alkyl-$R^9$;
$R^4$ and $R^5$ are independently selected from the group consisting of:
ammonia;
a primary, secondary or tertiary (1C-6C)alkyl amine;
a (3C-8C)cycloalkyl amine;
an aryl amine;
a nitrogen heteroaryl;
a nitrogen heteroalicyclic;
an aminomethyl nitrogen heteroalicyclic; or,
together, as $R^4$—$R^5$:
  a 1,2-, 1,3-, 1,4- or 1,5-diamino (2C-8C)alkane;
  a 1,2- or 1,4- diamino (3C-8C)cycloalkane;
  a 1,1- or 1,2-di(aminomethyl) (3C-8C)cycloalkane;
  a 1,1- or 1,2-di(aminomethyl) heteroalicyclic;
  a di(nitrogen heteroaryl); and
  a methylene di(nitrogen heteroaryl);
if Pt is in the +2 oxidation state (Pt(II)), $R^6$ and $R^7$ do not exist; and,
if Pt is in the +4 oxidation state (Pt(IV)), $R^6$ and $R^7$ are independently selected from the group consisting of —OH, $H_2O$, Cl and (1C-6C)alkylC(O)O—.

2. A compound having the chemical structure:

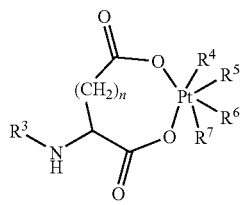

wherein:
n is 0 or 1;
Pt is in a +2 or a +4 oxidation state;
$R^3$ is selected from the group consisting of:
—$R^9$;
-(1C-6C)alkyl-$R^9$;
$R^9$ is -(linker)-$R^{10}$, wherein:
-(linker) is

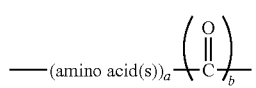

wherein:
a is 2-50;
b is 0 or 1;
$R^{10}$ is selected from the group consisting of:
hydrogen; and,
a natural, semi-synthetic or synthetic backbone polymer;
$R^4$ and $R^5$ are independently selected from the group consisting of:
ammonia;
a primary, secondary or tertiary (1C-6C)alkyl amine;
a (3C-8C)cycloalkyl amine;
an aryl amine;
a nitrogen heteroaryl;
a nitrogen heteroalicyclic;
an aminomethyl nitrogen heteroalicyclic; or,
together, as $R^4$—$R^5$:
  a 1,2-, 1,3-, 1,4- or 1,5-diamino (2C-8C)alkane;
  a 1,2- or 1,4-diamino (3C-8C)cycloalkane;
  a 1,1- or 1,2-di(aminomethyl) (3C-8C)cycloalkane;
  a 1,1- or 1,2-di(aminomethyl) heteroalicyclic;
  a di(nitrogen heteroaryl); and
  a methylene di(nitrogen heteroaryl);
if Pt is in the +2 oxidation state (Pt(II)), $R^6$ and $R^7$ do not exist; and,
if Pt is in the +4 oxidation state (Pt(IV)), $R^6$ and $R^7$ are independently selected from the group consisting of —OH, $H_2O$, Cl and (1C-6C)alkylC(O)O—.

3. The compound of claims 1 or 2, wherein a is 2, 3, or 4.

4. The compound of claims 1 or 2, wherein at least one amino acid is glycine.

5. The compound of claims 1 or 2, wherein the amino acid is independently selected from glycine, leucine, or phenylalanine.

6. The compound of claims 1 or 2, wherein linker is selected from -G-G-, -G-G-G-, -G-G-G-G-, or -G-F-L-G-.

7. The compound of claims 1 or 2, wherein the polymer is poly(N-2-(hydroxypropoyl)methylacrylamide-co-methacrylamide.

8. The compound of claims 1 or 2, wherein $R^4$ and $R^5$ are taken together to form a 1,2- or 1,4-diamino (3C-8C)cycloalkane.

9. The compound of claim 8, wherein $R^4$ and $R^5$ are taken together and form 1R,2R-diaminocyclohexane.

10. The compound of claim 1 wherein the compound has the chemical structure:

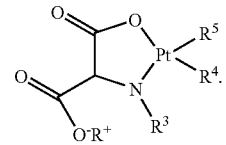

11. The compound of claim 10 wherein the compound has the chemical structure:

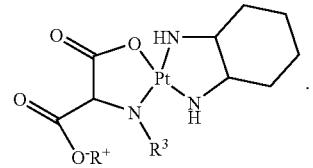

12. The compound of claim 2 wherein the compound has the chemical structure:

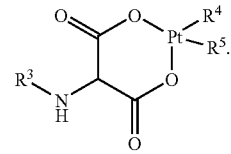

13. The compound of claim 12, wherein the compound has the chemical structure:

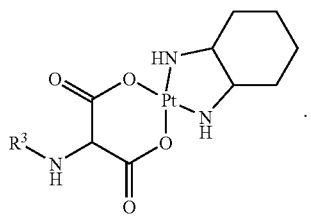

14. The compound of claims 1 or 2, wherein the compound is selected from the group:
p(HPMA)-GFLG-Ama-Pt=DACH;
p(HPMA)-GG-Ama-Pt=DACH;
p(HPMA)-GFLG-Asp=Pt=DACH;
p(HPMA)-GG-Asp=Pt=DACH;
p(HPMA)-GG-C3-Sulf-Ama=Pt=DACH;
p(HPMA)-GG-C3-Sulf-Asp=Pt=DACH;
p(HPMA)-GFLG-C3-Sulf-Ama=Pt=DACH;
p(HPMA)-GFLG-C3-Sulf-Asp=Pt=DACH;
p(HPMA)-GGGG-Ama=Pt=DACH;
p(HPMA)-GGGG-Asp=Pt=DACH; or
p(HPMA)-GGG-Ama=Pt=DACH
wherein:
p(HPMA) is poly(N-2-(hydroxypropyl)methylacrylamide-co-methacrylamide;
G is glycine;
F is phenylalanine;
L is leucine;
C3 is propylene;
Sulf is sulfonyl;
Ama is amidomalonate;
Asp is aspartate;
Pt is in the +2 oxidative state; and
DACH is 1R,2R-diaminocyclohexane.

15. A pharmaceutical composition comprising:
a compound of any preceding claim and one or more pharmaceutically acceptable excipients.

* * * * *